US012775001B2

(12) United States Patent
Xu et al.

(10) Patent No.: US 12,775,001 B2
(45) Date of Patent: Oct. 27, 2026

(54) ADAPTIVE PERFUSION SYSTEMS AND METHODS FOR DRUG RELEASE TESTING

(71) Applicant: THE U.S.A, as represented by the Secretary, Department of Health and Human Services, Silver Spring, MD (US)

(72) Inventors: Xiaoming Xu, Columbia, MD (US); Deval Patel, Frederick, MD (US); Ying Zhang, Centreville, VA (US)

(73) Assignee: The United States of America, as represented by the Secretary, Department of Health and Human Services, Silver Spring, MD (US)

( * ) Notice: Subject to any disclaimer, the term of this patent is extended or adjusted under 35 U.S.C. 154(b) by 383 days.

(21) Appl. No.: 18/268,158

(22) PCT Filed: Dec. 20, 2021

(86) PCT No.: PCT/US2021/064387
§ 371 (c)(1),
(2) Date: Jun. 16, 2023

(87) PCT Pub. No.: WO2022/140271
PCT Pub. Date: Jun. 30, 2022

(65) Prior Publication Data

US 2024/0069001 A1 Feb. 29, 2024

Related U.S. Application Data

(60) Provisional application No. 63/128,505, filed on Dec. 21, 2020.

(51) Int. Cl.
*G01N 33/15* (2006.01)
*B01D 15/08* (2006.01)
(Continued)

(52) U.S. Cl.
CPC ............ *G01N 33/15* (2013.01); *B01D 15/08* (2013.01); *B01D 61/14* (2013.01); *B01D 63/02* (2013.01);
(Continued)

(58) Field of Classification Search
CPC ........ G01N 33/15; G01N 30/14; G01N 30/74; G01N 2030/027; G01N 2030/146;
(Continued)

(56) References Cited

U.S. PATENT DOCUMENTS

2002/0043487 A1* 4/2002 Schick ................ B01D 61/145 210/90
2007/0205155 A1 9/2007 Babcock et al.
(Continued)

OTHER PUBLICATIONS

"Cross Flow Filtration Method Handbook" by GE (Year: 2014).*
(Continued)

*Primary Examiner* — Xin Y Zhong
(74) *Attorney, Agent, or Firm* — Klarquist Sparkman, LLP

(57) ABSTRACT

An in vitro release test (IVRT) method and system is provided for drug release testing. The IVRT method, referred to herein as adaptive perfusion, employ tangential-flow filtration (TFF), where released drug products that are smaller than a molecular weight cutoff (MWCO) of a membrane filter pass therethrough into the permeate. Unreleased drug products are retained by the pores of the filter and are recirculated to a retentate reservoir. Fresh media is provided to the retentate in order to maintain a constant total volume for the sample as well as to maintain sink conditions for the drug release. Drug concentration in the retentate and permeate are evaluated by in situ monitoring with one or more sensors and/or by periodic removal of aliquots from the respective reservoirs. In some embodiments, the mem-
(Continued)

brane filter can be conditioned prior to use in order to improve the accuracy, precision, or both of the subsequent testing.

45 Claims, 16 Drawing Sheets

(51) Int. Cl.
*B01D 61/14* (2006.01)
*B01D 63/02* (2006.01)
*G01N 30/14* (2006.01)
*G01N 30/74* (2006.01)
*G01N 30/02* (2006.01)

(52) U.S. Cl.
CPC ............. *G01N 30/14* (2013.01); *G01N 30/74* (2013.01); *B01D 2315/10* (2013.01); *B01D 2315/16* (2013.01); *G01N 2030/027* (2013.01); *G01N 2030/146* (2013.01)

(58) Field of Classification Search
CPC ........ B01D 15/08; B01D 61/14; B01D 63/02; B01D 2315/10; B01D 2315/16
See application file for complete search history.

(56) References Cited

U.S. PATENT DOCUMENTS

| | | | | |
|---|---|---|---|---|
| 2018/0298343 | A1* | 10/2018 | Sivakumaran ..... | G01N 33/5088 |
| 2019/0270769 | A1* | 9/2019 | Milano ............. | A61K 31/5383 |

OTHER PUBLICATIONS

Henriksen et al., “In vitro evaluation of drug release kinetics from liposomes by fractional dialysis,” *International Journal of Pharmaceutics*, 119(2):231-238 (Jun. 9, 1995).
International Search Report and Written Opinion for related International Application No. PCT/US2021/064387, 16 pages, mailed May 16, 2022.

* cited by examiner

ADAPTIVE PERFUSION SYSTEMS AND METHODS FOR DRUG RELEASE TESTING

CROSS REFERENCE TO RELATED APPLICATIONS

This is the U.S. National Stage of International Application No. PCT/US2021/064387, filed Dec. 20, 2021, which was published in English under PCT Article 21(2), which in turn claims the benefit of U.S. Provisional Application 63/128,505, filed Dec. 21, 2020. The provisional application is incorporated by reference herein in its entirety.

FIELD

The present disclosure relates generally to experimental evaluation of drug products, and more particularly, to adaptive perfusions systems and methods for drug release testing.

BACKGROUND

Since in vitro release testing (IVRT) provides information about the quality and performance of drug products, IVRT has been considered for evaluation of complex drug products, such as nanoemulsions, suspensions, multivesicular liposomes (MVLs), and microspheres. Ideally, an IVRT method would directly correlate changes in a critical quality attribute (CQA) of a drug product formulation to the release characteristics thereof, which correlation could provide valuable information that can be used, for example, to ensure consistent manufacturing quality among different batches of the drug product, to identify post-regulatory-approval changes of a drug product, and/or to allow comparison between different drug products for determination of equivalence. However, developing a fit-for-purpose and robust IVRT method for complex drug products remains a challenge.

SUMMARY

Embodiments of the disclosed subject matter provide in vitro release test (IVRT) methods and systems for drug release testing, referred to herein as adaptive perfusion. The adaptive perfusion methods and systems involve a pressure-driven separation technique, for example, a tangential-flow filtration (TFF) process (also known as crossflow filtration). Any species that are smaller than the pores of a hollow fiber filter (HFF) membrane, or any other type of TFF membrane filter, pass therethrough into the permeate. Meanwhile, larger species are retained by the pores of the HFF membrane, and are recirculated to a retentate reservoir. In particular, released drug products can pass through the HFF membrane into the permeate while unreleased drug products are retained in the retentate and recirculated. A continuous supply of fresh media can be provided to the retentate in order to maintain a constant total volume for the sample as well as to maintain sink conditions for the drug release. Drug concentration in the retentate and permeate can be evaluated, for example, by removal of aliquots of the retentate and permeate from the respective reservoirs and subsequent testing via an ultra-performance liquid chromatography (UPLC) method to provide a time history indicative of the release properties of the drug product. Alternatively or additionally, drug concentration can be monitored in situ, for example, using one or more fiber optic sensors. The permeate can also be collected and tested after completion of a particular experiment to provide a measure of the cumulative amount of drug released. In some embodiments, the HFF membrane can be conditioned prior to use to improve the accuracy, precision, or both of the subsequent drug release testing.

In one or more embodiments, a method comprises, using a filter, performing a diafiltration process on a fluid having a drug sample therein. A retentate from the filter can be recirculated to a fluid supply reservoir. A permeate flow from the filter can be collected in a permeate reservoir. The method can further comprise obtaining a first aliquot from the fluid supply reservoir or a flow of the fluid to the filter, and obtaining a second aliquot from the permeate flow. The method can also comprise analyzing the first and second aliquots to determine one or more properties of the drug sample.

In one or more embodiments, a method can condition a filter for use in a diafiltration process involving a drug sample. The method can comprise connecting a first port of a filter to a source of conditioning solution, and connecting a second port of the filter to a third port of the filter. The first port and the second port can connect to a first volume disposed on a first side of a membrane within the filter. The third port and a fourth port can connect to a second volume on an opposite second side of the membrane from the first side. The method can further comprise flowing conditioning solution from the source into the filter via the first port and out through the fourth port, such that the conditioning solution flows over the first and second sides of the membrane via the connection between the second and third ports. The conditioning solution can comprise a surfactant, an emulsifier, or both. In some embodiments, the diafiltration process is an IVRT method for analyzing the drug sample. In other embodiments, the diafiltration process is a purification stage or other stage in the manufacturing of the drug sample.

In one or more embodiments, a method comprises using a filter, performing a diafiltration process on a fluid having a drug sample therein. A retentate from the filter can be recirculated to a fluid supply reservoir. A permeate flow from the filter can be collected in a permeate reservoir. The method can further comprise measuring a first concentration of the drug sample in the fluid supply reservoir, and measuring a second concentration of the drug sample in the permeate flow. The method can also comprise determining one or more properties of the drug sample based on the measured first and second concentrations.

Any of the various innovations of this disclosure can be used in combination or separately. This summary is provided to introduce a selection of concepts in a simplified form that are further described below in the detailed description. This summary is not intended to identify key features or essential features of the claimed subject matter, nor is it intended to be used to limit the scope of the claimed subject matter. The foregoing and other objects, features, and advantages of the disclosed technology will become more apparent from the following detailed description.

BRIEF DESCRIPTION OF THE DRAWINGS

The following description will proceed with reference to the accompanying drawings, which have not necessarily been drawn to scale. Where applicable, some elements may be simplified or otherwise not illustrated in order to assist in the illustration and description of underlying features. Throughout the drawings, like reference numerals denote like elements.

DETAILED DESCRIPTION

General Considerations

Figure 1A:
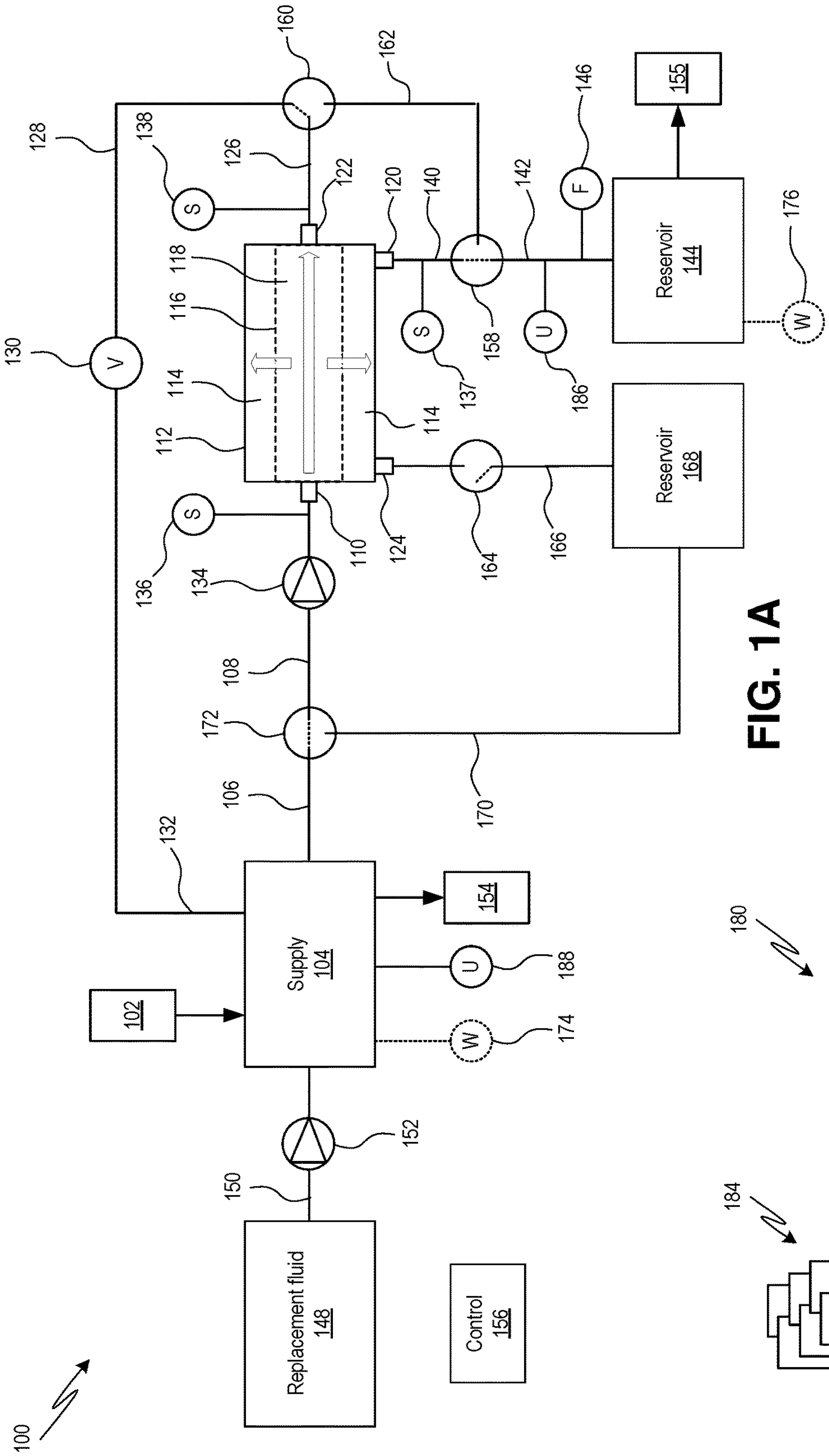
FIG. 1A is a simplified schematic diagram illustrating aspects of an exemplary adaptive perfusion system for drug release testing, according to one or more embodiments of the disclosed subject matter.
Figure 1B:
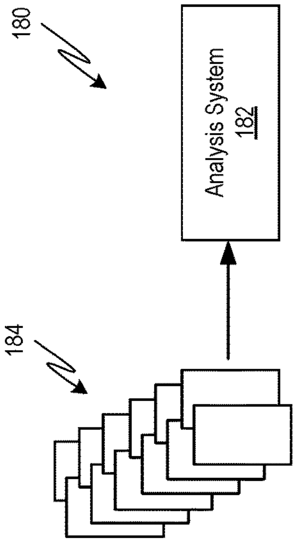
FIG. 1B is a simplified schematic diagram illustrating aspects of an exemplary setup for analyzing aliquots from an adaptive perfusion system for drug release testing.

For purposes of this description, certain aspects, advantages, and novel features of the embodiments of this disclosure are described herein. The disclosed methods and systems should not be construed as being limiting in any way. Instead, the present disclosure is directed toward all novel and nonobvious features and aspects of the various disclosed embodiments, alone and in various combinations and sub-combinations with one another. The methods and systems are not limited to any specific aspect or feature or combination thereof, nor do the disclosed embodiments require that any one or more specific advantages be present, or problems be solved. The technologies from any embodiment or example can be combined with the technologies described in any one or more of the other embodiments or examples. In view of the many possible embodiments to which the principles of the disclosed technology may be applied, it should be recognized that the illustrated embodiments are exemplary only and should not be taken as limiting the scope of the disclosed technology.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like “provide” or “achieve” to describe the disclosed methods. These terms are high-level abstractions of the actual operations that are performed. The actual operations that correspond to these terms may vary depending on the particular implementation and are readily discernible by one of ordinary skill in the art.

The disclosure of numerical ranges should be understood as referring to each discrete point within the range, inclusive of endpoints, unless otherwise noted. Unless otherwise indicated, all numbers expressing quantities of components, molecular weights, percentages, temperatures, times, and so forth, as used in the specification or claims are to be understood as being modified by the term "about." Accordingly, unless otherwise implicitly or explicitly indicated, or unless the context is properly understood by a person of ordinary skill in the art to have a more definitive construction, the numerical parameters set forth are approximations that may depend on the desired properties sought and/or limits of detection under standard test conditions/methods, as known to those of ordinary skill in the art. When directly and explicitly distinguishing embodiments from discussed prior art, the embodiment numbers are not approximates unless the word "about" is recited. Whenever "substantially," "approximately," "about," or similar language is explicitly used in combination with a specific value, variations up to and including 10% of that value are intended, unless explicitly stated otherwise.

Directions and other relative references may be used to facilitate discussion of the drawings and principles herein, but are not intended to be limiting. For example, certain terms may be used such as "inside," "outside,", "top," "bottom," "interior," "exterior," "left," right," "front," "back," "rear," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same.

As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Introduction

Disclosed herein are methods and systems for in vitro release testing (IVRT), for example, to evaluate drug release from complex drug products, such as nanoemulsions, suspensions, multivesicular liposomes (MVLs), microspheres, protein-drug complexes, etc. The disclosed IVRT methods and systems employ a modified tangential flow filtration (TFF) technique, which is referred to herein as adaptive perfusion (AP). In particular, AP involves feeding a diluted drug product sample into a TFF filter, where a pressure differential generated across a filter membrane of the TFF filter drives size-based separation according to a molecular weight cut-off (MWCO) of the filter membrane. Released drug components from the product sample can pass through the filter membrane into the permeate flow, while the remaining product sample is retained by the filter membrane in the retentate flow and recirculated through the TFF filter. Periodic sampling of the retentate (e.g., aliquots from a feed reservoir) and permeate (e.g., aliquots from a permeate flow from the filter) allows for the determination of the rate and extent of drug release from complex drug products. The adaptive aspect of the AP technique arises from feedback-based addition of feed media to maintain a substantially constant dilution volume (e.g., volume of medium on retentate-side of filter membrane, associated fluid circuit, and the feed media reservoir into which the product sample is provided for dilution), as well as from tailoring the AP parameters to correspond to a properties of a particular drug product sample (e.g., size distribution of initial product, size distribution of released product, expected release rate, etc.).

In conventional IVRT methods such as microdialysis, reverse dialysis, or Franz cell diffusion, the testing focuses primarily on quantifying the extent of drug release from the product, with less emphasis on quantifying the rate of drug release. In addition, conventional IVRT methods generally rely on diffusion processes (e.g., via a dialysis membrane) to separate the released drug from the remaining components. Since such processes are necessarily limited by the rate of diffusion, the time required for adequate testing may be prolonged and be unsuitable for testing certain product formulations (e.g., emulsions) or product administration characteristics designed for rapid release (e.g., delivery via ophthalmic route). Conventional IVRT methods may also lack sufficient sensitivity and repeatability to discern minor differences in drug release from complex product formations, for example, differences arising from manufacturing process variations.

Moreover, conventional IVRT methods generally focus on analyzing the released drug, in particular, in order to maintain sink conditions across the membrane (e.g., the use of a larger volume for media on the permeate side of the membrane as compared to retentate side in order to maintain a sufficient concentration gradient to drive diffusion across the membrane). Such methods thus lack an ability to analyze the percentage of drug remaining or to achieve mass-balance in drug transport. Finally, in conventional IVRT methods, the drug release from complex product formulations initiates with passive diffusion of free-drug (e.g., drug not associated with or contained with any product formulation) across the membrane. The process is thus governed by conditions that are not easily adjusted from the standpoint of in vitro drug release testing (e.g., to vary concentration gradient, surface area, etc.), thereby limiting the utility and future avenues for development of conventional IVRT methods.

In contrast, embodiments employing the disclosed AP technique provide a readily-customizable testing platform that does not rely on diffusion for separation and can offer a more complete picture of release characteristics of a drug product by simultaneously measuring components in both the retentate and permeate. In some embodiments, the TFF filter of the AP technique is subject to conditioning with surfactant prior to and after use, which conditioning can reduce variability between experimental runs and/or different filters, thereby improving testing precision, accuracy, or both.

In some embodiments, an AP technique can offer an adjustable rate of removal (e.g., during an experimental run or between experimental runs). The ability to adjust removal rate for each experimental run can allow a user to optimize the feed flow rate and/or the permeate flow based on the type of dosage form under test. For example, higher flow rates can be selected to quickly remove released drug for drug product formulations that exhibit rapid release (e.g., micelle phase within an emulsion that readily releases the drug within a few minutes). Alternatively or additionally, flow rate can be adjusted during an experimental run (e g, manually by a user or automatically by a controller of the AP system) to adjust the rate of drug removal to the permeate, for example, for those drug product formulations that may have multi-phasic release kinetics.

In some embodiments, an AP technique can offer selective retention of components of the drug product formulation. In particular, some preferred components of the drug product formulation can be retained by appropriate selection of the MWCO range of the TFF filter employed. For example, castor oil globules in the nanoemulsions or protein-bound drug containing nanoparticles can be selectively retained by the TFF filter on a retentate-side of the membrane therein and recirculated in a fluid loop connected to the TFF filter, which is otherwise being continuously diluted with fresh media to compensate for any fluid loss via the permeate flow from the TFF filter. This process can assist in effectively differentiating between rapid drug release and extended phase drug release. As noted above, embodiments employing the AP technique allows for performing size-based separation while simultaneously analyzing the drug release from the separated components (e.g., in permeate and retentate).

In some embodiments, an AP technique can provide an environment similar to in vivo conditions. In the AP technique, a continuous flow is provided by the dilution of the drug product sample concurrent with continuous removal of any released drug to a permeate side of the TFF filter, while any remaining drug on a retentate side of the TFF filter is recirculated within the system. Such continuous flow may effectively mimic in vivo conditions experienced by the drug product in actual use, for example, continuous dilution of the drug product at the ocular surface due to tear turnover and continuous absorption of drug after releasing from the complex formulations (e.g., emulsions). In another example, the experience of the drug product within the AP system can be similar to the drug release conditions experienced in parenteral drug delivery, where release of drug into the blood stream occurs during circulation and drug removal occurs due to absorption at the target tissue or organ.

In some embodiments, an AP technique can provide controllable dilution, for example, by altering a rate of permeate flow (e.g., via adjustment of feed flow rate into the TFF filter, adjustment of backpressure applied to flow from an outlet of the TFF filter, or both). Dilution ratio during release testing may be especially critical for certain dosage forms, such as ophthalmic drugs. For example, dilution of nanosuspensions can be give rise to rapid (e.g., near instantaneous) dissolution of the nanoparticles and may thus diminish the potential for differentiating between formulations. Moreover, for nanoemulsions, the initial equilibrium states of the oil/aqueous phases present in the formulation may govern the drug distribution in each phase, with high dilution ratios at initiation of an IVRT testing potentially masking differences in drug release between formulations if the rate of drug removal across the membrane is not rapid enough. Thus, in some embodiments employing the AP technique, a controllable rate of dilution can be achieved by optimizing the rate of permeate flow so that the sample is initially diluted at a lower ratio, and the dilution ratio can be increased to a higher level (e.g., in a linear, step-wise, or any other manner) as the testing progresses. The ability to customize dilution level during an experimental run allows embodiments employing the AP technique to discern minor differences in drug release profiles (e.g., in emulsions with different globule sizes).

In some embodiments, an AP technique can provide selective evaluation of excipient impact on drug release. By appropriate selection of MWCO of the TFF filter used in the AP technique, complex excipients (e.g., polymers composed of hydrophilic and hydrophobic monomers) can be selectively retained on the retentate side of the TFF filter based on their molecular weight and recirculated within the system. The impact of these excipients on drug release can be then be studied. For example, compositional or manufacturing process changes can be made to a particular drug product formulation, and the resulting impact on drug release can be studied using the AP technique.

In some embodiments, an AP technique can minimize, or at least reduce, degradation of the drug during release thereof. As noted above, the AP technique allows for custom tuning of the feed flow rate and the permeate flow rate. Fresh media is supplied as replacement fluid to compensate for volume lost to the permeate flow rate, and thus the fresh media supply rate can also be tuned. The fresh media supply rate governs the rate at which the drug product sample gets diluted with media, as well as the duration for completion of the IVRT experimental run. For drugs that may be susceptible to degradation when exposed to large media volumes for prolonged periods (e.g., as suggested by FIGS. 8B and 9B), the initial media volume and subsequent flow rates during an experimental run can be tailored in the AP technique to reduce volumes and/or testing duration to avoid such degradation, or at least reduce the risk or amount of degradation.

System Embodiments

FIG. 1A shows an exemplary system 100 that can be used to perform AP for IVRT of a drug product sample. The system 100 includes a feed container or reservoir 104 (also referred to herein as a retentate reservoir or feed supply), a tangential flow filter (TFF) 112, a back-pressure valve 130, a permeate container or reservoir 144, a first pump 134, a fresh media container or reservoir 148 (also referred to herein as fresh media reservoir or replacement fluid supply), and a second pump 152. The system 100 also includes a plurality of fluid conduits (e.g., tubing) interconnecting the various system components to form one or more fluid circuits, and a plurality of valves for reconfiguring flow paths in the fluid circuit. The system 100 also includes a plurality of sensors for monitoring operation thereof, for example, pressure sensors 136, 137, 138, and flux sensor 146.

An outlet of the feed reservoir 104 is coupled to an inlet of first pump 134 (e.g., a peristaltic pump) via fluid conduits 106, 108. The outlet of the first pump 134 is coupled to an inlet 110 of TFF filter 112, and pressure sensor 136 can be configured to measure a pressure at the inlet 110 and provide a sensor signal responsively thereto. The inlet 110 of TFF filter 112 directs fluid to a first volume 118 (e.g., feed stream or retentate volume) on a retentate-side of each membrane filter 116. Each membrane filter 116 separates the first volume 118 from a second volume 114 (e.g., filtered or permeate volume), wherein fluid and other components therein that have a molecular weight less than a MWCO of membrane filter 116 can pass therethrough from the first volume 118 to the second volume 114. The second volume 114 connects to a first outlet 120, through which permeate in the second volume 114 can flow from the TFF filter 112 to permeate reservoir 144 for collection and/or sample testing. Pressure sensor 137 is coupled to the flow-path between the first outlet 120 and permeate reservoir 144, for example, along fluid conduit 140. Pressure sensor 137 can be configured to measure the pressure at the outlet 120 and provide a sensor signal responsibly thereto. Flux sensor 146 is disposed along the flow-path between the first outlet 120 and permeate reservoir 144, for example, along fluid conduit 142. The flux sensor 146 can be configured to measure a rate of permeate flow (e.g., fluid flow rate or mass flow rate) and provide a sensor signal responsively thereto.

An outlet of fresh media reservoir 148 is coupled to an inlet of second pump 152 (e.g., a peristaltic pump) via fluid conduit 150. The outlet of second pump 152 is coupled to an inlet of feed reservoir 104, such that fresh media from reservoir 148 can be supplied to the feed reservoir 104 by second pump 152 to compensate for any fluid lost to the permeate flow through filter membrane 116, thereby maintaining a substantially constant volume in feed reservoir 104 (and for combination of feed reservoir 104 and the fluid circuit and filter volumes 118 on a retentate side of membrane filter 116).

The second volume 114 can also connect to a third outlet 124, which is disposed at an opposite end of the TFF filter 112 from the second outlet 120 and at a same end of the TFF filter 112 as the inlet 110. As described in further detail below, the third outlet 124 can be selectively opened, for example, via valve 164 (e.g., a multi-position valve or an open-close valve) for pre-testing or post-testing processing of the TFF filter 112. In the illustrated configuration, the third outlet 124 is connected to a reservoir 168 via fluid conduit 166; however, in some configurations, the third outlet 124 can instead be directed to waste (e.g., where fluid conduit 166 serves as drain line for waste) or directly connected to fluid conduit 170 without an intervening reservoir 168.

At an opposite end of the TFF filter 112 from inlet 110, a second outlet 122 connects to the first volume 118, through which retentate in the first volume 118 can flow from the TFF filter 112. The second outlet 122 is connected back to the feed reservoir 104 via fluid conduits 126, 128, and 132, thereby forming a recirculating fluid circuit or fluid loop by which retentate from TFF filter 112 can be returned to inlet 110 for repeated filtration processing. Pressure sensor 138 can be configured to measure a pressure at the second outlet 122 and provide a sensor signal responsively thereto. Backpressure valve 130 is disposed along the flow-path between the second outlet 122 and the feed reservoir 104 and is configured to apply a back pressure to the second outlet 122, for example, by reducing a cross-sectional area for fluid flow through conduit 128.

Figure 5B:
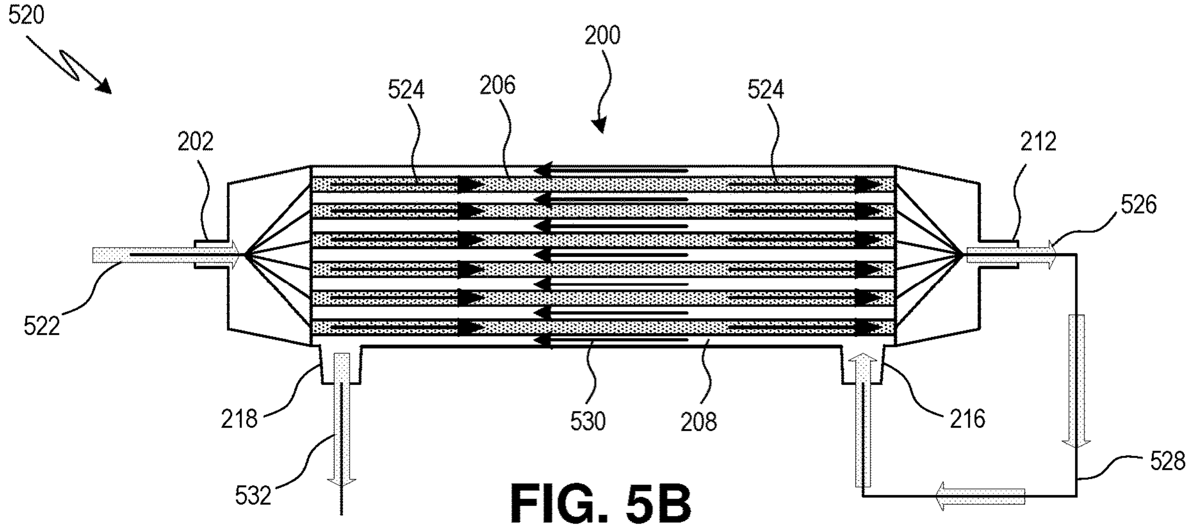
FIG. 5B shows an exemplary partial open loop configuration for the hollow-fiber filter of FIG. 2A, for example, during at least part of the filter conditioning method of FIG. 5A.

Valves 158, 160, 164, 172 provided at various positions around the fluid circuit with respect to inlet 110 and outlets 120, 122, 124 of the TFF filter 112 can be used to reconfigure the fluid circuit according to different operational modes. One, some, or each of the valves 158, 160, 164, 172 can thus be a multi-position valve (e.g., three or four position valve) capable of directing flows along multiple different paths. During an IVRT operational mode, the valves 158, 160, 164, and 172 are configured as shown in FIG. 1A, thereby providing the TFF filter with an open loop configuration (e.g., as shown in FIG. 6B). For a conditioning operational mode (whether pre-IVRT or post-IVRT), valves 158 and 160 are actuated to connect first outlet 120 and second outlet 122 via fluid conduits 126, 162, and 140, and valve 164 is actuated to connect third outlet 124 to reservoir 168 or a waste line or receptacle (not shown). During the conditioning operational mode, the valve 172 remains configured as shown in FIG. 1A, thereby providing the TFF filter with a partial-open loop configuration (e.g., as shown in FIG. 5B). For a cleaning operational mode (which may be part of post-IVRT reconditioning), valves 158 and 160 are actuated to connect first outlet 120 and second outlet 122 via fluid conduits 126, 162, and 140. In addition, valve 164 is actuated to connect third outlet 124 to reservoir 168 via fluid conduit 166, and valve 172 is actuated to connect an inlet of first pump 134 to reservoir 168 via fluid conduits 108 and 170. During the cleaning operational mode, the reservoir 168 can be filled with an organic solvent (e.g., ethanol) and/or other cleaning solution, while the valves 158, 160, 164, and 172 provide the TFF filter with a closed loop configuration (e.g., as shown in FIG. 7B).

In some embodiments, the fluid circuit can be provided with additional valves (not shown), for example, to connect the fluid circuit to different fluid sources, such as a deionized water source, a source of organic solvent, a source of conditioning fluid, etc. Alternatively, in some embodiments, one or more of valves 158, 160, 164, 172 can be omitted, for example, when the fluid circuit is manually reconfigured by a user according to a desired operational mode.

Operation of the system 100 and its various components can be controlled by a controller 156. As such, controller 156 can be operatively coupled to pumps 134, 152, pressure sensors 136, 137, 138, backpressure valve 130, valves 158, 160, 164, 172, or any combination thereof in order to receive sensor or status signals therefrom and send command or control signals thereto. For example, during an IVRT operational mode, the controller 156 can automatically control pump 152 to provide fresh media to feed reservoir 104 from replacement fluid reservoir 148 at a rate that substantially corresponds to a permeate flow rate measured by flux sensor 146 (e.g., using any type of controller loop feedback mechanism, such as proportional-integral-derivative control).

Controller 156 may also control injection device 102 (e.g., for providing an initial sample of drug product to feed reservoir 104) and/or sampling devices 154, 155 (e.g., for periodically obtaining aliquots for analysis). For example, injection device 102 and/or sampling devices 154, 155 can be a syringe pump, automated pipette, or any other liquid handling device that can deliver fluid to and/or retrieve a portion of fluid from a reservoir. Although shown as interacting with reservoir 144, in some embodiments, sampling device 155 is configured to obtain an aliquot for analysis from the permeate flow from outlet 120 (e.g., within fluid conduit 142) rather than from the permeate collected in reservoir 144. Similarly, although shown as interacting with reservoir 104, in some embodiments, sampling device 154 is configured to obtain an aliquot for analysis from the retentate flow into inlet 110 (e.g., within fluid conduit 106 or 108) or out of outlet 122 (e.g., within fluid conduit 126, 128, or 132).

In some embodiments, weight can be monitored instead of or in addition to permeate flow rate in order to regulate fresh media flow rate. For example, feed reservoir 104 can have a first sensor 174 that monitors a weight thereof, and/or permeate reservoir 144 can have a second sensor 176 that monitors a weight thereof. Controller 156 can control pump 152 to provide fresh media to feed reservoir 104 to maintain a constant weight of feed reservoir 104 based on signals from first sensor 174, and/or to match changes in weight of permeate reservoir 144 based on signals from second sensor 176. In another example, during an IVRT operational mode, the controller 156 can control pump 134 and back-pressure valve 130 responsively to pressure signals from pressure sensors 136, 138, so as to provide a desired transmembrane pressure for TFF filter 112.

The controller 156 can operate system 100 to provide three generally sequential modes of operation—a pre-conditioning mode, an IVRT mode, and a re-conditioning mode. The pre-conditioning mode can involve washing and conditioning of the TFF filter by using a specific medium and with the TFF filter in a particular configuration. For example, the pre-conditioning mode can be performed as described below with respect to FIG. 5A. The re-conditioning mode can be similar to the pre-conditioning mode, but is performed after the IVRT mode rather than before. The re-conditioning mode can involve washing, re-conditioning, and storing of the TFF filter for future use.

In the IVRT mode, the aspects of the process can be regulated by controller 156 to control drug release. This regulation includes swift initiation of feed flow from feed reservoir 104 upon initial sample dilution (e.g., injection via device 102), supply of fresh media from reservoir 148 to compensate for volume loss due to permeate flow via outlet 120, and monitoring of permeate flow. In addition to providing feedback for replacement fluid, the monitoring of the flow rate through the permeate outlet can also be used to calculate the amount of drug released (or at least provide an approximation thereof based on aliquot analysis), for example, cumulative mass of drug released can be calculated using the following equation:

$$\text{cumulative mass of drug released} = \sum_{i=1}^{n} (\text{permeate flux})_i \times (\text{time}_i - \text{time}_{i-1}) \times (\text{measured permeate concentration})_i$$

During the IVRT mode, a portion of the sample containing dispersed particles smaller than the pores of the filter membrane 116 pass through into the permeate volume 114, whereas larger particles are recirculated back to the feed reservoir 104 in a continuous loop. The pressure gradient across the filter membrane 116 and the size-based separation can be tailored to the type of drug product formulation being analyzed, for example, by appropriate selection of feed flow rates, backpressure, or the MWCO of the filter membrane. For example, for drug products wherein a rapid rate of drug release is expected, the feed flow can be adjusted to higher flow rates, whereas lower feed flow rates can be used when slow drug release is expected. Even though the sample is circulated in a closed loop in system 100, the simultaneous size based separation and the concurrent dilution of the sample can overcome any media volume restrictions and otherwise provide substantially continuous sink conditions.

During the IVRT mode, samples (e.g., aliquots) are periodically obtained from the feed supply reservoir 104 by sampling device 154 and from the permeate flow from outlet 120 by sampling device 155. The obtained samples can then be analyzed to determine an amount of drug that has been released to the permeate as well as the remaining drug in the retentate that has not yet been released. In some embodiments, the samples can be collected and provided to separate setup 180 for analysis. For example, a batch 184 of samples from an entire IVRT run can be provided to a data analysis system 182 (e.g., ultra-performance liquid chromatography system (UPLC)) for sequential or parallel analysis. For example, the batch 184 of samples can be provided in a microtiter plate, well plate, or any other type of device that can contain multiple aliquots (in an organized arrangement or otherwise) for analysis by liquid chromatography (e.g., high-performance liquid chromatography (HPLC), UPLC, etc.), mass spectrometry, or any other analysis technique (or combination thereof). Alternatively or additionally, each aliquot can be sent for analysis by system 182 without otherwise waiting for other time-sequence samples to compose a batch.

In some embodiments, instead of separate analysis system 182 or in addition thereto, system 100 can be provided with one or more sensors to monitor in situ drug concentration, for example, in real-time or substantially real-time. In such embodiments, the withdrawal of separate aliquots using sampling devices 154, 155 may not be necessary. For example, system 100 can include a first concentration monitoring sensor 186 coupled to the flow-path between the first outlet 120 and permeate reservoir 144, for example, along fluid conduit 142. First concentration monitoring sensor 186 can be configured to measure drug concentration and/or other compositional details of the permeate flowing from outlet 120 to permeate reservoir 144 and to provide a sensor signal responsibly thereto. Alternatively or additionally, system 100 can include a second concentration monitoring sensor 188 coupled to the feed reservoir 104. Second concentration monitoring sensor 188 can be configured to measure drug concentration and/or other compositional details of the retentate within the feed reservoir 104. For example, the first and second concentrating monitoring sensors 186, 188 can be an in situ fiber-optic ultra-violet (UV) sensor, such as or similar to a fiber optic UV-Vis system (Pion µDiss Profiler™, Billerica, MA). It will be appreciated that the configuration, connections, and components of the system 100 are exemplary only, and other configurations, connections, and components can be used to perform AP for IVRT, according to one or more contemplated embodiments. Moreover, operational parameters, configurations, and other options for the IVRT mode and associated system 100 performing the AP technique can be selected to provide optimal results for a particular drug release test and/or particular drug product formulation. For example, the operational parameters, configurations, and other options include feed flow rates, backpressure, initial sample-to-media dilution ratio, tubing lengths, solvents for pre-conditioning, and sequence of pre-conditioning. Selection of an appropriate TFF filter can also depend upon drug properties, dosage form (e.g., emulsions vs. suspensions), filter membrane chemistry, and TFF filter types (length, surface area, internal volume, MWCO and pressure capacity).

Available variables or options for conditioning of the filter can include, but are not limited to, surfactant (e.g., type), concentration (e.g., % w/v), and configuration of the fluid circuit connected to the filter during the conditioning process (e.g., open loop, partial-open loop, or closed loop). In some embodiments, the surfactant can be polysorbate-80 at a concentration of 0.07% w/v, and the fluid circuit configuration can be partial-open loop, for example, as described below with respect to FIGS. 5A-5B. The 0.07% w/v concentration can result in higher flux values through the conditioned membrane filter as compared to lower concentration values (e.g., 0.02% w/v). The partial-open loop configuration can yield higher filter-to-filter consistency and data reproducibility as compared to conditioning using the other fluid circuit configurations.

Available variables or options for performing adaptive perfusion can include, but are not limited to, feed flow rate (e.g., ml/min), applied backpressure, and sample dilution (e.g., media-to-sample dilution ratio). The selected feed flow rate and applied backpressure can be a function of the type of drug product to be analyzed (e.g., nanoemulsions versus pure drug solution), for example, to define a removal rate (e.g., permeate flow rate) that substantially corresponds to an anticipated release rate for a particular drug product. Since the pressure difference between the retentate and permeate sides of the membrane filter (e.g., the transmembrane pressure) is a function of both feed flow rate and applied backpressure, the feed flow rate and backpressure can be selected to maximize flux values (or at least achieve a desired minimum permeate flow) through the membrane filter without otherwise exceeding the manufacturer-defined limitations of the filter (e.g., maximum operating pressure and/or maximum operating flow rate). Dilution can also be tailored to the drug product being analyzed, as well as to enhance filter performance In some embodiments, the feed flow rate can be at least 100 ml/min, for example, 200 ml/min, and the sample dilution can be 200:1 on a volume basis. The 200:1 dilution can help reduce the possibility of membrane fouling and can increase overall efficiency of the adaptive perfusion process as compared to lower dilution rates (e.g., 50:1).

Available variables or options for the filter can include, but are not limited to, the configuration of the TFF module (e.g., hollow fibers, spiral wound cartridge, flat plate or cassette, etc.), water affinity (e.g., hydrophilic versus hydrophobic, and the various modifications therefor), size (e.g., diameter, effective length, surface area, etc.), and molecular weight cut-off (MWCO). The MWCO of the filter can be selected based on the drug product to be analyzed (e.g., based on the globule size range of nanoemulsions), in particular, such that released drug particles can pass through the filter into the permeate while unreleased drug particles can be retained on the retentate-side of the filter. In some embodiments, the MWCO can be 100 kD, which may be less susceptible to fouling than higher MWCO values (e.g., 300 kD or 500 kD)

In some embodiments, the water affinity of the filter membrane can be hydrophilic resulting from modified polyethersulfone (mPES), which enable higher flux rates, increase resistance to fouling, and/or lower drug adsorption to the membrane, among other things. Alternative water-affinity modifications can include, but are not limited, to mixed cellulose ester (ME) and polyethersulfone (PES) for hydrophilic and polysulfone (PS) for hydrophobic.

Figure 2A:
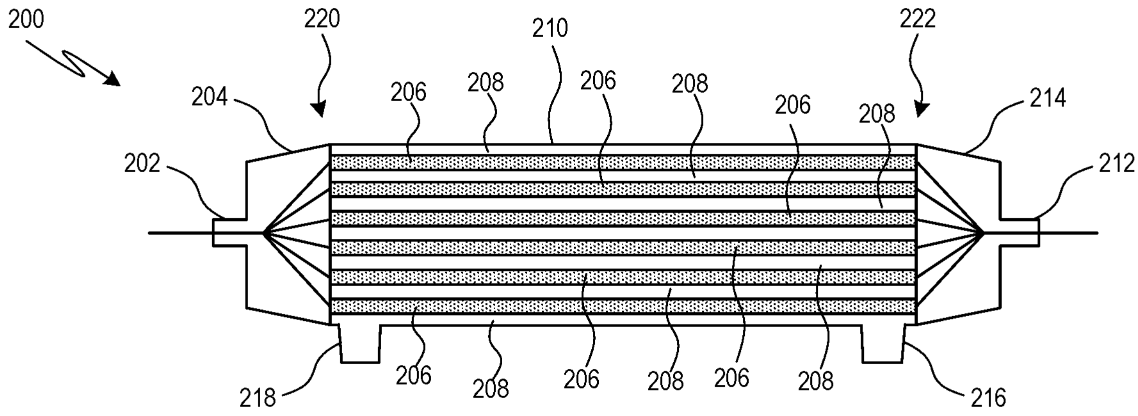
FIG. 2A is a simplified cross-sectional view illustrating aspects of a hollow-fiber filter that can be employed in an adaptive perfusion system for drug release testing.

In some embodiments, the TFF filter module can have a hollow fiber configuration, with each fiber having a diameter of 0.5 mm. In some embodiments, the hollow fiber configuration can provide an effective length of 20 cm and a surface area of 20 $cm^2$. The hollow fiber configuration may yield a simpler flow path and lower void volumes as compared to other configurations. For example, FIG. 2A shows an exemplary hollow fiber filter (HFF) 200 that can be used as TFF filter 112 in system 100 of FIG. 1A, or in any other system performing the disclosed AP technique. HFF 200 has a plurality of ports, in particular, first port 202, second port 212, third port 216, and fourth port 218. In some embodiments, the first port 202 can be used as an inlet port, and second port 212 can be used as a retentate outlet port. The inlet port 202 connects to an inlet manifold 204, which redirects fluid flow to each of a plurality of hollow fibers 206 at inlet end 220 of HFF 200. Similarly, the retentate outlet port 212 connects to an outlet manifold 214, which collects fluid flow from each of the fibers 206 at outlet end 222 of HFF 200. The multiple hollow fibers 206 are disposed in parallel within a substantially-cylindrical housing 210 that defines a common permeate volume 208 between and surrounding the individual fibers 206. The third port 216 and fourth port 218 can connect to this permeate volume 208 at opposite ends of the HFF 200. For example, third port 216 connects to permeate volume 208 at outlet end 222 and can be used as a permeate outlet port. The fourth port 218 connects to permeate volume 208 at inlet end 220. The fourth port 218 can be used as an outlet port during preconditioning or re-conditioning of HFF 200, with the fourth port 218 being otherwise generally closed (e.g., during IVRT operational mode).

Figure 2B:
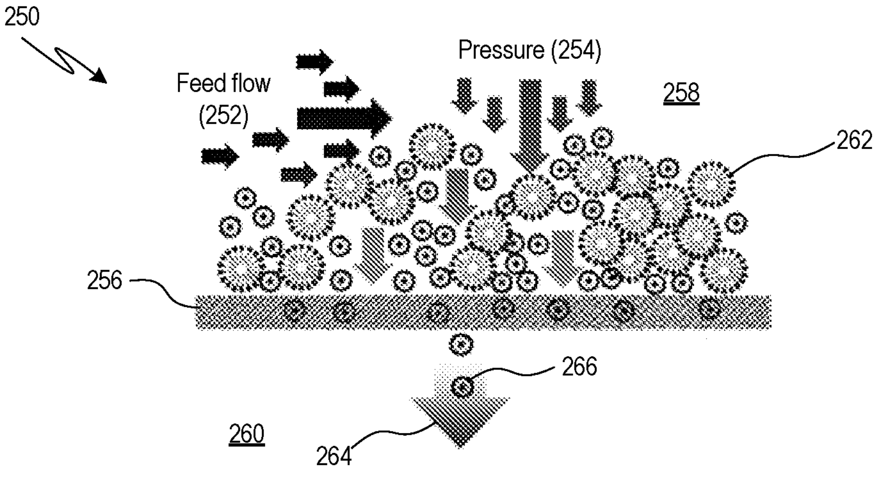
FIG. 2B is a simplified schematic diagram illustrating the size-based separation process at the membrane of a tangential flow filter.

Each fiber 206 has a substantially cylindrical wall surrounding a hollow interior volume (e.g., retentate volume). The cylindrical wall of the fiber is formed of a filter membrane that provides the desired size separation. For example, as shown in the configuration 250 of FIG. 2B, the filter membrane 256 delineates the retentate volume 258 from the permeate volume 260. When feed flow 252 enters the retentate volume 258 of the hollow fibers (or any other TFF filter type) and a pressure 254 is applied across the filter membrane 256 (e.g., due to backpressure applied to the retentate flow outlet), fluid 264 and particles 266 (e.g., released drug) therein having a molecular weight less than the MWCO of the filter membrane 256 can pass therethrough to the permeate volume 260. At the same time, particles 262 within the feed flow 252 that have a molecular weight greater than the MWCO of the filter membrane 256 (e.g., unreleased drug products) are retained on the retentate side thereof despite the applied pressure 254. The retained particles 262 can thus be passed to the retentate outlet of the HFF 200 for recirculation, for example, to allow additional time for drug release.

Figure 3A:
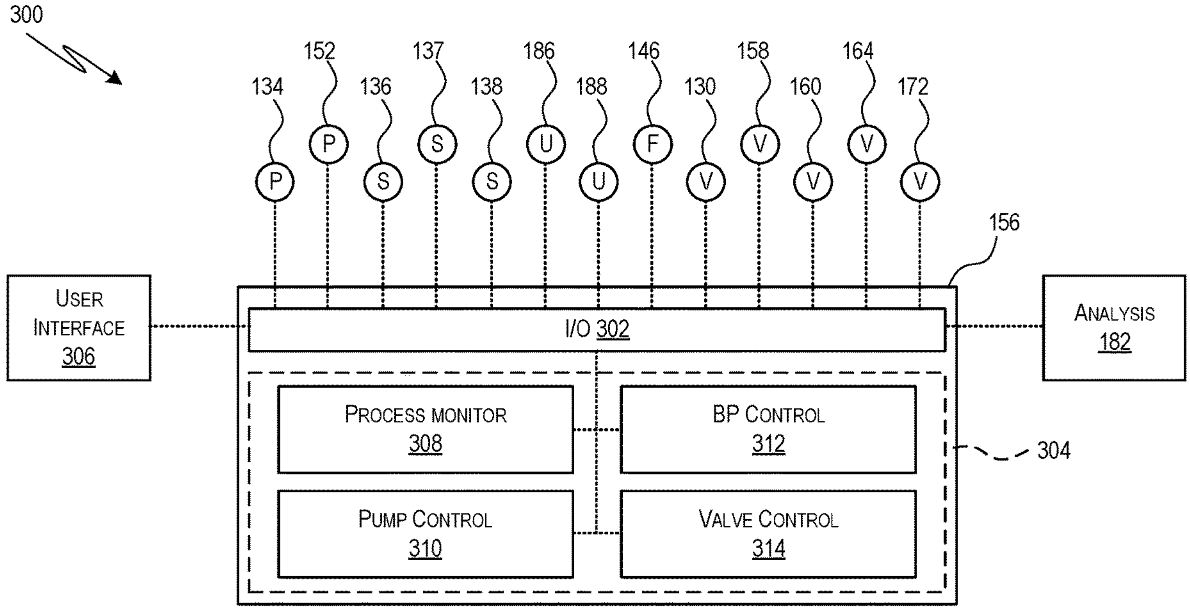
FIG. 3A is a simplified schematic diagram illustrating operational aspects of a control system of an adaptive perfusion system.

In some embodiments, controller 156 of system 100 automate most or all of the AP technique, including adjustment, monitoring, and recording of various operational parameters and coordinating timing of various steps in the AP process. For example, FIG. 3A shows an exemplary setup 300 for operation of controller 156. In the illustrated example, controller 156 has an input/output (I/O) interface 302 through which controller 156 is operatively connected to various components of system 100 to control operation thereof or receive data or information therefrom. For example, controller 156 connects directly or indirectly (e.g., via one or more intervening components, such as a separate control module of a pump) to one, some, or all of pump 134, pump 152, pressure sensor 136, pressure sensor 137, pressure sensor 138, flux sensor 146, concentration monitoring sensor 186, concentration monitoring sensor 188, backpressure valve 130, valve 158, valve 160, valve 164, and valve 172 via input/output interface 302.

The controller 156 can have one or more modules or sub-modules that coordinate respective functions associated with performance of an AP process. In the illustrated example of FIG. 3A, an AP module 304 of controller 156 includes a process monitor sub-module 308, a pump control sub-module 310, a back-pressure control sub-module 312, and a valve control sub-module 314. The AP module 304 coordinates operation of the individual sub-modules to perform processes associated with the different operational modes of system 100, for example, as described in further detail below with respect to FIGS. 5A-7B. Each module 304 or sub-module 308-314 can execute logic or other computer instructions to perform assigned functions. Process monitor sub-module 308 is configured to receive sensor signals from pressure sensor 136, pressure sensor 137, pressure sensor 138, concentrating monitoring sensor 186, concentration monitoring sensor 188, and/or flux sensor 146. For example, based on process requirements defined by a user or the system for a particular IVRT experimental run, the process monitor sub-module 308 may issue requests or commands to other sub-modules to maintain compliance of the measured parameters.

Pump control sub-module 310 is configured to generate control signals for pump 134 and pump 152. For example, pump control sub-module 310 sends a control signal to pump 134, via I/O interface 302, to provide a user- or system-defined feed flow rate to TFF filter 112 in FIG. 1A. In another example, pump control sub-module 310 sends a control signal to pump 152, via I/O interface 302, to provide a flow rate for replacement fluid responsive to a flux rate detected by flux sensor 146. In such configurations, the process monitor sub-module 308 may provide an appropriate internal signal to the pump control sub-module 310, for example, by employing proportional-integral-derivative (PID) control using the signal from flux sensor 146 as feedback.

Back-pressure control sub-module 312 is configured to generate control signals for back-pressure valve 130. For example, back-pressure control sub-module 312 sends a control signal to valve 130, via I/O interface 302, to provide a user- or system-defined back pressure at the outlet 122 of TFF filter 112 in FIG. 1A. In some embodiments, process monitor sub-module 308 may provide an appropriate internal signal to the back-pressure control sub-module 312, for example, based on measured pressure signals from pressure sensors 136, 138, in order to provide a desired transmembrane pressure across the membrane 116 of TFF filter 112.

Valve control sub-module 314 is configured to generate control signals for valves 160, 164, 172. For example, valve control sub-module 314 sends a control signal to valves 160, 164, 172, via I/O interface 302, to change a configuration of the fluid circuit between open loop, partial open-loop, and closed loop configurations, depending on the mode of operation of system 100 in FIG. 1A. In some embodiments, valve control sub-module 314 generate control signals to change between configurations responsive to a user command received via I/O interface 302 or based on a stored recipe or process flow for an operational mode (e.g., expiration of a time for an experimental IVRT run).

Moreover, in some embodiments, functions performed by one of the sub-modules of AP module 304 illustrated in FIG. 3A can be combined with other sub-modules, either as a new sub-module or integrated into an existing sub-module. For example, the sensor monitoring functions performed by process monitor sub-module 308 can be distributed among the other three sub-modules 310-314. In such an example, the pressure signals from pressure sensors 136, 138 can be processed and used by back-pressure control sub-module 312 to generate control signals for back-pressure valve 130, and the flow rate from flux sensor 146 can be processed and used by pump control sub-module 310 to generate control signals for pump 134. Other configurations for sub-modules of AP module 304 are also possible according to one or more contemplated embodiments.

Figure 5A:
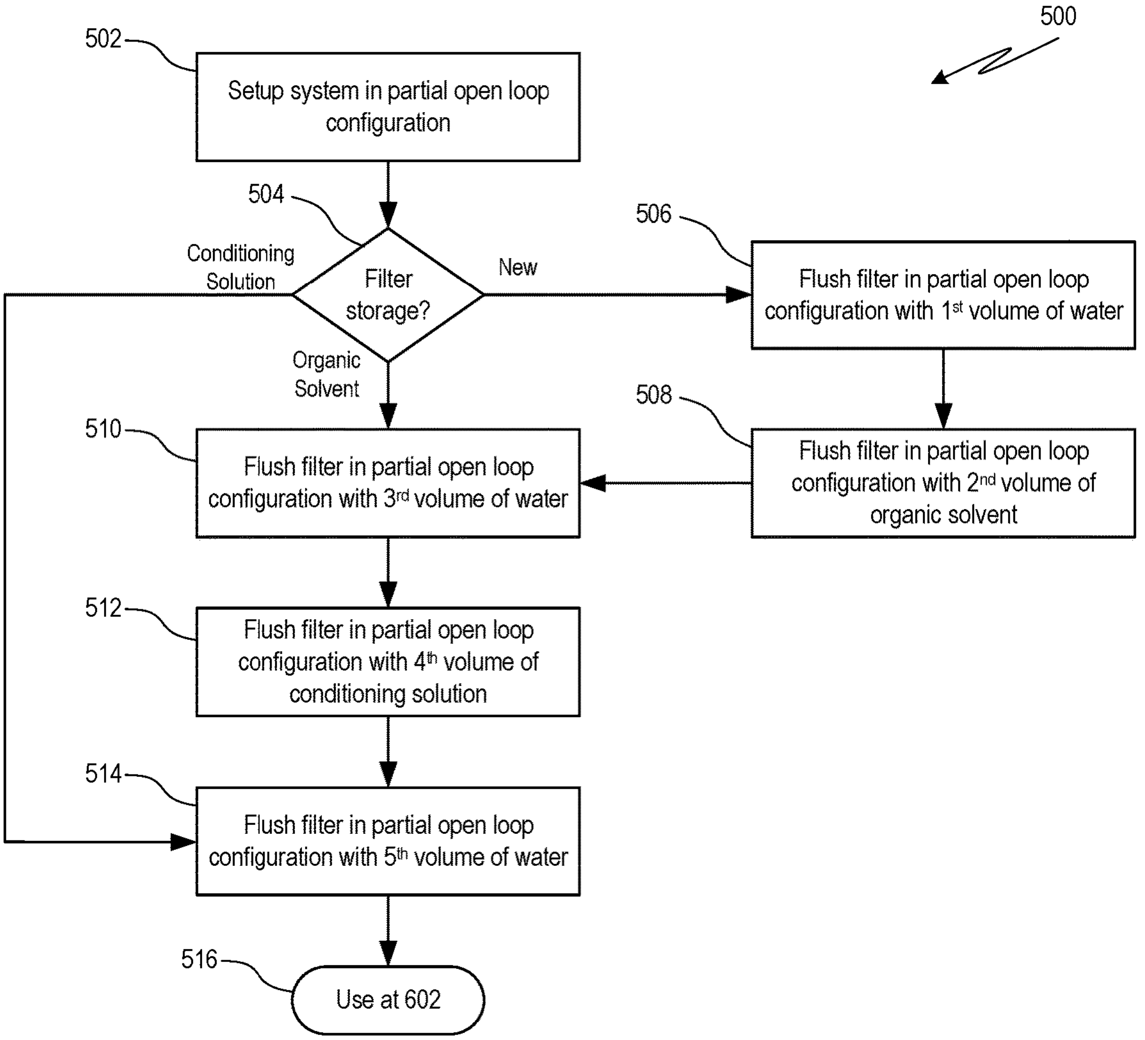
FIG. 5A is a process flow diagram for an exemplary method of conditioning a filter for use in a subsequent diafiltration process.
Figure 6A:
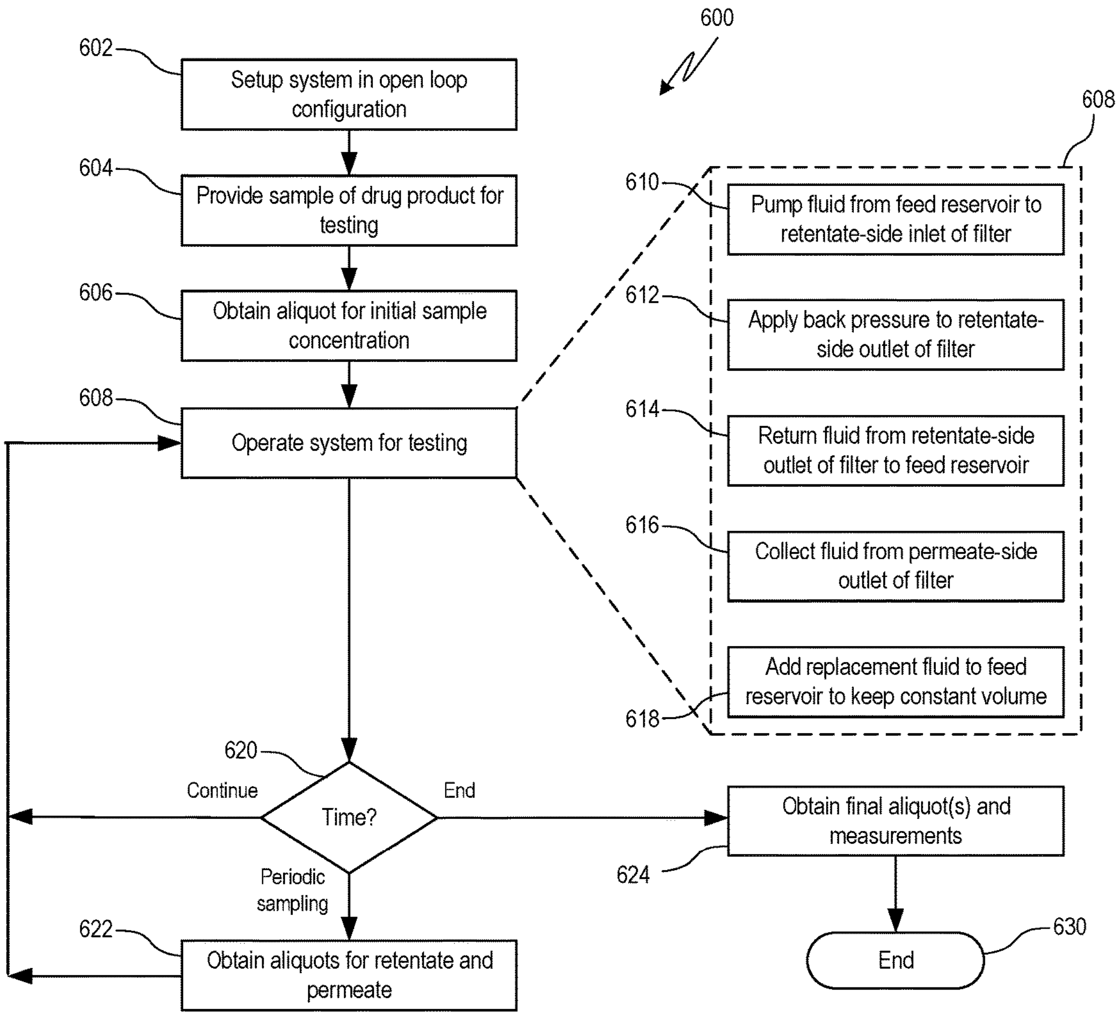
FIG. 6A is a process flow diagram for an exemplary method of performing adaptive perfusion for drug release testing.
Figure 6B:
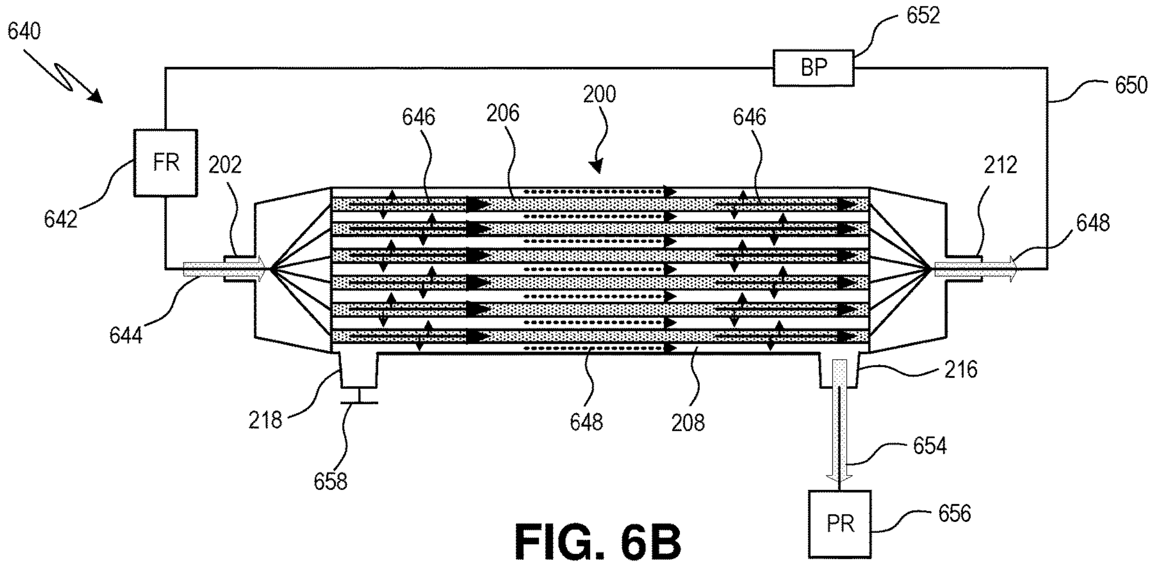
FIG. 6B shows an exemplary open loop configuration for the hollow-fiber filter of FIG. 2A, for example, during a least part of the adaptive perfusion method of FIG. 6A.
Figure 7A:
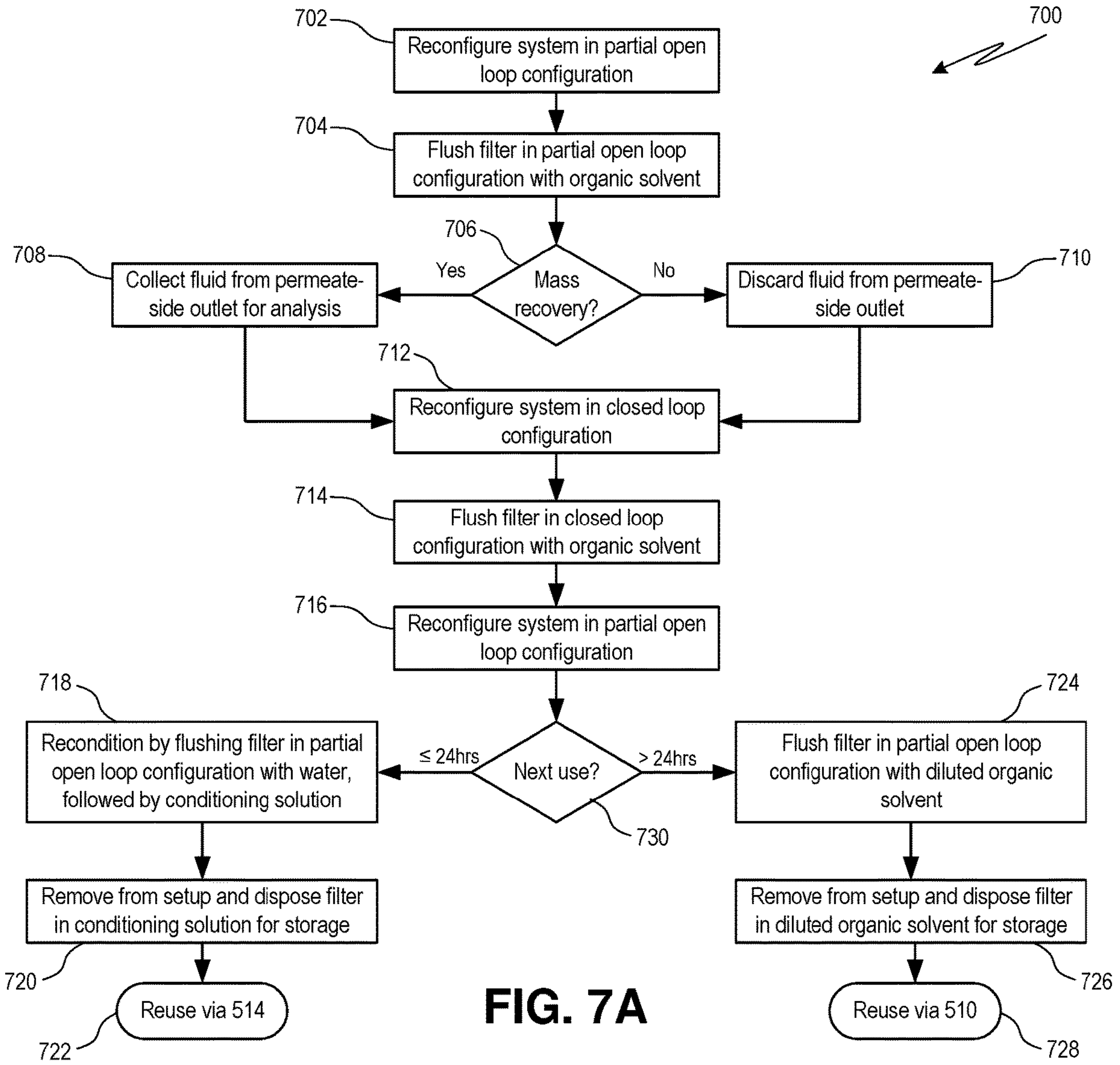
FIG. 7A is a process flow diagram for an exemplary method of performing reconditioning and storage of a filter after a diafiltration process.
Figure 7B:
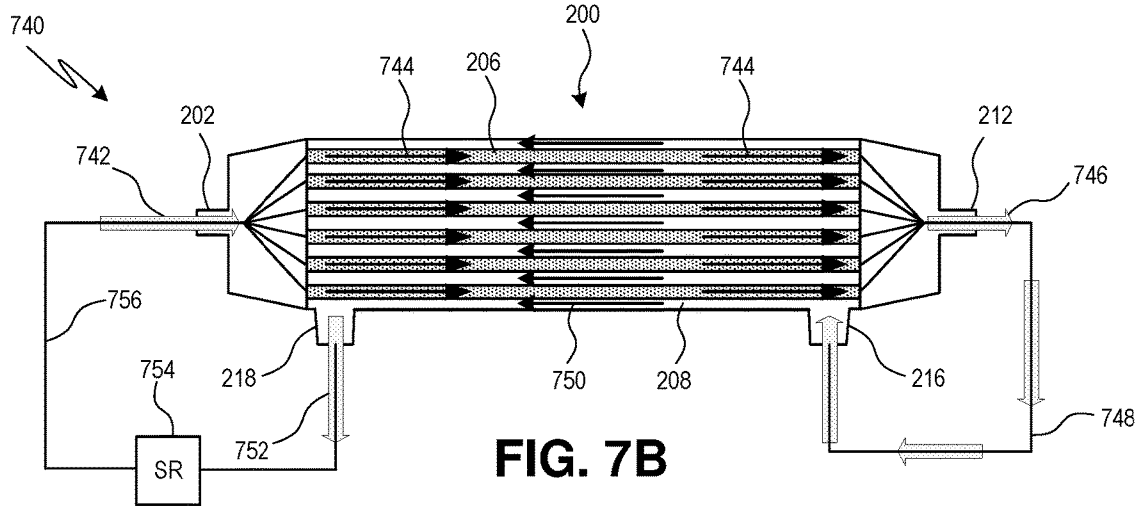
FIG. 7B shows an exemplary closed loop configuration for the hollow-fiber filter of FIG. 2A, for example, during a least part of the reconditioning of FIG. 7A.

AP module 304 further includes process flow or recipe details for each operational mode (e.g., as shown in FIGS. 5A, 6A, and 7A), and coordinates operation between different sub-modules to effect performance of a particular operation. Although not explicitly shown in FIG. 3A, AP module 304 can include additional sub-modules to monitor different operational parameters and/or control different aspects of system 100. For example, AP module 304 can include a sub-module to generate control signals for sampling devices 154, 155 to periodically obtain aliquots from the retentate and permeate, respectively. In another example, AP module 304 can include a sub-module to generate control signals for injection device 102 to inject a sample at the start of an IVRT experiment. In another example, AP module 304 can include a sub-module to monitor concentrations within the system via signals received from concentration monitoring sensors 186, 188. In some embodiments, AP module 304 can be configured to perform the various functions of each sub-module without sub-modules being specifically delineated therein.

In some embodiments, the controller 156 can interface with the sample analysis system 182. For example, when system 100 and analysis system 182 are part of a common system, controller 156 can coordinate delivery of aliquots obtained using sampling devices 154, 155 to analysis system 182 for subsequent analysis. Alternatively or additionally, controller 156 can control both systems 100 and 182, and controller 156 can include an analysis module separate from the AP module 304 for controlling operation of sample analysis system 182. In another example, controller 156 can be configured to receive data from sample analysis system 182, for example, to display to a user via user interface 306 and/or store in an appropriate data storage device.

In some embodiments, the user interface 306 can be generated by controller 156, for example, using a display and associated input device (e.g., touch screen, mouse, etc.). The user interface 306 enables a user to monitor performance and specify parameters for operation of system 100. For example, FIGS. 4A-4F illustrate various examples of a user interface during different operational modes of an exemplary AP system. Each user interface can include a status bar 402 that indicates the current interface screen and, in some embodiments, can allow a user to change interface screens (and corresponding system operation) by selection of the appropriate button of the status bar 402.

Figure 4A:
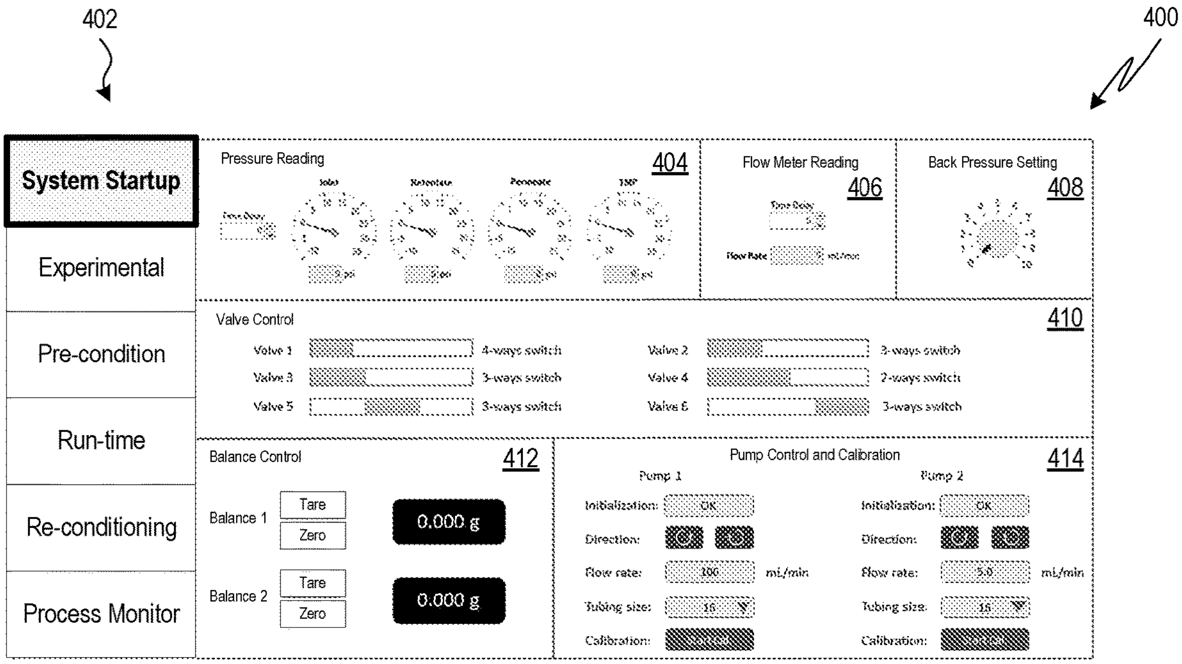
FIGS. 4A-4F show exemplary display interfaces for control of an adaptive perfusion system in various modes of operation.

FIG. 4A illustrates a user interface 400 for "System Startup," which can be displayed to a user to configure or calibrate the system in anticipation of a desired IVRT run. Interface 400 can include various sections 404-414 that allow a user to monitor the current status of the AP system, perform any necessary calibrations, and/or to adjust initial settings in anticipation of an experimental run. Pressure reading section 404 can display measured pressure readings taken by sensors within the AP system (e.g., pressure sensors 136, 138 in system 100 of FIG. 1A) or derived therefrom (e.g., transmembrane pressure). Flow meter reading section 406 can display measured flow rate readings taken by sensors within the AP system (e.g., flux sensor 146 in system 100 of FIG. 1A). Valve control section 410 can display a current position of valves within the AP system (e.g., valves 158, 160, 164, 172 in system 100 of FIG. 1A) and can allow a user to change the valve position to reconfigure the fluid circuit of the AP system. Balance control section 412 can display the weight of the reservoir (e.g., feed reservoir 104, permeate reservoir 144 in system 100 of FIG. 1A) and allow a user to zero (e.g., calibrating the balance) and tare the weight (e.g., to deduct the reservoir mass to obtain sample mass). Pump control and calibration section 414 can be used to define operational characteristics of pumps within the AP system (e.g., pumps 134, 152) and to perform a calibration of the pumps to ensure accurate flow rates.

Figure 4B:
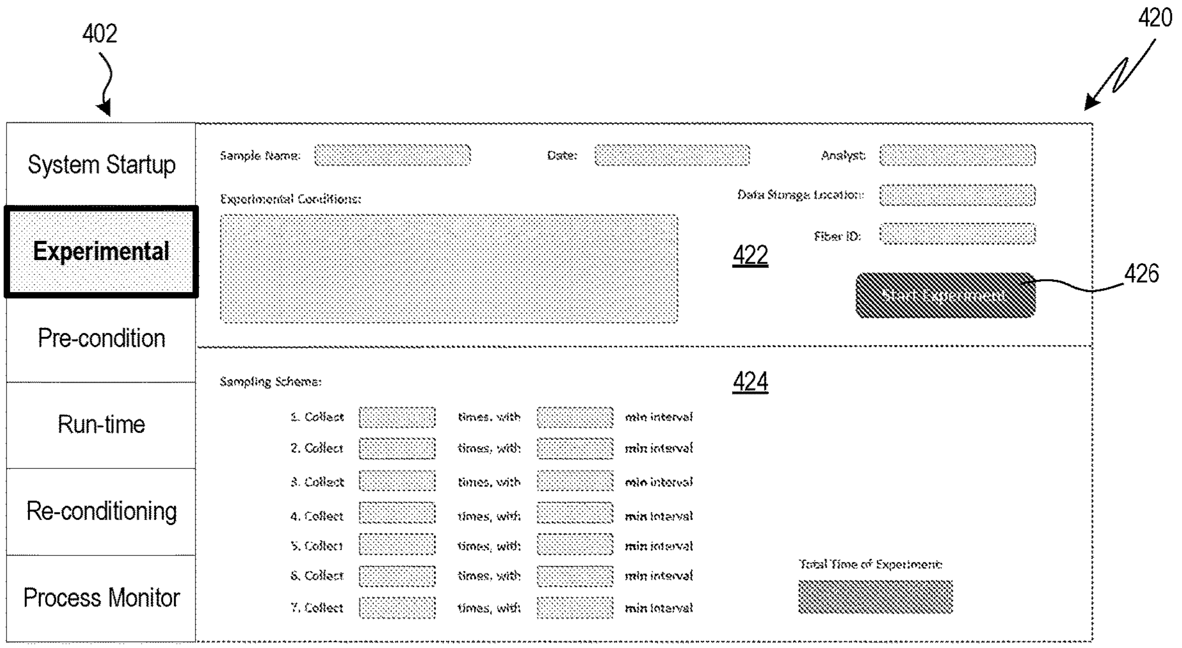

FIG. 4B illustrates a user interface 420 for "Experimental," which can be displayed to a user to define operational parameters of a desired IVRT experiment for a particular drug product sample. Interface 420 can include various sections 422-424 that allow a user to define parameters of the IVRT experiment, and an execution button 426 that causes the AP system to initiate the defined experiment. Section 422 provides fields that allow a user to define bibliographic information of the experiment, while Section 424 provides fields that allow a user to define aliquot collection during the experiment.

Figure 4C:
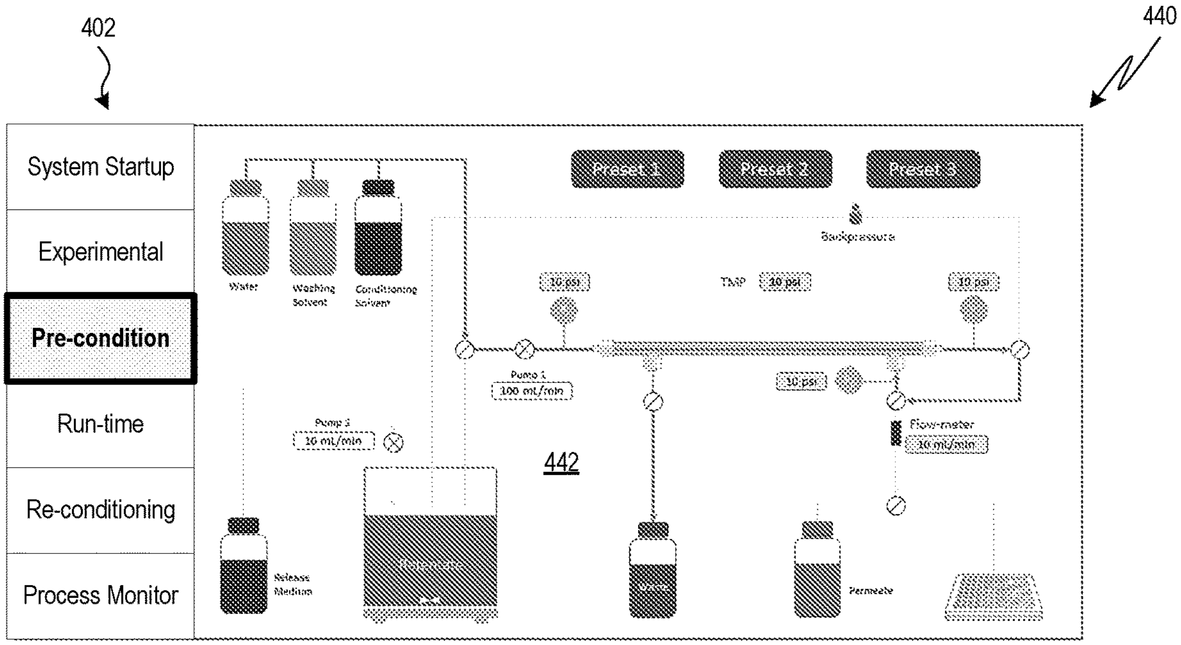

FIG. 4C illustrates a user interface 440 for "Pre-Condition," which can be displayed to a user to show current status of components of the AP system during a pre-conditioning operational mode. In some embodiments, user interface 440 is displayed in response to selection of execution button 426 on the "Experimental" user interface 420. Section 442 can provide a simplified display of the various components of the AP system and their current status during performance of a pre-conditioning operation. User interface 440 can also provide execution buttons that allow a user to select one of the preset protocols for the AP system, which presets may define operation for pre-conditioning to be performed prior to the desired IVRT experiment.

Figure 4D:
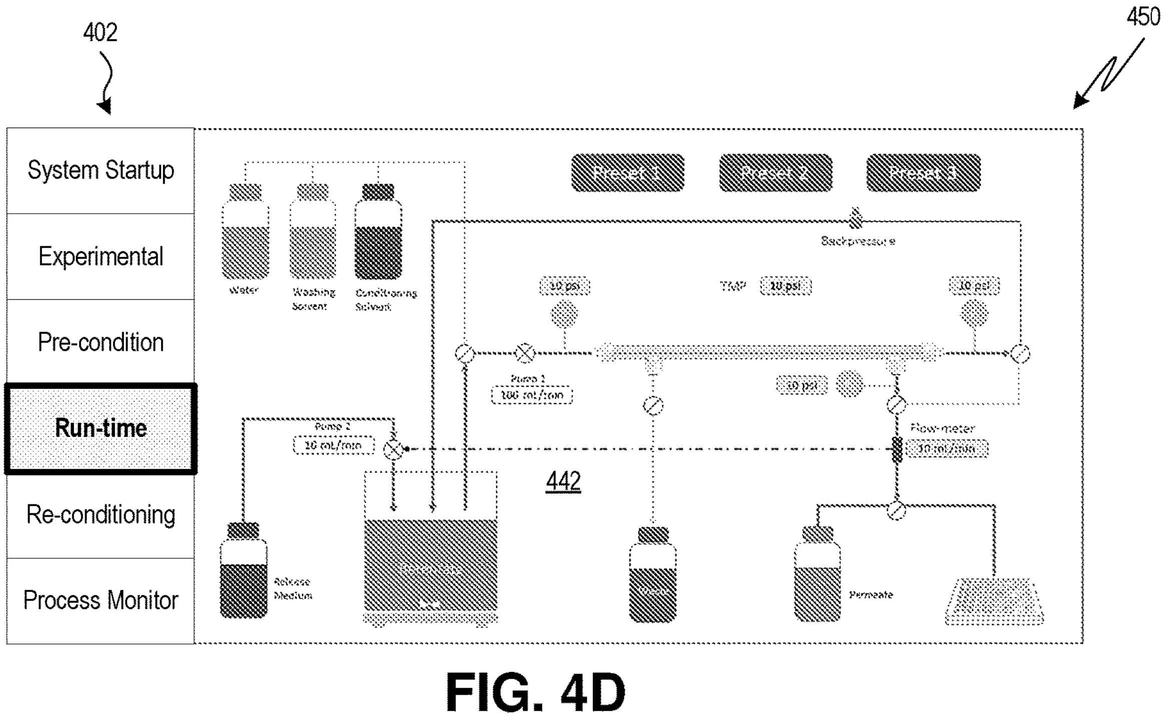

FIG. 4D illustrates a user interface 450 for "Run-Time," which can be displayed to a user to show current status of components of the AP system during an IVRT operational mode. In some embodiments, user interface 450 is displayed automatically in place of user interface 440 at the conclusion of the pre-conditioning operation. In the illustrated example of FIG. 4D, the display in section 442 of various components of the AP system and their current status during performance of the IVRT experiment may be substantially similar to that of user interface 440. User interface 450 can also provide execution buttons that allow a user to select one of the preset protocols for the AP system, which presets may define operation for IVRT runs that are not otherwise defined by the user via user interface 420.

Figure 4E:
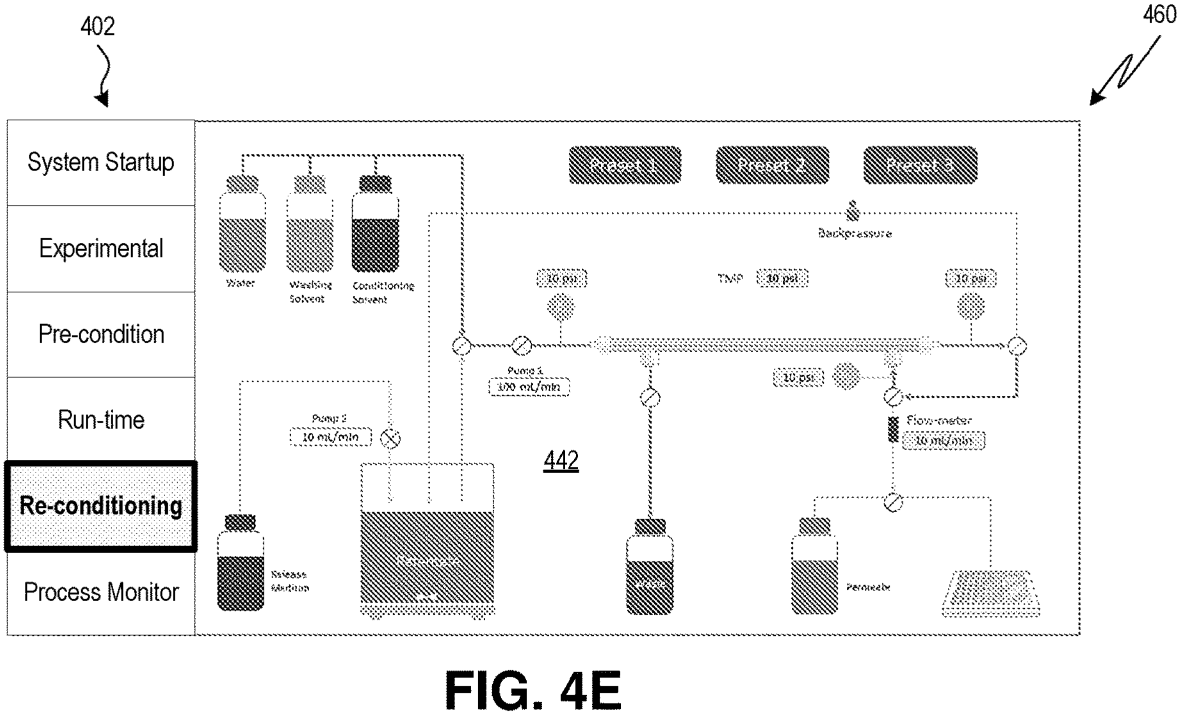

FIG. 4E illustrates a user interface 460 for "Re-Conditioning," which can be displayed to a user to show current status of components of the AP system during a re-conditioning operational mode. In some embodiments, user interface 460 is displayed automatically in place of user interface 450 at the conclusion of the IVRT operation. In the illustrated example of FIG. 4E, the display in section 442 of various components of the AP system and their current status during performance of the re-conditioning may be substantially similar to that of user interface 440. User interface 450 can also provide execution buttons that allow a user to select one of the preset protocols for the AP system, which presets may define operation for re-conditioning to be performed after the IVRT experiment. Alternatively, the presets associated with the execution buttons may define operations for the different modes to be performed in sequence (e.g., pre-conditioning, followed by IVRT, followed by re-conditioning), such that selection of a particular preset on user interface 440 would apply to operations associated with subsequent user interfaces 450, 460.

Figure 4F:
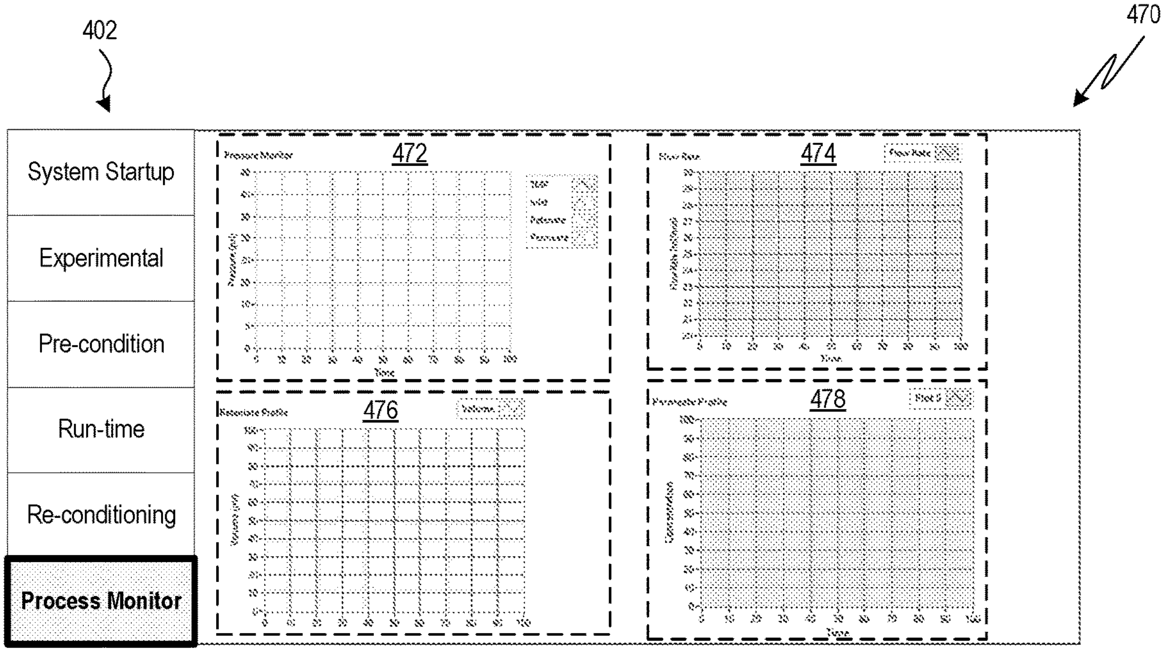

FIG. 4F illustrates a user interface 470 for "Process Monitor," which can be displayed to a user to show data history of various parameters within the AP system during an IVRT operational mode. In some embodiments, user interface 470 is displayed upon user selection from status bar 402 (e.g., during an IVRT experimental run, to show data in real-time) or automatically in place of user interface 460 at the conclusion of re-conditioning. Interface 470 can include various sections 472-478 that graphical display time histories of measured data associated with operation of the AP system. Pressure monitor section 472 displays a graph of pressure measured by sensors within the AP system (e.g., pressure sensors 136, 138 in system 100 of FIG. 1A) or derived therefrom (e.g., transmembrane pressure). Flow rate section 474 displays a graph of flow rate measured by sensors within the AP system (e.g., flux sensor 146 in system 100 of FIG. 1A). Retentate profile section 476 displays a graph of volume for the retentate over time (e.g., within feed reservoir 104), for example, to ensure that a substantially constant volume was maintained during the IVRT. Permeate profile section 478 displays a graph of drug concentration in the permeate flow (e.g., as measured by concentration monitoring sensor 186 in FIG. 1A) over time.

Figure 3B:
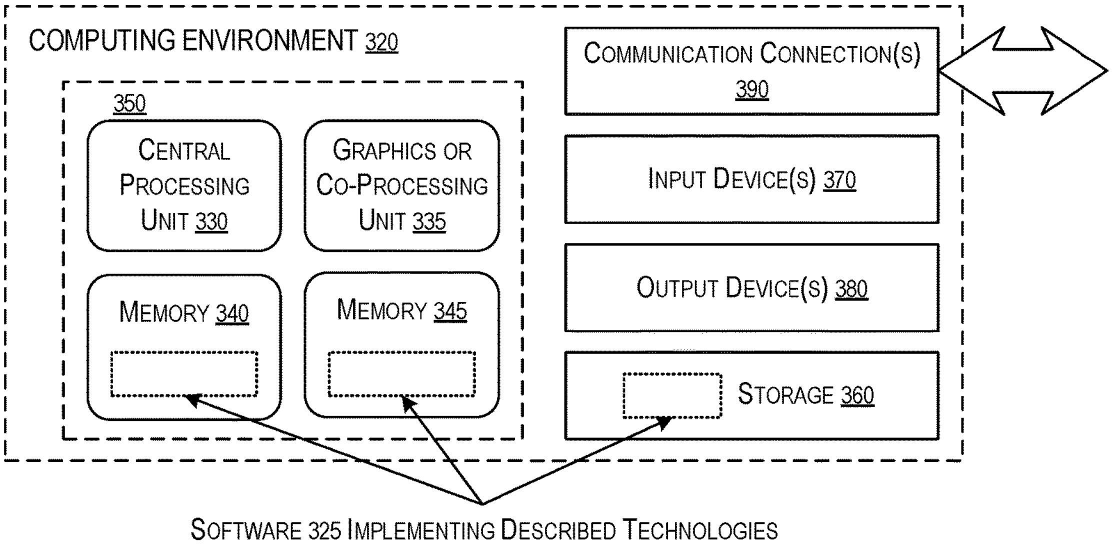
FIG. 3B is a simplified schematic diagram depicting a generalized example of a computing environment in which the disclosed technologies may be implemented.

FIG. 3B depicts a generalized example of a suitable computing environment 320 in which the described innovations may be implemented, such as controller 156. The computing environment 320 is not intended to suggest any limitation as to scope of use or functionality, as the innovations may be implemented in diverse general-purpose or special-purpose computing systems. For example, the computing environment 320 can be any of a variety of computing devices (e.g., desktop computer, laptop computer, server computer, tablet computer, etc.). In some embodiments, the computing environment is part of an adaptive perfusion system. Alternatively, in some embodiments, the computing environment is a separate system connected to the adaptive perfusion system, for example, by making operative electrical connections (e.g., wired or wireless) to the adaptive perfusion system or components thereof.

With reference to FIG. 3B, the computing environment 320 includes one or more processing units 330, 335 and memory 340, 345. In FIG. 3B, this basic configuration 350 is included within a dashed line. The processing units 330, 335 execute computer-executable instructions. A processing unit can be a general-purpose central processing unit (CPU), processor in an application-specific integrated circuit (ASIC) or any other type of processor. In a multi-processing system, multiple processing units execute computer-executable instructions to increase processing power. For example, FIG. 3B shows a central processing unit 330 as well as a graphics processing unit or co-processing unit 335. The tangible memory 340, 345 may be volatile memory (e.g., registers, cache, RAM), non-volatile memory (e.g., ROM, EEPROM, flash memory, etc.), or some combination of the two, accessible by the processing unit(s). The memory 340, 345 stores software 325 implementing one or more innovations described herein, in the form of computer-executable instructions suitable for execution by the processing unit(s).

A computing system may have additional features. For example, the computing environment 320 includes storage 360, one or more input devices 370, one or more output devices 380, and one or more communication connections 390. An interconnection mechanism (not shown) such as a bus, controller, or network interconnects the components of the computing environment 320. Typically, operating system software (not shown) provides an operating environment for other software executing in the computing environment 320, and coordinates activities of the components of the computing environment 320.

The tangible storage 360 may be removable or non-removable, and includes magnetic disks, magnetic tapes or cassettes, CD-ROMs, DVDs, or any other medium which can be used to store information in a non-transitory way, and which can be accessed within the computing environment 320. The storage 360 can store instructions for the software 325 implementing one or more innovations described herein.

The input device(s) 370 may be a touch input device such as a keyboard, mouse, pen, or trackball, a voice input device, a scanning device, or another device that provides input to the computing environment 320. The output device(s) 380 may be a display, printer, speaker, CD-writer, or another device that provides output from computing environment 320.

The communication connection(s) 390 enable communication over a communication medium to another computing entity. The communication medium conveys information such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

Any of the disclosed methods can be implemented as computer-executable instructions stored on one or more computer-readable storage media (e.g., one or more optical media discs, volatile memory components (such as DRAM or SRAM), or non-volatile memory components (such as flash memory or hard drives)) and executed on a computer (e.g., any commercially available computer, including smart phones or other mobile devices that include computing hardware). The term computer-readable storage media does not include communication connections, such as signals and carrier waves. Any of the computer-executable instructions for implementing the disclosed techniques as well as any data created and used during implementation of the disclosed embodiments can be stored on one or more computer-readable storage media. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, aspects of the disclosed technology can be implemented by software written in C++, Java, Perl, any other suitable programming language. Likewise, the disclosed technology is not limited to any particular computer or type of hardware. Certain details of suitable computers and hardware are well known and need not be set forth in detail in this disclosure.

It should also be well understood that any functionality described herein can be performed, at least in part, by one or more hardware logic components, instead of software. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means. In any of the above described examples and embodiments, provision of a request (e.g., data request), indication (e.g., data signal), instruction (e.g., control signal), or any other communication between systems, components, devices, etc. can be by generation and transmission of an appropriate electrical signal by wired or wireless connections.

Method Embodiments

FIG. 5A illustrates an exemplary method 500 for conditioning a TFF filter for subsequent use. In some embodiments, the method 500 may be a pre-conditioning operational mode performed by an AP system, such as AP system 100 of FIG. 1A. Alternatively or additionally, the method 500 may be a pre-conditioning process for preparing a TFF filter for use within an AP system, for example, as TFF filter in AP system 100 of FIG. 1A during the IVRT operational mode thereof. Alternatively, in some embodiments, the method 500 may be used to prepare a TFF filter for use in a drug product manufacturing process, such as for clarification, concentration, purification, and/or solvent or buffer exchange.

The method 500 can initiate at process block 502, where the fluid circuit connected to the TFF filter is set in partial open loop configuration. For example, in AP system 100, valves 158 and 160 can be switched to connect together the outlet 122 (e.g., the retentate outlet) and outlet 120 (e.g., the first permeate outlet), and valve 164 can be switched to connect outlet 124 (e.g., the second permeate outlet) to a waste line or container (e.g., reservoir 168). FIG. 5B shows another example of the partial open loop configuration 520 for HFF 200, where second port 212 is connected to third port 216 via conduit 528, and both the first port 202 and fourth port 218 are opened to allow fluid flow therethrough.

Returning to FIG. 5A, the method 500 can proceed to decision block 504, where the prior use status of the TFF filter is determined. If the TFF filter is a new filter (e.g., delivered from a manufacturer thereof with a storage media, such as glycerin, therein), the method 500 proceeds to process block 506, where the TFF filter in the partial open loop configuration is flushed with a first volume of DI water, without any externally applied backpressure. In some embodiments, the flushing of process block 506 may be considered to be part of a multi-step washing process, for example, to remove the manufacturer's storage media from within the TFF filter. The first volume can be based on a volume of the TFF filter and/or the fluid circuit connected thereto. For example, in some embodiments, the first volume can be at least 10-20 times the volume of the TFF filter. In an exemplary embodiment, the first volume is 2000 mL of DI water for a TFF filter having a volume of 100 mL or less.

To perform process block 506 in AP system 100, a water supply can be connected to an inlet of pump 134 (e.g., using valve 172 or another valve, or by filling feed supply 104 with a volume of DI water), and pump 134 can be operated to direct the DI water into inlet 110 of TFF filter 112. Similarly, to perform process block 506 in the partial open loop configuration 520 for HFF 200 in FIG. 5B, fluid flow 522 can be directed to first port 202 and directed to the individual fibers 206 by the inlet manifold. The fluid flow 524 flows along the retentate side of the membrane of the filter fibers and is collected by outlet manifold. The fluid flow 526 exiting the filter through second port 212 is directed to third port 216 via conduit 528, where it enters the permeate volume of HFF 200. The fluid flow 530 along the permeate side of the membrane of the filter fibers can be in a direction opposite to that of the fluid flow 524 along the retentate side of the membrane of the filter fibers. The permeate-side fluid flow 530 then exits the HFF 200 via fourth port 218, where the fluid can be discarded.

Returning to FIG. 5A, the method 500 can proceed from process block 506 to process block 508, where the TFF filter in the partial open loop configuration is flushed with a second volume of organic solvent, without any externally applied backpressure. In some embodiments, the flushing of process block 508 may be considered to be part of a multi-step washing process to remove the manufacturer's storage media from within the TFF filter. The second volume can be based on a volume of the TFF filter and/or the fluid circuit connected thereto. For example, in some embodiments, the second volume can be at least 5-10 times the volume of the TFF filter. In an exemplary embodiment, the second volume is 1000 mL of ethanol for a TFF filter having a volume of 100 mL or less. The performance of process block 508 for AP system 100 in FIG. 1A or for HFF 200 in the partial open loop configuration 520 of FIG. 5B can otherwise proceed in a manner similar to that described above for process block 506, but with appropriate substitution of an organic solvent as the inlet fluid flow instead of DI water.

The method 500 can proceed from process block 508 to process block 510, where the TFF filter in the partial open loop configuration is flushed with a third volume of DI water, without any externally applied backpressure. In some embodiments, the flushing of process block 510 may be considered to be a rinsing process, for example, to remove any remaining organic solvent from within the TFF filter. The third volume can be based on a volume of the TFF filter and/or the fluid circuit connected thereto. For example, in some embodiments, the third volume can be at least 5-10 times the volume of the TFF filter. In an exemplary embodiment, the third volume is 1000 mL of DI water for a TFF filter having a volume of 100 mL or less. The performance of process block 510 for AP system 100 in FIG. 1A or for HFF 200 in the partial open loop configuration 520 of FIG. 5B can otherwise proceed in a manner similar to that described above for process block 506.

The method 500 can proceed from process block 510 to process block 512, where the TFF filter in the partial open loop configuration is flushed with a fourth volume of conditioning solution, without any externally applied backpressure. In some embodiments, the flushing of process block 512 may be considered to be a conditioning process to prepare the TFF filter for subsequent use. Flushing with conditioning solution in the partial open loop configuration allows both internal surfaces (e.g., retentate side) and external surfaces (e.g., permeate side) of the membrane filter to be conditioned, which can reduce membrane fouling during subsequent use of the TFF filter as compared to flushing in an open loop configuration (e.g., as shown in FIG. 6B). The fourth volume can be based on a volume of the TFF filter and/or the fluid circuit connected thereto. For example, in some embodiments, the fourth volume can be at least 5-10 times the volume of the TFF filter. In an exemplary embodiment, the fourth volume is 1000 mL of conditioning solution for a TFF filter having a volume of 100 mL or less. The conditioning solution can comprise a nonionic surfactant or emulsifier in solution. In an exemplary embodiment, the conditioning solution is 0.07% w/v polysorbate-80 in DI water. The performance of process block 512 for AP system 100 in FIG. 1A or for HFF 200 in the partial open loop configuration 520 of FIG. 5B can otherwise proceed in a manner similar to that described above for process block 506, but with appropriate substitution of a conditioning solution as the inlet fluid flow instead of DI water.

The method 500 can proceed from process block 512 to process block 514, where the TFF filter in the partial open loop configuration is flushed with a fifth volume of DI water, without any externally applied backpressure. In some embodiments, the flushing of process block 514 may be considered to be a rinsing process, for example, to ensure that conditioning solution is fully removed from the TFF filter to avoid adversely impacting IVRT or other subsequent use of the TFF filter. In some embodiments, the flushing of process block 514 may be performed just prior to use of the TFF filter, for example, after calibration of system 100 and before filling the TFF filter with media in performing an IVRT. The fifth volume can be based on a volume of the TFF filter and/or the fluid circuit connected thereto. For example, in some embodiments, the fifth volume can be at least 10-20 times the volume of the TFF filter. In an exemplary embodiment, the fifth volume is 2000 mL of DI water for a TFF filter having a volume of 100 mL or less. The performance of process block 514 for AP system 100 in FIG. 1A or for HFF 200 in the partial open loop configuration 520 of FIG. 5B can otherwise proceed in a manner similar to that described above for process block 506. After process block 514, the method 500 can otherwise proceed to termination block 516, where the TFF filter is ready for further use, for example, at process block 602 of FIG. 6A.

Returning to decision block 504, if the TFF filter is a previously used filter that has been subject to re-conditioning (e.g., as described with respect to FIG. 7A), then performance of one or more of process blocks 506-512 can be omitted. If the TFF filter has been stored in conditioning solution (e.g., 0.07% w/v polysorbate-80 in DI water), then the method 500 proceeds from decision block 504 directly to process block 514. Alternatively, if the TFF filter has been stored in organic solvent (e.g., 10% ethanol in DI water), then the method 500 proceeds from decision block 504 directly to process block 510. It should be appreciated, however, that some or all of process blocks 506-512 may not actually be omitted; rather, some or all of process blocks 506-512 have been effectively moved from method 500 to a re-conditioning process (e.g., method 700 of FIG. 7A), which is performed prior to storage of the TFF filter in conditioning solution.

Although blocks 502-516 of method 500 have been described as being performed once, in some embodiments, multiple repetitions of a particular process block may be employed before proceeding to the next decision block or process block. Moreover, although FIG. 5A illustrate a particular order for blocks 502-516, respectively, embodiments of the disclosed subject matter are not limited thereto. Indeed, in certain embodiments, the blocks may occur in a different order than illustrated or simultaneously with other blocks.

In addition, although FIG. 5B illustrates a particular arrangement and process flow to provide the partial open loop configuration, embodiments of the disclosed subject matter are not limited thereto. For example, in some embodiments, the feed flow can be reversed, with fourth port 218 serving as the inlet and first port 202 serving as the outlet. In another example, in some embodiments, the flow 524 on the retentate side of the hollow fibers 206 can be in a same direction as the flow 530 in the permeate volume 208, for example, by connecting second port 212 to fourth port 218 and connecting third port 216 to a waste line or receptacle. In another variation, the simultaneous fluid flows on opposite sides of the membrane filter can be provided by independent fluid flows, for example, by providing a first fluid flow (e.g., DI water, solvent, or conditioning solution) to first port 202 and directing the fluid from second port 212 to waste, and by simultaneously or sequentially providing a second fluid flow (e.g., DI water, solvent, or conditioning solution) to third port 216 and directing the fluid from fourth port 218 to waste.

FIG. 6A illustrates an exemplary method 600 for IVRT. In some embodiments, the method 600 may be performed by an AP system, such as AP system 100 of FIG. 1A. The method 600 can initiate at process block 602, where the fluid circuit connected to the TFF filter is set in an open loop configuration. For example, in AP system 100, valve 160 can be switched to connect the outlet 122 (e.g., the retentate outlet) to the feed reservoir 132 via a recirculating fluid loop, valve 158 can be switched to connect the outlet 120 (e.g., the first permeate outlet) to permeate reservoir 144, and valve 164 can be switched to a closed position that prevents fluid from exiting from outlet 124 (e.g., the second permeate outlet). FIG. 6B shows another example of an open loop configuration 640 for HFF 200, where second port 212 is connected to feed reservoir 642 via recirculating fluid loop 650 having a backpressure valve 652, the third port 216 is connected to permeate reservoir 656, the first port 202 is connected to feed reservoir 642 via a pump (not shown), and the fourth port 218 is closed by valve 658.

As part of the setup of process block 602, the TFF filter in the open loop configuration can be flushed with a volume of fresh media (e.g., 10 mM pH 7.4 phosphate buffer mixed with ethanol in the ratio of 80:20 v/v), with applied backpressure. In some embodiments, the flushing with fresh media may be considered to be part of a water removal process, for example, to remove any residual DI water remaining from process block 514 of the pre-conditioning method 500. The volume of fresh media can be based on a volume of the TFF filter and/or the fluid circuit connected thereto. For example, in some embodiments, the fresh media volume for flushing can be at least 5 times the volume of the TFF filter. In an exemplary embodiment, the fresh media volume is 500 mL of fresh media for a TFF filter having a volume of 100 mL or less, and the flushing is at a flow rate of 150 mL/min. In some embodiments, rather than returning the fresh media in loop 650 to the feed reservoir 642, the fluid can simply be discarded after back pressure valve 652. Moreover, in some embodiments, after completion of the flushing with fresh media, the fluid conduits connected to the TFF filter can be emptied to remove any residual fluid that may otherwise contribution to sample dilution during subsequent IVRT.

As part of the setup of process block 602, or prior thereto, other components of the system, such as pumps, sensors, etc., can be prepared for use, for example, by initializing (e.g., turning on sensors) and/or performing calibration thereof. For example, tubing calibration can be performed for first pump 134 and second pump 152 to ensure delivery of accurate volumes to TFF filter 112 and feed reservoir 104, respectively. In another example, flux sensor 146 can be calibrated to ensure provision of an accurate permeate flow rate measurement. In some embodiments, the flux sensor calibration can occur at the same time as the fresh media flush.

The method 600 can proceed from process block 602 to process block 604, where a sample of a drug product (e.g., pure drug solution, drug loaded micelles, nanoemulsion, etc.) is provided for IVRT. For example, in AP system 100, a volume of the drug product sample can be spiked into a fixed volume of media in feed reservoir 104 using device 102 or manually. In some embodiments, the feed reservoir can have a stirring mechanism (e.g., a magnetic stirrer) that continuously stirs the contents thereof (e.g., stirred at 1400 rpm). The initial volume of media in the feed reservoir 104 can be selected, for example, based on the dosage form type of the sample, a desired dilution ratio, and/or a desired rate of drug removal (e.g., depending on anticipated drug release characteristics of the sample).

The method 600 can then proceed to process block 606, where an aliquot is obtained to assay for initial drug concentration. In some embodiments, process block 606 may be performed a short time period (e.g., less than 30 seconds, for example, 10 seconds) after introduction of the drug product sample into the media, for example, to allow sufficient time for mixing without the drug product sample otherwise undergoing substantial release. For example, in AP system 100, an aliquot from the feed reservoir 104 can be obtained using sampling device 154 or manually.

The method 600 can then proceed to process block 608, where the AP system is operated to provide IVRT by simultaneous performance of sub-process blocks 610-618. In particular, at sub-process block 610, fluid is pumped from the feed reservoir that initially has the diluted sample therein to a retentate-side inlet of the TFF filter. For example, the feed flow rate to the TFF filter from the feed reservoir can be 200 mL/min. In some embodiments, instead of a continuous feed flow through the filter, a pulsed flow approach could be employed, where the feed flow rate through the filter periodically varies between a maximum value and a minimal or zero value, either in a continuous curve (e.g., sinusoidal, triangular wave, etc.) or step-wise manner, for example, by regulating operation of the peristaltic pumps to increase pulsation effects. Such pulsed flow approaches may further improve filter performance by reducing membrane fouling.

At sub-process block 612, back pressure is applied to the retentate-side outlet of the TFF filter. For example, the back pressure can be adjusted to provide a desired transmembrane pressure for a given feed flow rate. In some embodiments, the feed flow rate and back pressure can be optimized to provide a desired removal rate (e.g., permeate flow rate based on release characteristics of the drug product sample) while ensuring that the inlet pressure to the TFF filter does not exceed specified pressure limits of the TFF filter (e.g., 30 psi). At sub-process block 614, fluid exiting from the retentate-side outlet of the TFF filter is returned to the feed reservoir by way of a recirculating fluid circuit. At sub-process block 616, fluid exiting from the permeate-side outlet of the TFF filter is collected, and a flow rate from the permeate-side outlet can be monitored. At sub-process block 618, fluid is pumped from replacement fluid reservoir to feed reservoir based on the monitored permeate-side flow rate in order maintain a constant volume in the feed reservoir. In some embodiments, fluid can initially be pumped from replacement fluid reservoir to feed reservoir to account for any volume drop in the feed reservoir due to dead volume in the fluid circuit and/or TFF filter. As such, the initial pumping of replacement fluid may be independent of the monitored permeate-side flow rate.

To perform process block 608 in AP system 100, pump 134 can operate to convey media with diluted drug product therein to inlet 110 of TFF filter 112. Back pressure applied via valve 130 to the outlet 122 of TFF filter 112 creates a transmembrane pressure that drives fluid and particles having a molecular weight less than a MWCO of filter membrane from retentate volume 118 to permeate volume 114. The permeate exits TFF filter 112 via outlet 120 to permeate reservoir 144, while flux sensor 146 monitors a rate of flow to the reservoir 144. Pump 152 can operate to convey fresh media from replacement fluid reservoir 148 to feed reservoir 104, using the signal from flux sensor 146 as feedback, to maintain a substantially constant volume in feed reservoir 104.

Similarly, to perform process block 608 in the open loop configuration 640 for HFF 200 in FIG. 6B, fluid flow 644 from feed reservoir 642 can be directed to first port 202 and directed to the individual fibers 206 by the inlet manifold. The fluid flow 646 flow along the retentate side of the membrane of the filter fibers 206 and is collected by outlet manifold. The fluid flow 648 exiting the HFF 200 through second port 212 is returned to the feed reservoir 642 via recirculating loop 650. Back pressure applied via valve 652 to the second port 212 of HFF 200 creates a transmembrane pressure that drives fluids and particles having a molecular weight less than a MWCO of filter fibers 206 through the membrane thereof. The fluid flow 648 thus flows through the permeate volume 208, in a direction substantially parallel to flow 646 in the retentate volume, to third port 216. The permeate 654 exits the HFF via third port 216 and is collected at permeate reservoir 656. Again, the volume of feed reservoir 642 can be kept substantially constant by appropriate addition of fresh media thereto.

Returning to FIG. 6A, the method 600 can proceed from process block 608 to decision block 620, where a timing within the context of the IVRT run is evaluated. In particular, at predetermined time intervals after initiation of the IVRT run, aliquots can be taken from the feed reservoir (e.g., to assay for the drug content remaining therein) and from the permeate flow (e.g., from to assay for the instantaneous drug transfer). The initiation of the IVRT run (e.g., time zero) can be defined as a time during process block 608 when permeate is first observed exiting the TFF filter. If such a time interval has not yet been reached at decision block 620, the method 600 can merely return to process block 608 to continue performance thereof until such time interval is reached.

If a time interval has been reached, the method 600 can proceed from decision block 620 to process block 622, where aliquots are obtained from both the feed reservoir and the permeate flow. For example, in AP system 100, an aliquot from the feed reservoir 104 can be obtained using sampling device 154 or manually, an aliquot from the permeate flow in outlet conduit 142 can be obtained using sampling device 155 or manually. In some embodiments, the obtained aliquots can be sent for immediate analysis, for example, by separate analysis system 182. Alternatively, in some embodiments, the aliquots from different time intervals are accumulated and sent for analysis at the conclusion of the IVRT run. For example, the obtained aliquots can be stored in a microtiter plate, well plate, or any other type of device that can contain multiple aliquots (in an organized arrangement or otherwise) for analysis by liquid chromatography (e.g., high-performance liquid chromatography (HPLC), UPLC, etc.), mass spectrometry, or any other analysis technique (or combination thereof). Alternatively or additionally, in some embodiments, concentrations within fluid in the system can be periodically or continuously monitored in situ. For example, in AP system 100, concentration monitoring sensors 186, 188 can interrogate fluid in the feed reservoir 104 and permeate flow in outlet conduit 142, respectively, in order to determine a concentration of drug therein (or other compositional details). In such embodiments, the obtaining of separate aliquots of process block 622 may be optional.

Once initiated, process block 608 may be performed in a substantially continuous manner until conclusion of the IVRT run, for example, due to expiration of a predetermined time limit or based on a user command. At decision block 620, it can be further evaluated if the time limit for the IVRT run has been reached. If so, the method 600 can proceed from decision block 620 to process block 624, where performance of process block 608 is stopped and final aliquots and measurements are obtained. In some embodiments, both feed pump and replacement fluid pump are stopped at the same time, and the monitoring systems (e.g., pressure and flux sensors) can be turned off or otherwise idled. The fluid conduits connecting the TFF filter to the feed reservoir can be detached from the TFF filter, and fluid therein can be allowed to completely drain into the feed reservoir. In some embodiments, at the end of the IVRT run, an aliquot can be taken from the permeate reservoir and the total volume of permeate can be measured in order to determine the amount of cumulative drug release. The aliquot can be collected for analysis with the other aliquots from performance of process block 622 or can otherwise be separately sent for analysis. The method 600 can thus conclude at 630, subject to any system de-commissioning and/or TFF filter re-conditioning in preparation for subsequent IVRT.

Although blocks 602-624 of method 600 have been described as being performed once, in some embodiments, multiple repetitions of a particular process block may be employed before proceeding to the next decision block or process block. Moreover, although FIG. 6A illustrate a particular order for blocks 602-624, respectively, embodiments of the disclosed subject matter are not limited thereto. Indeed, in certain embodiments, the blocks may occur in a different order than illustrated or simultaneously with other blocks.

FIG. 7A illustrates an exemplary method 700 for conditioning a TFF filter after use. In some embodiments, the method 700 may be a re-conditioning operational mode performed by an AP system, such as AP system 100 of FIG. 1A. Alternatively or additionally, the method 700 may be a re-conditioning process for preparing a recently used TFF filter for use within an AP system, for example, as TFF filter in AP system 100 of FIG. 1A during the IVRT operational mode thereof. Alternatively, in some embodiments, the method 700 may be used to prepare a TFF filter after use in a drug product manufacturing process.

The method 700 can initiate at process block 702, where the fluid circuit connected to the TFF filter is set in the partial open loop configuration. For example, in AP system 100, valves 158 and 160 can be switched to connect together the outlet 122 (e.g., the retentate outlet) and outlet 120 (e.g., the first permeate outlet), and valve 164 can be switched to connect outlet 124 (e.g., the second permeate outlet) to a waste line or container (e.g., reservoir 168). FIG. 5B shows another example of the partial open loop configuration 520 for HFF 200, where second port 212 is connected to third port 216 via conduit 528, and both the first port 202 and fourth port 218 are opened to allow fluid flow therethrough.

Returning to FIG. 7A, the method 700 can proceed to process block 704, where the TFF filter in the partial open loop configuration is flushed with an organic solvent, without any externally applied backpressure. The volume of organic solvent can be based on a volume of the TFF filter and/or the fluid circuit connected thereto. For example, in some embodiments, the volume of organic solvent can be at least 5 times the volume of the TFF filter. In an exemplary embodiment, the volume is 500 mL of ethanol at a flow rate of 100 mL/min, for a TFF filter having a volume of 100 mL or less.

To perform process block 704 in AP system 100, an organic solvent supply can be connected to an inlet of pump 134 (e.g., using valve 172 or another valve, or by replacing the contents feed supply 104 with organic solvent), and pump 134 can be operated to direct the organic solvent into inlet 110 of TFF filter 112. Similarly, to perform process block 704 in the partial open loop configuration 520 for HFF 200 in FIG. 5B, fluid flow 522 can be directed to first port 202 and directed to the individual fibers 206 by the inlet manifold. The fluid flow 524 flows along the retentate side of the membrane of the filter fibers and is collected by outlet manifold. The fluid flow 526 exiting the filter through second port 212 is directed to third port 216 via conduit 528, where it enters the permeate volume of HFF 200. The fluid flow 530 along the permeate side of the membrane of the filter fibers can be in a direction opposite to that of the fluid flow 524 along the retentate side of the membrane of the filter fibers. The permeate-side fluid flow 530 then exits the HFF 200 via fourth port 218.

Returning to FIG. 7A, at decision block 706, it can be determined whether mass recovery is desired during the flushing of process block 704. Mass recovery of the drug sample by washing the membrane filter of the TFF filter using a solvent can allow for better accounting of all of the drug product in the system. In particular, while the permeate reservoir provides a measure of the drug product that was released to the permeate and the feed reservoir provides a measure of the drug product remaining in the retentate, the mass recovery offers a measure of the drug product that was caught within the filter and that might otherwise have been lost to the analysis. If mass recovery is desired at decision block 704, the method 700 can proceed to process block 708, where the fluid from the permeate side outlet in the partial open loop configuration during performance of process block 704 is collected. For example, in AP system 100, the organic solvent exiting third outlet 124 can be collected in reservoir 168. In the example of FIG. 5B, the permeate-side fluid flow 530 that exits the HFF 200 via fourth port 218 can be directed to a reservoir for collection (e.g., similar to solvent reservoir 754 in FIG. 7B). Instead, if mass recovery is not desired at decision block 704, the method can proceed to process block 710, where the fluid exiting the permeate side of the TFF filter is simply discarded.

The method 700 can then proceed from either process block 708 or process block 710 to process block 712, where the fluid circuit connected to the TFF filter is set in a closed loop configuration. For example, in AP system 100, valves 158 and 160 can maintain their configuration that connect the outlet 122 (e.g., the retentate outlet) and outlet 120 (e.g., the first permeate outlet) together, and valves 164 and 170 can be switched to connect inlet 110 (e.g., the feed inlet) and outlet 124 (e.g., the second permeate outlet) to a common reservoir 168. FIG. 7B shows another example of the closed loop configuration 740 for HFF 200, where second port 212 is connected to third port 216 via conduit 748, and first port 202 and fourth port 218 are connected to a common reservoir 754 via conduit 756.

Returning to FIG. 7A, the method 700 can proceed to process block 714, where the TFF filter in the closed loop configuration is flushed with an organic solvent, without any externally applied backpressure. The volume of organic solvent can be based on a volume of the TFF filter and/or the fluid circuit connected thereto. For example, in some embodiments, the volume of organic solvent can be at least 5 times the volume of the TFF filter. In an exemplary embodiment, for a TFF filter having a volume of 100 mL or less, the volume is 500 mL of ethanol at a flow rate of 100 mL/min for at least 15 minutes.

To perform process block 714 in AP system 100, solvent reservoir 168 can be filled with the desired volume of organic solvent, which reservoir 168 is connected to an inlet of pump 134 via valve 172. Pump 134 can then be operated to direct the organic solvent from reservoir into inlet 110 of TFF filter 112. Similarly, to perform process block 714 in the closed loop configuration 740 for HFF 200 in FIG. 7B, fluid flow 742 can be directed to first port 202 from solvent reservoir 754 and directed to the individual fibers 206 by the inlet manifold. The solvent flow 744 flows along the retentate side of the membrane of the filter fibers and is collected by outlet manifold. The solvent flow 746 exiting the filter through second port 212 is directed to third port 216 via conduit 748, where it enters the permeate volume of HFF 200. The solvent flow 750 along the permeate side of the membrane of the filter fibers can be in a direction opposite to that of the solvent flow 744 along the retentate side of the membrane of the filter fibers. The permeate-side fluid flow 752 then exits the HFF 200 via fourth port 218 and is directed to solvent reservoir 754 for recirculation via conduit 756.

Returning to FIG. 7A, the method 700 can proceed to process block 716, where the fluid circuit connected to the TFF filter is again set in the partial open loop configuration, for example, in a manner similar to that described above for process block 702. The method 700 can proceed to decision block 730, where appropriate storage conditions are determined based on expected next use for the TFF filter. If the TFF filter will be re-used for testing or other filtration application within 24 hours, the method 700 can proceed from decision block 730 to process block 718. At process block 718, the TFF filter in the partial open loop configuration is first rinsed with DI water and then flushed with conditioning solution, for example, in a manner similar to that described above for process blocks 510 and 512, respectively in FIG. 5A. For example, the TFF filter in the partial open loop configuration can first be flushed with 1000 mL of DI water, and then flushed with 1000 mL of conditioning solution (e.g., 0.07% w/v polysorbate-80 in DI water). The method 700 can then proceed to process block 720, where the re-conditioned TFF filter is removed from the setup and disposed in conditioning solution for storage. The method 700 can otherwise proceed to termination block 722, where the TFF filter is stored for up to 24 hours in the conditioning solution ready for reuse, which can be initiated, for example, by rinsing at process block 514 of FIG. 5A.

Returning to decision block 730, if the TFF filter will not be used within 24 hours, the method 700 can proceed to process block 724, where the TFF filter in the partial open loop configuration is flushed with diluted organic solvent, for example, in a manner similar to that described above for process block 508 in FIG. 5A. Optionally, prior to the flush with diluted organic solvent, the TFF filter in the partial open loop configuration can be rinsed with DI water, for example, in a manner similar to that described above for process block 510 in FIG. 5A. For example, the TFF filter in the partial open loop configuration can be flushed with 1000 mL of diluted organic solvent (e.g., 10% ethanol in DI water). The method 700 can then proceed to process block 726, where the TFF filter is removed from the setup and disposed in diluted organic solvent for storage. The method 700 can otherwise proceed to termination block 728, where the TFF filter is stored for more than 24 hours (e.g., but not more than 5 days) in the diluted organic solvent ready to undergo conditioning again, which can be initiated, for example, by rinsing at process block 510 of FIG. 5A.

Although blocks 702-730 of method 700 have been described as being performed once, in some embodiments, multiple repetitions of a particular process block may be employed before proceeding to the next decision block or process block. Moreover, although FIG. 7A illustrate a particular order for blocks 702-730, respectively, embodiments of the disclosed subject matter are not limited thereto. Indeed, in certain embodiments, the blocks may occur in a different order than illustrated or simultaneously with other blocks.

In addition, although FIG. 7B illustrates a particular arrangement and process flow to provide the closed loop configuration, embodiments of the disclosed subject matter are not limited thereto. For example, in some embodiments, the feed flow can be reversed, with fourth port 218 serving as the inlet and first port 202 serving as the outlet. In another example, in some embodiments, the flow 744 on the retentate side of the hollow fibers 206 can be in a same direction as the flow 750 in the permeate volume 208, for example, by connecting second port 212 to the solvent reservoir 754 and connecting third port 216 to first port 202. In another variation, the simultaneous fluid flows on opposite sides of the membrane filter can be provided by independent fluid flows, for example, by providing a first fluid flow (e.g., solvent) to first port 202 and directing the fluid from second port 212 to waste, and by simultaneously or sequentially providing a second fluid flow (e.g., solvent) to third port 216 and directing the fluid from fourth port 218 to waste.

EXAMPLES

General Information for Examples

Materials: Difluprednate (>97%) was purchased from RIA International LLC (East Hanover, NJ). Castor oil was purchased from Fisher (Pittsburgh, PA). Polysorbate-80 was purchased from Acros Organics (Morris Plains, NJ). Glycerin, sodium acetate, boric acid, edetate disodium and sodium dodecyl sulfate were purchased from Fisher Scientific (Waltham, MA). Sorbic acid was obtained from MP Biomedicals (Solon, OH). Sodium dihydrogen phosphate and sodium hydroxide (1N and 2N) was purchased from Sigma Aldrich (St. Louis, MO). Phosphoric acid was obtained from EMD Millipore Corporation (Burlington, MA). Acetonitrile was obtained from Fisher Scientific (Waltham, MA). Ethanol was procured from Decon Labs (King of Prussia, PA). Deionized water was obtained from Milli-Q Ultrapure Water Systems, EMD Millipore Corporation (Burlington, MA). Unless otherwise specified, all materials were of analytical grade.

Preparation of drug loaded micelles: Difluprednate micelles were prepared by dispersing and sonicating difluprednate powder in 3.6% w/v polysorbate-80 solution in deionized water at room temperature. The final concentration of difluprednate in the polysorbate-80 micelles was determined to be about 100 μg/mL, by ultra-performance liquid chromatography (UPLC) method (Method 1).

Preparation of nanoemulsions: Three nanoemulsions with different globule size distributions were manufactured by microfluidization process, while keeping their composition qualitatively (Q1) and quantitatively (Q2) the same as the reference listed drug, Durezol®. Briefly, primary emulsion was formed by high-shear mixing of the aqueous phase-I (containing a mixture of glycerin, polysorbate-80, and deionized water) with the oil phase (castor oil containing difluprednate) by maintaining the temperature at 65°-70° C. Primary emulsion was further mixed with the aqueous phase-II (containing sorbic acid, sodium acetate, boric acid and edetate disodium dissolved in deionized water) maintained at 65°-70° C. to obtain a coarse emulsion. pH of the coarse emulsion was then adjusted to 5.2 to 5.8 at room temperature by using 1N sodium hydroxide. Thereafter, the coarse emulsion was subjected to microfluidization process, with precise control over the variation of critical process parameters (CPPs) such as pressure and temperature. These variations in CPPs of microfluidization process produced nanoemulsions with small (approximately 80 nm mean size), medium (approximately 120 nm mean size) and large (approximately 150 nm mean size) globule size distributions. The globule size distribution of the nanoemulsions was determined by dynamic light scattering method using Zetasizer Nano ZSP instrument (Malvern Panalytical Inc., Westborough, MA). The results of Z-average, polydispersity index (PdI) and intensity weighed distribution ($D_{10}$, $D_{50}$ and $D_{90}$) for each formulation is provided in Table 1.

TABLE 1

Globule size distribution data for difluprednate nanoemulsions (Mean ± SD, n = 3)

| Sample GSD Nanoemulsion | Z-Average (d · nm) | PdI | Di(10) (nm) | Di(50) (nm) | Di(90) (nm) |
|---|---|---|---|---|---|
| Large | 152.4 ± 1.3 | 0.181 ± 0.014 | 94.1 ± 6.2 | 171.1 ± 3.9 | 305.6 ± 18.8 |
| Medium | 121.9 ± 0.9 | 0.203 ± 0.010 | 70.3 ± 2.8 | 140.0 ± 2.9 | 261.8 ± 13.5 |
| Small | 78.5 ± 0.6 | 0.206 ± 0.008 | 44.1 ± 0.9 | 87.2 ± 2.1 | 181.0 ± 12.6 |

Ultra performance liquid chromatography: The UPLC system included a Waters Acquity UPLC I-Class (Waters Corporation, Milford, MA) equipped with degasser, binary solvent pump, thermostatted autosampler, thermostatted column compartment, and a photo diode array detector. Acquity UPLC BEH C18, 2.1 mm×150 mm (1.7 μm packing) column (Waters Corporation, Milford, MA) was used along with an Acquity UPLC BEH C18, 2.1 mm×5 mm (1.7 μm packing) vanguard precolumn (Waters Corporation, Milford, MA). Column temperature was maintained at 50° C. whereas autosampler temperature was kept at 8° C. A 100 μL extension loop was used. Two separate gradient elution methods (Method 1 in Table 2 and Method 2 in Table 3) were used to analyze difluprednate in different media, e.g., Method 1 for retentate samples, and Method 2 for permeate samples. Injection volume was 3 μL and 80 μL for Method 1 and Method 2, respectively. The eluted difluprednate was detected at 240 nm. Data collection and analysis were performed using Empower 3 software.

TABLE 2

UPLC gradient elution method (Method 1) for the determination of difluprednate concentration

| Time (min) | Flow rate (mL/min) | % Deionized Water, pH 2.5 (pH adjusted with phosphoric acid) | % Acetonitrile |
|---|---|---|---|
| 0.0 | 0.45 | 50 | 50 |
| 5.0 | 0.45 | 50 | 50 |
| 6.0 | 0.45 | 0 | 100 |
| 11.0 | 0.45 | 0 | 100 |
| 12.0 | 0.45 | 50 | 50 |
| 17.0 | 0.45 | 50 | 50 |

TABLE 3

UPLC gradient elution method (Method 2) for the determination of difluprednate concentration

| Time (min) | Flow rate (mL/min) | % Deionized Water, pH 2.5 (pH adjusted with phosphoric acid) | % Acetonitrile |
|---|---|---|---|
| 0.0 | 0.50 | 40 | 60 |
| 2.5 | 0.50 | 40 | 60 |
| 3.5 | 0.50 | 0 | 100 |
| 10.0 | 0.50 | 0 | 100 |
| 11.0 | 0.50 | 40 | 60 |
| 15.0 | 0.50 | 40 | 60 |

Comparative Example 1—Pure Drug Solution

Figure 8A:
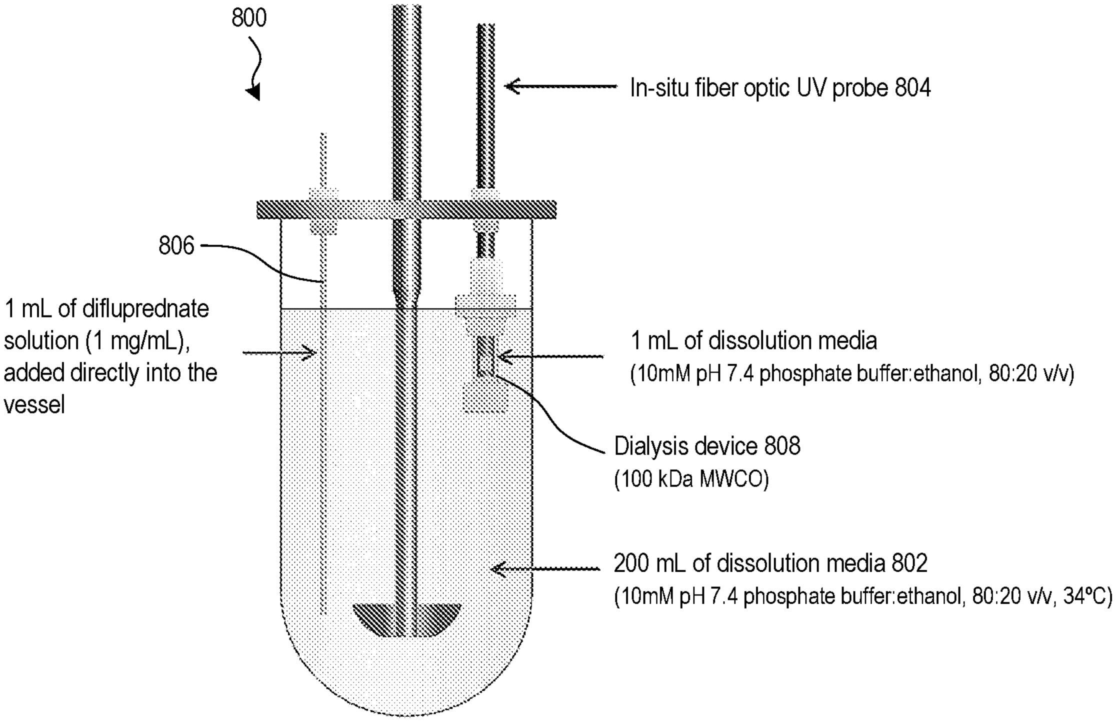
FIG. 8A is a schematic representation of an in vitro release setup involving reverse-dialysis that was used for comparative testing of pure drug solutions.

Release of difluprednate from pure drug solution was studied using a reverse-dialysis setup, where drug was transferred from outside a dialysis device to the inside. As compared to a dialysis configuration, the reverse-dialysis configuration provides an advantage in terms of allowing for better control of dilution and maximum drug concentration gradient across oil/water interface to drive the drug release. Diffusion of difluprednate through dialysis membrane was determined in a USP 2 apparatus setup (Vision Elite 8, Teledyne Hanson Research, with mini-vessels 800) using commercially available dialysis tubes 808 (Float-A-Lyzer G2, 100 kD MWCO, regenerated cellulose, Spectrum Labs, CA, USA), as shown in FIG. 8A. Each dialysis tube 808 was cleaned with 1.0% w/v polysorbate-80 solution in deionized water and subsequently washed thoroughly with deionized water. Dialysis tubes 808, containing about 1 mL of the release media (i.e., 10 mM pH 7.4 phosphate buffer mixed with ethanol in the ratio of 80:20 v/v), were suspended inside the USP 2 mini-vessels 800. Agitation was controlled at 100 rpm and the temperature was maintained at 34° C. Using conduit 806, 1 mL of difluprednate solution (1 mg/mL in ethanol) was spiked directly into the vessel 800, which contained 200 mL release media 802, in order to achieve an initial drug concentration of 5 μg/mL.

Within dialysis tube 808, difluprednate concentration (e.g., drug that had diffused through the membrane filter of dialysis device 808) was monitored in real time using an in-situ fiber optic probe 804, in particular a fiber optic UV-Vis system (Pion μDiss Profiler™, Billerica, MA). The scanning frequency was once every minute for the first 6 hours, then it switched to once every 5 minutes for the next 18 hours. After first 24 hours, the scanning frequency was changed to once every 10 minutes for the next 40 hours. For the last 104 hours, the scanning frequency was once every 30 min. The total experimental time was 168 hours (7 days). Pure difluprednate solution diluted with release medium at the same concentration of 5 μg/mL was also monitored in parallel as a control to determine any possible change in drug concentration, e.g., due to degradation. Prior to the start of the experiment, UV signals were calibrated using various concentrations of difluprednate standard solutions (0.05, 0.10, 0.50, 1.00, 2.00, 3.00, 4.00, and 6.00 μg/mL). Zero Intercept Method (ZIM) analysis was performed to remove polysorbate-80 interference by using wavelength within the range of 271-274 nm (exact ZIM wavelength varied between probes). Ethanol was used as a co-solvent to prevent the precipitation of difluprednate in the release media.

Figure 8B:
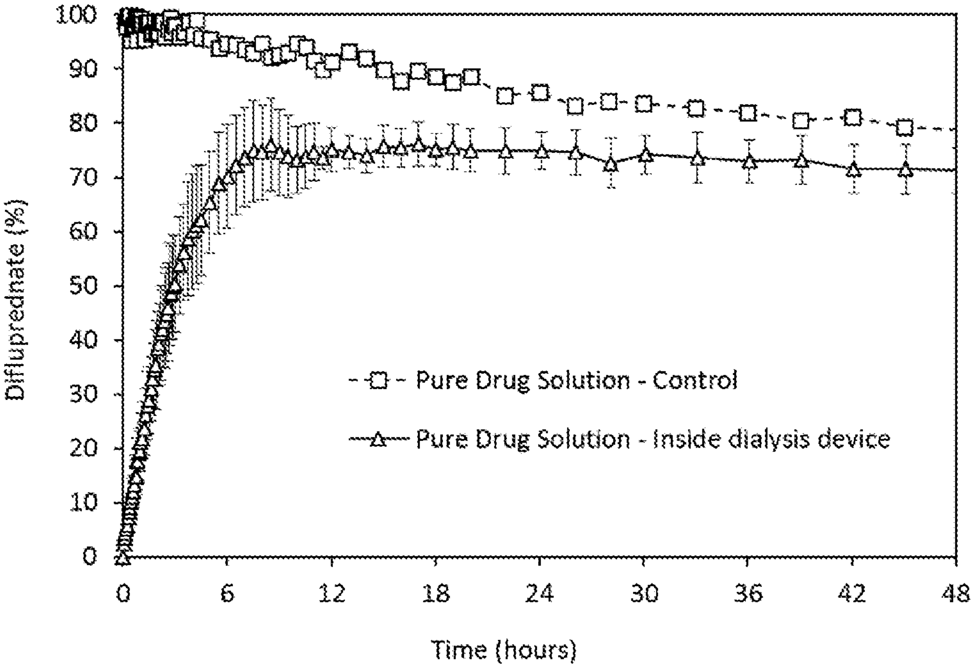
FIG. 8B is a graph of release profiles (percentage released versus time) of the pure drug solution in the setup of FIG. 8A as compared to a control sample of the pure drug solution.

FIG. 8B is a graphical representation of the release profile of pure drug solution tested using reverse-dialysis method. The square markers with dashed lines depict the difluprednate degradation in the control sample (Mean±SD, n=3 for release test and n=1 for control sample). As seen in FIG. 8B, in the case of pure drug diffusion, it took more than 3 hours for 50% of difluprednate to diffuse across the dialysis membrane (100 kD MWCO) and nearly 8 hours for the difluprednate concentration to reach plateau (about 75% of the drug diffused). The slow diffusion of difluprednate across the dialysis membrane is attributed to its lipophilicity and potential interaction with the dialysis membrane and is very likely to become a rate-limiting step for drug release. Furthermore, a decrease in difluprednate concentration was observed after about 10 hours, which was confirmed to be a result of difluprednate degradation in alkaline media. This is evident from the control sample (i.e., direct analysis of difluprednate in solution), where a continuing decay in difluprednate concentration was observed, with only 85% of the pure drug remaining in the bulk media at 24 hrs.

Comparative Example 2—Nanoemulsion

Figure 9A:
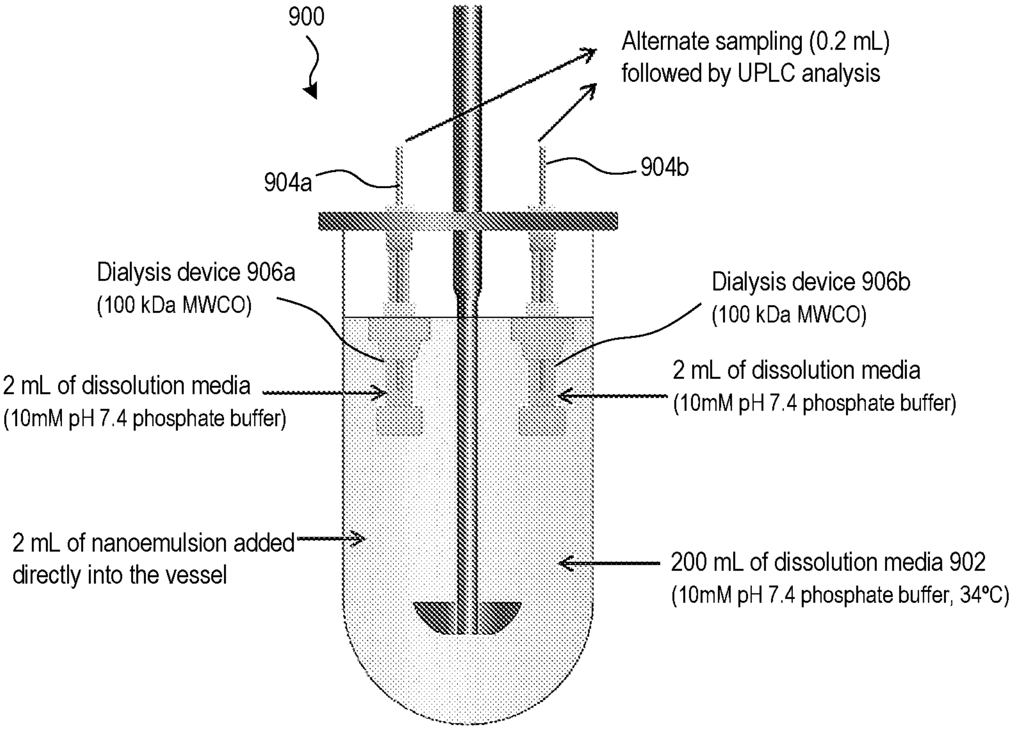
FIG. 9A is a schematic representation of another in vitro release setup involving reverse-dialysis that was used for comparative testing of nanoemulsions.

Release of difluprednate from nanoemulsions was studied using a reverse-dialysis setup, where drug was transferred from outside a dialysis device to the inside. As compared to a dialysis configuration, the reverse-dialysis configuration provides an advantage in terms of allowing for better control of dilution and maximum drug concentration gradient across oil/water interface to drive the drug release. The IVRT study was performed by using a reverse dialysis setup inside a USP 2 apparatus equipped with mini-vessels 900, as shown in FIG. 9A. Evaluated samples included nanoemulsions of two different globule size distributions, in particular, small and large. Each dialysis tube 906*a*, 906*b* was cleaned with 1.0% w/v polysorbate-80 solution in deionized water and subsequently washed thoroughly with deionized water. Agitation was controlled at 100 rpm and the temperature was maintained at 34° C. Two dialysis tubes 906*a*, 906*b* (Float-A-Lyzer G2, 100 kD MWCO, regenerated cellulose, Spectrum Labs, CA, USA), each containing 2 mL of fresh release media (i.e., 10 mM pH 7.4 phosphate buffer), were suspended using an adapter inside each mini-vessel 900.

Into mini-vessel 900, 2 mL of nanoemulsion was added directly to 200 mL release media 902 in order to achieve an initial concentration of 5 μg/mL for difluprednate. Sampling was performed from alternating dialysis tubes 906*a*, 906*b*. At each pre-determined sampling time point, 0.2 mL of media was taken from both inside the dialysis tubes (e.g., using respective conduits 904*a*, 904*b*) and the outside media 902. Due to the interference of other formulation components, in-situ UV analysis was not possible, and accordingly difluprednate concentration was determined by UPLC method (e.g., Method 2). An equivalent volume of fresh media was replenished inside the dialysis tubes 906*a*, 906*b* after each sampling.

Figure 9B:
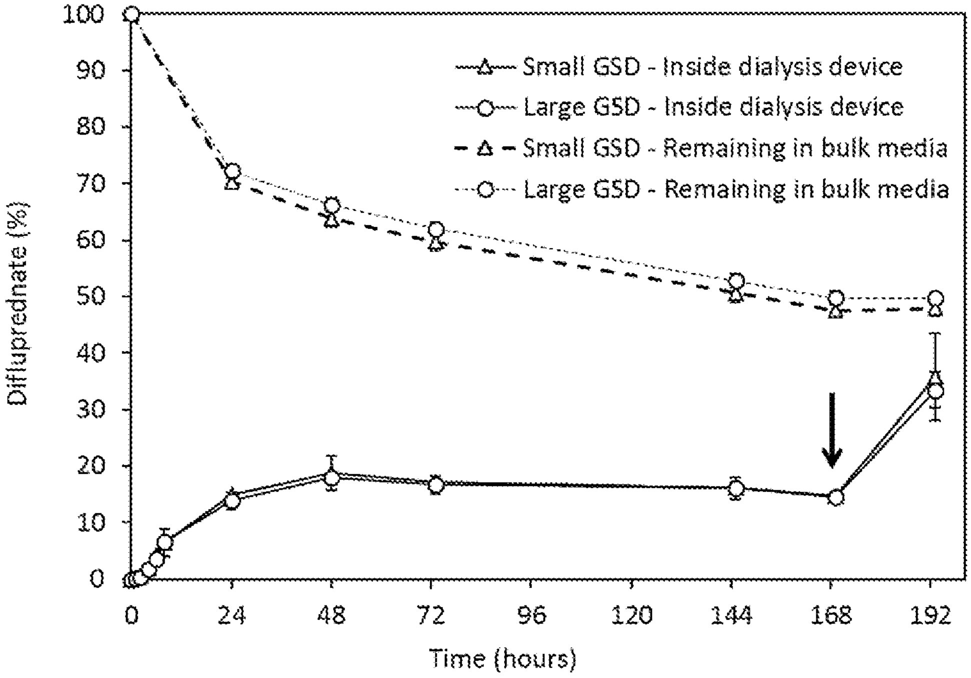
FIG. 9B is a graph of release profiles (percentage released versus time) as well as retention profiles (percentage remaining in bulk media versus time) for large globule size distribution (GSD) nanoemulsions and small GSD nanoemulsions.

FIG. 9B is a graphical representation of the in vitro drug release profiles for large and small globule size nanoemulsions tested using reverse-dialysis method of FIG. 9A. The circle and triangle markers with dashed lines depict the difluprednate degradation occurring in the bulk media during reverse dialysis for large and small globule size nanoemulsions respectively. The circle and triangle markers with bold lines represent the percentage of difluprednate diffused inside the dialysis tubes 906*a*, 906*b* for large and small globule size nanoemulsions respectively (Mean±SD, n=3). The downward arrow represents the timepoint at which sodium dodecyl sulfate (SDS) is spiked in the bulk media 902 during the in vitro release studies.

As shown in FIG. 9B, the two formulations exhibited similar drug release profiles, despite the significant differences in their globule sizes (e.g., z-average of 80 nm vs. 150 nm). Furthermore, the drug release from both the emulsions was slow and incomplete, taking more than 48 hours to reach a plateau of about 18% drug release. To verify the mass balance, SDS was spiked in the external media 902 at 168 hours at a concentration of 0.05% w/v. This led to an increase in drug concentration inside the dialysis device resulting from drug release from the emulsions. At 192 hours, the total detected drug inside the dialysis device 906*a*, 906*b* was 33.45% and 35.80% for large and small emulsions, respectively, while the outside drug percentage (e.g., in media 902) was 49.69% and 47.96% for large and small emulsions, respectively. As such, the total drug amount recovered by the end of the 192 hour experiment were 83.14% and 83.76% for large and small emulsions, respectively. The remaining drug was suspected to be lost due to degradation from prolonged exposure to alkaline pH of the media.

In summary, despite the high dilution ratio (100 time dilution by release medium), aggressive agitation (100 rpm), and elevated temperature (34° C.), all of the conditions favoring the drug release from emulsions, the rate and extent of drug release was still slow and low, rendering reverse-dialysis method incapable of discerning differences in the drug release profiles of the small and large globule size nanoemulsions.

Example 1—Adaptive Perfusion Setup

Figure 10:
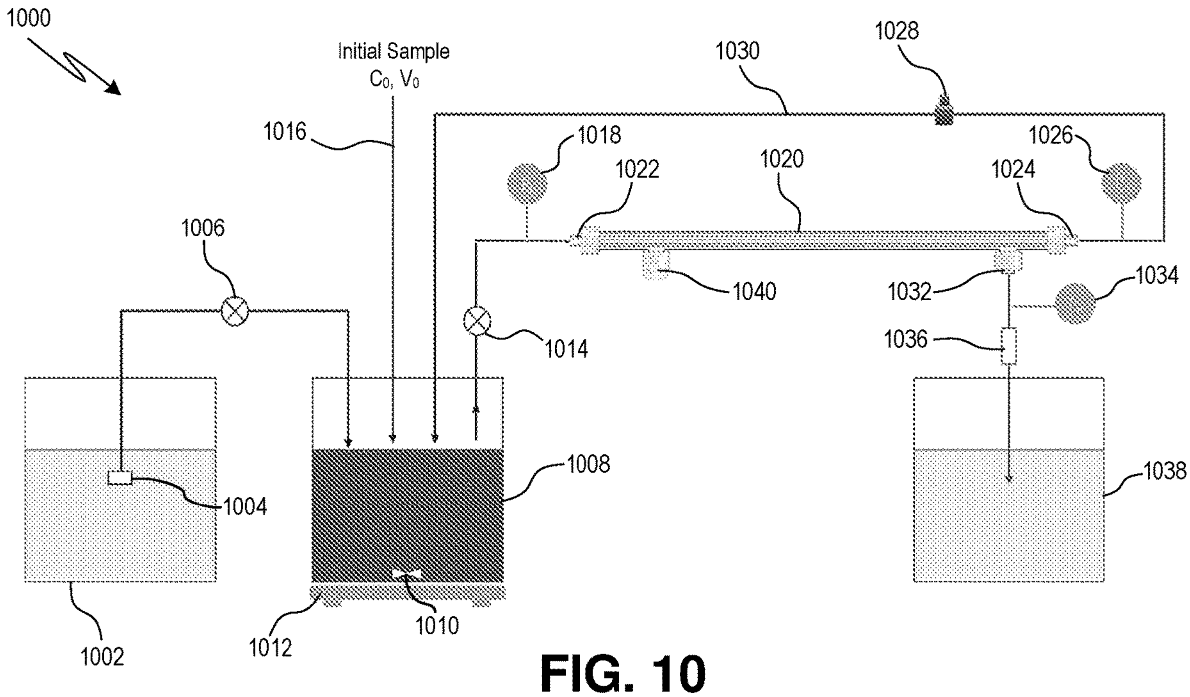
FIG. 10 is a simplified schematic diagram illustrating aspects of a fabricated adaptive perfusion setup for drug release testing.

FIG. 10 shows a setup 1000 for AP that was employed in the following experimental examples. The setup 1000 includes a fresh media reservoir 1002, a particulate filtering device 1004 attached to the fresh media tubing (to prevent particulate contamination), two peristaltic pumps (a first pump 1014 for the sample feed and a second pump 1006 for the fresh media), two additional reservoirs (a first reservoir 1008 for the retentate (also called the feed reservoir) and a second reservoir 1038 for the permeate (also called the permeate reservoir)), a pre-conditioned TFF filter (in particular, an HFF 1020, with first port 1022 and second port 1024 connected to a retentate volume and third port 1032 and fourth port 1040 connected to a permeate volume), a backpressure controlling valve 1028, a magnetic stirrer 1010, a stir plate 1012 for mixing the sample with the media, a pressure monitoring system with three pressure sensors (inlet sensor 1018, retentate sensor 1026, and permeate sensor 1034), a mass flow monitoring system (e.g., flowmeter 1036), a data acquisition system (e.g., computer with software), and a fluid circuit 1030 (e.g., tubing) for interconnecting the various components. HFF 1020 was a Spectrum MicroKros®, 100 kD MWCO, modified polyether sulfone (mPES) membrane, 20 $cm^2$ surface area (Repligen Corporation, CA, USA). An initial drug product sample of a particular concentration and/or volume was manually spiked into the first reservoir 1008 using conduit 1016.

Example 2—Selective Retention of Castor Oil

AP setup 1000 provided a unique platform for in vitro release testing of various complex dosage forms. The adaptive nature of the process allows the user to optimize the feed flow rate based on the type of dosage form. For example, higher flow rate may be selected to quickly remove the released drug in case of rapid release from formulations (e.g., micelle phase within emulsions which readily releases the drug within few minutes). Likewise, for formulations with multiphasic release kinetics, flow rate may be adjusted during the experiment to adjust the rate of drug removal. Even though the sample is circulated in a closed loop (e.g., from reservoir 1008 to first port 1022 of HFF 1020 and from second port 1024 of HFF 1020 back to the reservoir 1008), the simultaneous size-based separation (e.g., via HFF 1020) and the concurrent dilution of sample (e.g., via fluid from reservoir 1002 into feed reservoir 1008) helps in overcoming the limitation due to small medium volume in maintaining continuous sink conditions.

Figure 11:
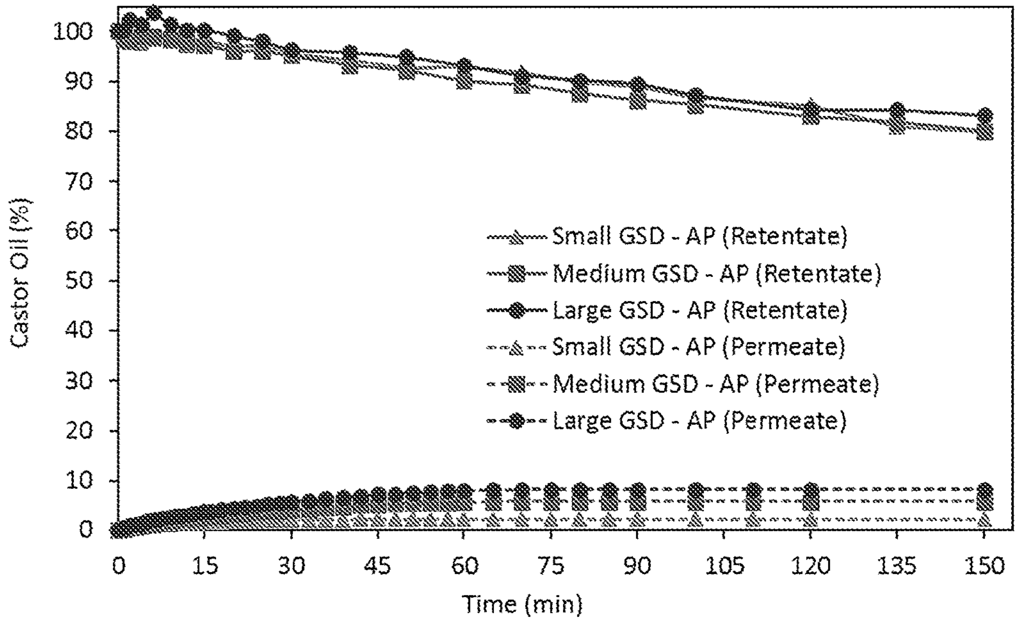
FIG. 11 is a graph of selective retention of oil globules (e.g., castor oil) for various GSD nanoemulsions in the adaptive perfusion setup of FIG. 10.

Formulation components can be selectively retained based on the MWCO range of the membrane filter of the HFF 1020. For example, castor oil globules in the nanoemulsions or protein-bound drug containing nanoparticles can be selectively retained and made to continuously circulate in fluid circuit 1030, which is being continuously diluted with fresh medium (e.g., via fluid from reservoir 1002 into feed reservoir 1008). FIG. 11 is a graphical representation of selective retention of castor oil for small, medium and large GSD nanoemulsions using the setup 1000 of FIG. 10 (Mean for 3 tests; each using a new filter). The castor oil in retentate samples (e.g., aliquot from reservoir 1008) and permeate samples (e.g., aliquot from permeate flow exiting third port 1032) was quantified by using UPLC Method 1 and Method 2, respectively at 205 nm. As shown in FIG. 11, more than 90% of the castor oil was kept in the retentate at the end of one hour, irrespective of GSD. Thus, the AP process can effectively help in differentiating the rapid drug release from the extended phase drug release, allow for size-based separation, and provide simultaneous analyses of drug release from the separated components (e.g., in permeate and retentate).

Furthermore, there is an increasing need to analyze the role of critical excipients and their impact on drug release.

Complex excipients, such as polymers composed of hydrophilic and hydrophobic monomers, can be selectively retained based on their molecular weight by using the AP method. The impact of these polymers on drug release could then be studied, for example, by inducing compositional or manufacturing process changes and evaluating their effect on drug release of resulting product.

In addition, the continuous processes in the AP method (i.e., concomitant dilution of the sample and removal of the released drug from the membrane and recirculation of the remaining drug within the AP system) mimics in-vivo conditions, for example, continuous dilution of a drug on an ocular surface due to tear turnover and continuous absorption of drug after release from the complex formulation. Similarly, drug release testing using the AP method also closely resembles the drug release condition in parenteral drug delivery, where release of drug into the blood stream occurs during circulation and drug removal occurs due to absorption at the target tissue or organ.

Dilution ratio during release testing, which may be highly critical for some dosage forms such as ophthalmics, can be controlled using the AP method. Such control may be especially useful for nanosuspensions, where dilution can give rise to rapid (e.g., substantially instantaneous) dissolution of the nanoparticles and thereby diminish the possibility of differentiating formulations. Also, for nanoemulsions the initial equilibrium between the oil/aqueous phases present in the formulation governs the drug distribution in each phase. Thus, for very high dilution at the beginning of an IVRT may disturb this equilibrium and potentially mask the difference in drug distribution between formulations, especially if the rate of drug removal across the membrane is slow.

In the AP method, dilution rate can be controlled by adjusting the rate of permeate flow (e.g., by controlling feed flow rate via pump 1014 and/or back pressure via valve 1028) so that the sample could be diluted at a lower ratio initially, followed by higher dilution as the test progresses. This unique feature enables the AP method to potentially discern minor differences in drug release profiles of emulsions with different globule sizes. The AP method also provides the flexibility of tuning the rates of feed flow and fresh medium supply, which in turn governs the rate at which the drug sample gets diluted as well as the time necessary to complete an IVRT. The AP method can adjust these flow rates to avoid, or at least reduce, degradation of drug products that may degrade when otherwise exposed to large volume of media for a prolonged period (e.g., as occurred with the drug samples in comparative examples 1-2, FIGS. 8B, 9B).

Example 3—IVRT of Drug Products Using Adaptive Perfusion

Pure difluprednate solution and difluprednate polysorbate-80 micelles was evaluated using the setup 1000 of FIG. 10. For pure difluprednate solution, 200 μL of difluprednate solution (1 mg/mL in ethanol) was spiked (via conduit 1016) into 40 mL of release media (10 mM pH 7.4 phosphate buffer mixed with ethanol in the ratio of 80:20 v/v) in reservoir 1008 to reach an initial difluprednate concentration of 5 μg/mL. Ethanol was used as a co-solvent to prevent the precipitation of difluprednate in the media. Difluprednate concentrations in the retentate reservoir 1008 and permeate reservoir 1038 were determined in real time using an in-situ fiber optic UV-Vis system (Pion μDiss Profiler™, Billerica, MA). ZIM analysis was performed to remove polysorbate-80 interference by using wavelength within the range of 271-274 nm (exact ZIM wavelength varied between probes). For difluprednate polysorbate-80 micelles, 1 mL of difluprednate polysorbate-80 micelle solution (100 μg/mL in 3.6% w/v polysorbate-80) was spiked (via conduit 1016) into 40 mL of the release media (10 mM pH 7.4 phosphate buffer) in reservoir 1008 to obtain an initial difluprednate concentration of 2.5 μg/mL. Aliquots of retentate and permeate were collected periodically from the retentate reservoir 1008 and from the permeate tubing (between third port 1032 and permeate reservoir 1038), respectively, and subjected to UPLC analysis to determine difluprednate concentration. Appropriate dilution was performed for the retentate aliquots by using acetonitrile prior to UPLC analysis. The study was conducted at ambient room temperature (i.e., 23.5±1.5° C.).

In addition, to demonstrate the discriminatory capability of the AP method, IVRT was conducted for nanoemulsions having small, medium and large globule size distribution using the setup 1000 of FIG. 10. Several TFF hollow fiber filter modules having different MWCO of 30 kD, 100 kD, 300 kD and 500 kD (Spectrum MicroKros®, modified polyether sulfone (mPES) membrane, 20 $cm^2$ surface area, Repligen Corporation, CA, USA) were screened initially to select an optimal MWCO for the TFF filter for performing the in vitro release studies. 100 kD MWCO was eventually selected considering the range of globule sizes to be evaluated for the nanoemulsions. 200 μL of nanoemulsion was spiked (via conduit 1016) directly into 40 mL of media (10 mM pH 7.4 phosphate buffer) in reservoir 1008 to provide an initial concentration of 2.5 μg/mL for difluprednate. Aliquots of retentate and permeate were collected periodically from the retentate reservoir 1008 and from the permeate tubing (between outlet 1031 and 1038), respectively, and subjected to UPLC analysis to determine difluprednate concentration. Appropriate dilution was performed for the retentate aliquots by using acetonitrile prior to UPLC analysis. The study was conducted at ambient room temperature (i.e., 23.5±1.5° C.).

Figure 12A:
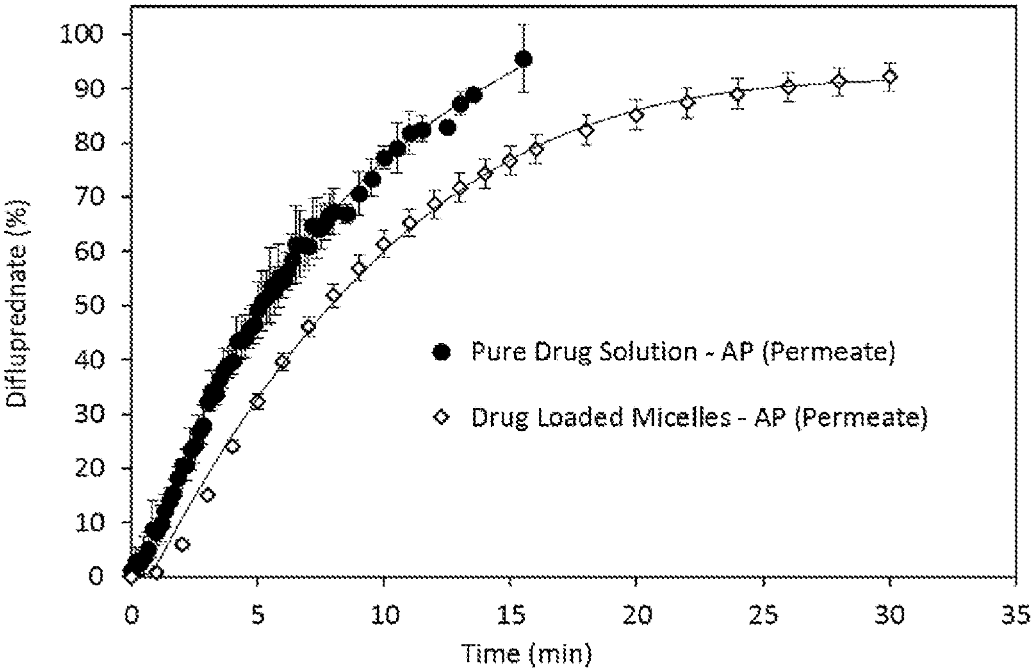
FIG. 12A is a graph of drug transfer profiles (percentage in permeate versus time) for pure drug solutions and drug-loaded micelles tested using the adaptive perfusion setup of FIG. 10.
Figure 12B:
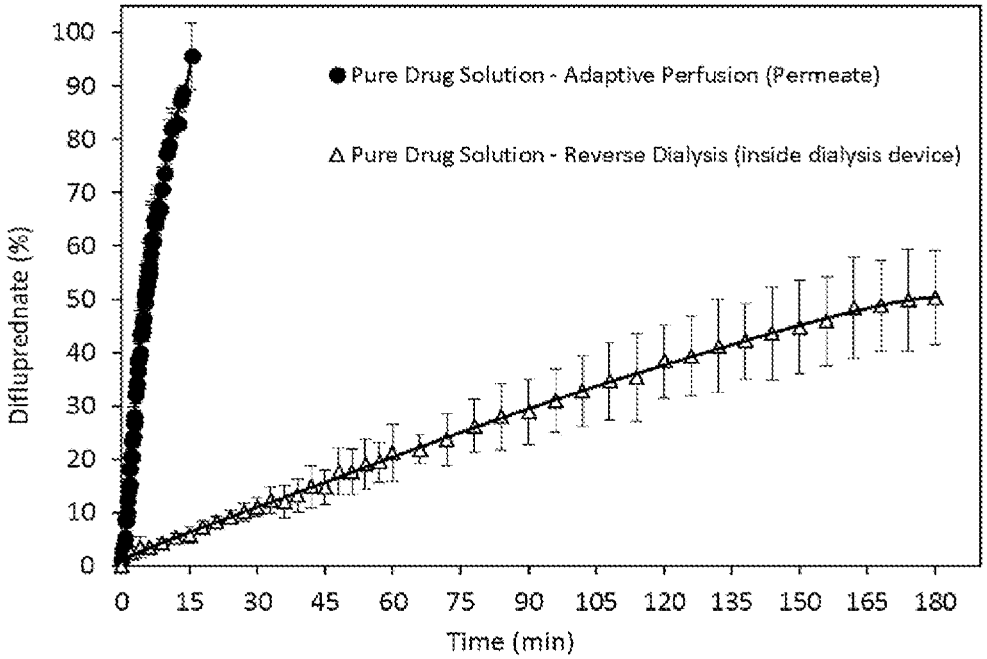
FIG. 12B is a graph comparing the drug transfer profile for a pure drug solution obtained using the adaptive perfusion setup of FIG. 10 and the drug release profile for a pure drug solution obtained using the reverse dialysis setup of FIG. 8A.

Drug transfer from the pure difluprednate solution and the difluprednate polysorbate-80 micelles was evaluated using setup 1000. FIG. 12A is a graphical representation overlaying drug transfer profiles for pure drug solution and drug loaded micelles obtained using the AP method in setup 1000 (Mean±SD, 3 tests each using a new filter), while FIG. 12B is a graphical representation comparing the drug transfer profile for pure drug solution obtained using the AP method to the drug transfer profile for pure drug solution obtained using reverse-dialysis methods (Mean±SD, 3 tests each using a new filter). As shown in FIG. 12A, more than 90% of the difluprednate transferred across the membrane (into the permeate) in less than 15 minutes (from pure solution), which was significantly faster compared to the reverse-dialysis method (see FIG. 12B).

Similar to the reverse-dialysis setup, 20% ethanol was used in the release media for testing of pure difluprednate solutions, in order to provide a comparison with the media used in reverse-dialysis method as well as to prevent drug precipitation due to the higher rate of drug transfer achieved with the AP method. In the AP method, diffusion of drug across the membrane may still occur, but it is otherwise overshadowed by the rapid drug transfer from the pressure driven-filtration process. In other words, the overall rate of drug transfer across the TFF membrane is primarily a function of the filtration process rather than diffusion. As shown in FIG. 12A, drug release from micelles was slower (reaching 90% of drug release in about 25 minutes) as compared to the diffusion of pure difluprednate solution (reaching 90% of drug release in less than 15 minutes). This is a notable capability of the AP method, as it can discern the differences in drug release rate between the free drug and the drug in micelles.

Figure 13:
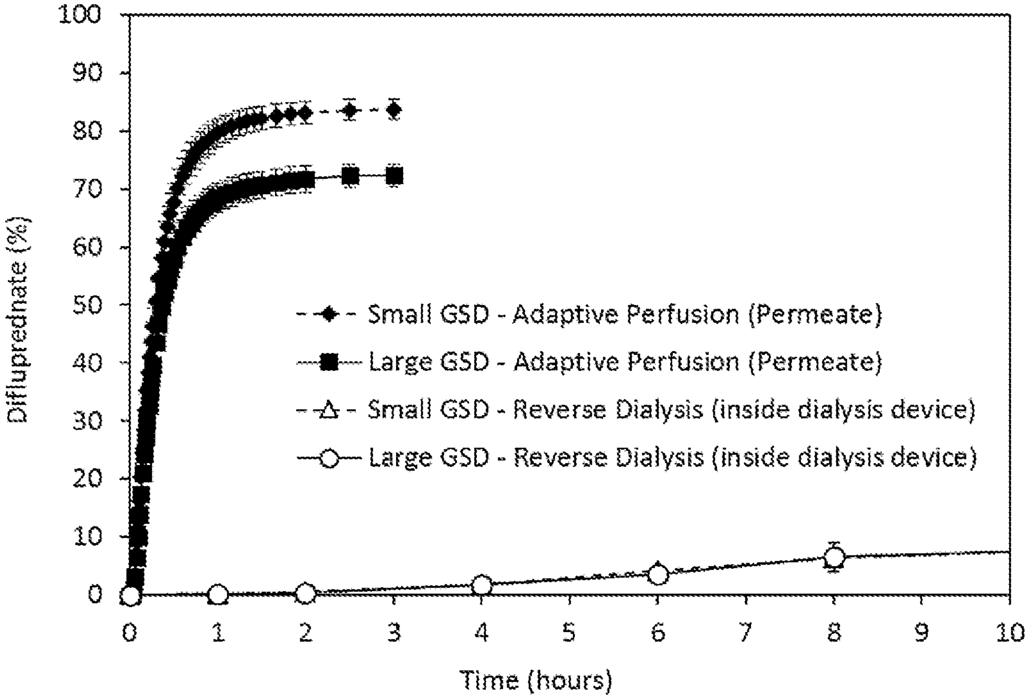
FIG. 13 is a graph comparing in vitro drug release profiles for various GSD nanoemulsions using the adaptive perfusion setup of FIG. 10 and the in vitro drug release profiles for various GSD nanoemulsions using the reverse dialysis setup of FIG. 9A.

With respect to nanoemulsions, FIG. 13 is a graphical representation comparing in vitro drug release profiles for small and large globule size nanoemulsions obtained using the AP method in setup 1000 to in vitro drug release profiles obtained using reverse-dialysis methods (Mean±SD, 3 tests each using a new filter). As shown in FIG. 13, released drug percentage (in the permeate) from both formulations plateaued in about 1 hour using the AP method, which was significantly faster than those in the reverse-dialysis method (>48 hours). The extent of drug release was also significantly higher in AP method than those in reverse-dialysis method. In particular, nearly 80% of the drug was released from small GSD nanoemulsion, and 68% of the drug was released from large GSD nanoemulsions, in comparison to only 18% in the reverse-dialysis method.

Figure 14A:
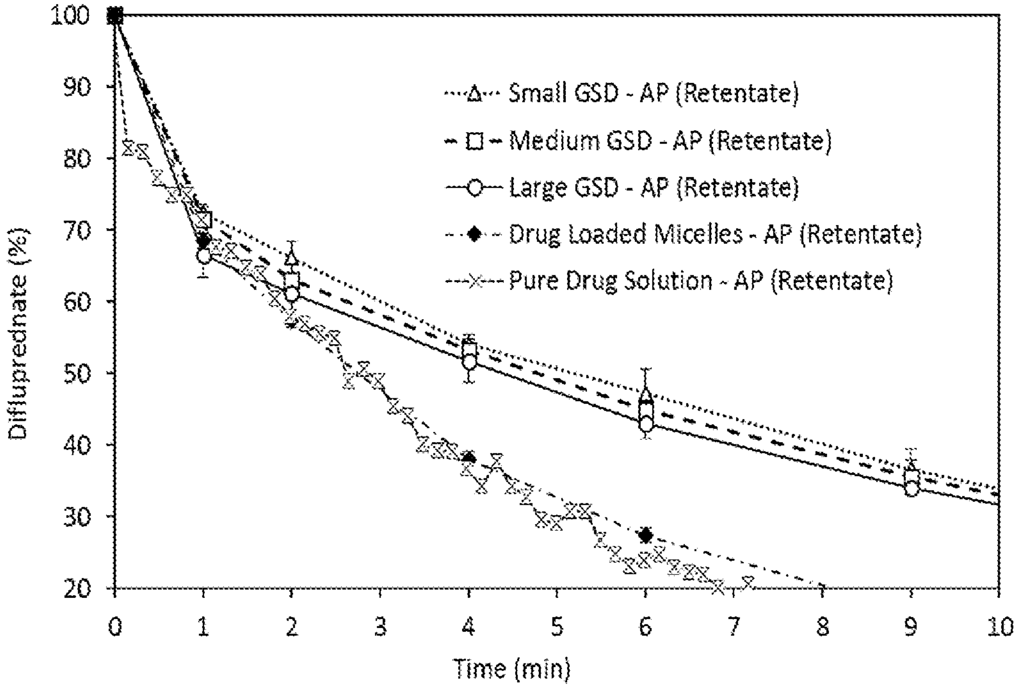
FIG. 14A is a graph of initial rates of drug removal and declines of drug concentrations in the retentate reservoir for various GSD nanoemulsions, pure drug solution, and drug-loaded micelles obtained using the adaptive perfusion setup of FIG. 10
Figure 14B:
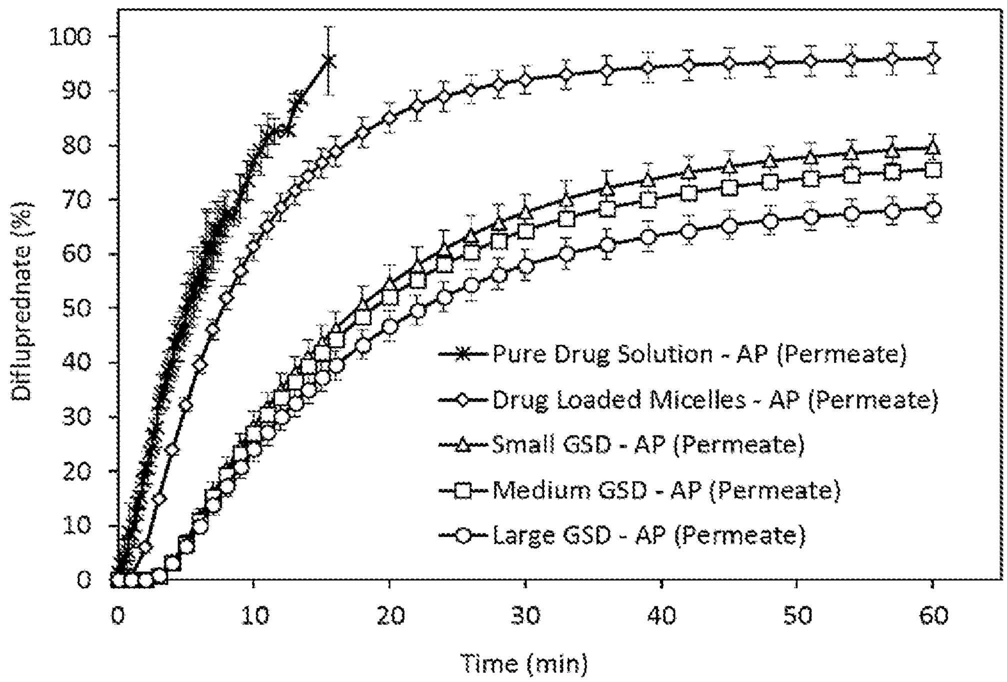
FIG. 14B is a graph of in vitro drug release in the permeate reservoir for various GSD nanoemulsions, pure drug solution, and drug-loaded micelles obtained using the adaptive perfusion setup of FIG. 10.

The change in rate of drug removal was subtle when a comparison was made between the different globule size nanoemulsions. However, as shown in FIG. 14A and Table 4, some level of rate reduction was still discernable between larger GSD nanoemulsions and smaller GSD nanoemulsions. As shown in FIG. 14B, statistically significant differences were also observed when the extent of drug release for pure drug solution, drug loaded micelles and nanoemulsions involving different GSD were compared.

The AP method was able to provide a clear discrimination between the release profiles of different globule size nanoemulsions. The most rapid extent of release came from smaller globules, followed by medium and larger globule size nanoemulsions. It should be further noted that the globule size difference between the large and small nanoemulsions was about 2.4 times higher when compared with that of the medium size nanoemulsions (see Table 1). This difference in the globule size distribution between the different nanoemulsions is evident by the difference observed in the extent of drug release from each of these formulations, as shown in FIG. 14B.

TABLE 4

Rate (first-order) and extent of drug transfer for pure drug solution, drug loaded micelles, large, medium and small globule size nanoemulsions for retentate and permeate using the AP method (mean ± sd, n = 3).

| | | Permeate | | |
|---|---|---|---|---|
| Sample | Retentate k* ($min^{-1}$) Mean ± SD | k* ($min^{-1}$) Mean ± SD | $t_{50}$ (min) Mean ± SD | Maximum Drug Release (%) Mean ± SD |
| Pure drug (DFP) solution | 0.211 ± 0.056 | 0.146 ± 0.018 | 5.3 ± 0.6 | 93.7 ± 5.5 |
| Drug loaded micelles | 0.155 ± 0.016 | 0.087 ± 0.015 | 7.7 ± 0.4 | 96.4 ± 3.1 |
| Large GSD nanoemulsion | 0.085 ± 0.002 | 0.031 ± 0.002 | 22.4 ± 2.0 | 72.4 ± 1.9 |
| Medium GSD nanoemulsion | 0.085 ± 0.001 | 0.037 ± 0.001 | 18.8 ± 0.1 | 79.6 ± 1.3 |
| Small GSD nanoemulsion | 0.083 ± 0.004 | 0.040 ± 0.003 | 17.8 ± 1.6 | 83.7 ± 1.7 |

*k is the first-order rate constant, determined by equations: $Q = 100*e^{-k*t}$ (retentate) and $Q = 100*(1 - e^{-k*t})$ (permeate)

As shown in Table 4 above, the AP method is capable of discriminating between samples of different dosage forms, e.g., pure drug solution, micelles, and nanoemulsions. A statistically significant difference was observed when the rates of drug transfer were compared for pure drug solution and drug loaded micelles with the nanoemulsions. The rates of drug transfer were reduced by almost 50% for nanoemulsions as compared to the pure drug solution and drug in micelles, which reduction was expected considering the additional barrier of drug transfer from oil globules to the release medium. The difference in terms of release media used for pure drug solution (i.e., 10 mM pH 7.4 phosphate buffer mixed with ethanol in the ratio of 80:20 v/v) from that used for drug loaded micelles and nanoemulsions (i.e., 10 mM pH 7.4 phosphate buffer) may also have contributed to the reduced drug transfer rate for nanoemulsions. However, the different release processes between solution, micelles, emulsions are expected to be the primary driver of the differences in drug transfer rates.

FIG. 14A is a graphical representation of initial rate of drug removal and the decline of drug concentration in the retentate reservoir for small, medium and large globule size nanoemulsions, pure drug solution and drug loaded micelles tested using the AP method in the setup 1000 of FIG. 10 (Mean±SD, 3 tests each using a new filter). FIG. 14B is a graphical representation of the extent of in vitro drug release in the permeate reservoir for small, medium and large globule size nanoemulsions, pure drug solution and drug loaded micelles tested using the AP method in the setup 1000 of FIG. 10 (Mean±SD, 3 tests each using a new filter).

Figure 14C:
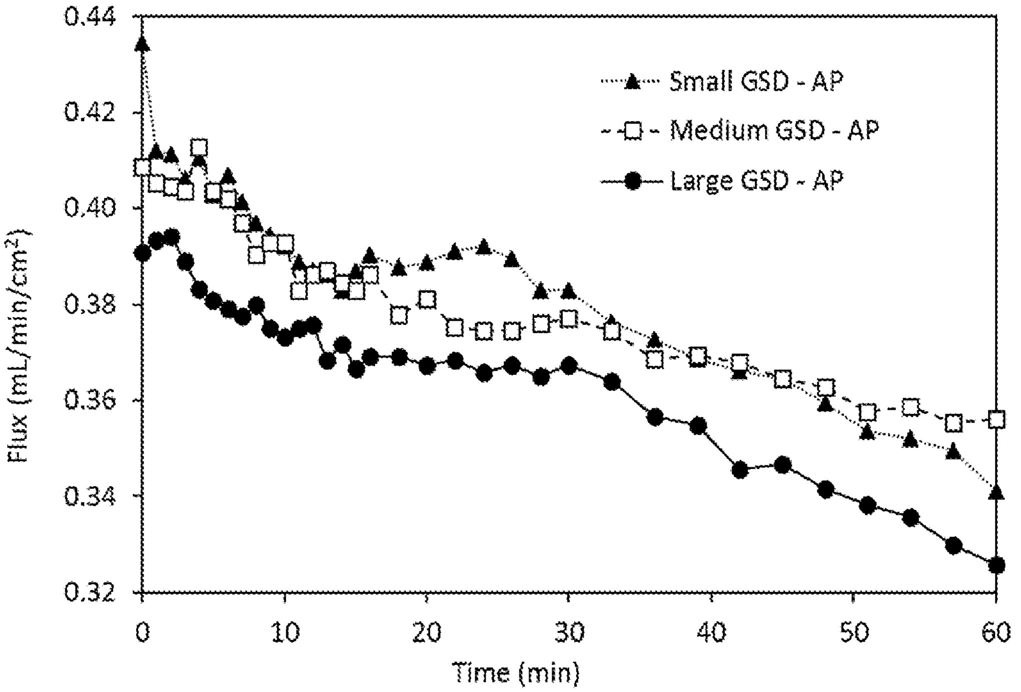
FIG. 14C is a graph of flux profiles for various GSD nanoemulsions obtained using the adaptive perfusion setup of FIG. 10.

FIG. 14C is a graphical representation of the flux profiles for small, medium and large globule size nanoemulsions tested using the AP method in the setup 1000 of FIG. 10 (Mean for 3 tests; each using a new filter). The flux during the AP process governs the extent of drug transfer from the HFF 1020 to the permeate reservoir 1038. As shown in FIG. 14C, flux was inversely proportional to the globule size, with smaller globule size corresponding to larger flux and vice versa. Hence, there was an increase in the extent of drug release with the decrease in the globule size.

The above described IVRT data for complex nanoemulsions using the AP method demonstrate that the rate and extent of drug release can be a product of surfactant distribution in the nanoemulsions and the flux during the AP process. In particular, surfactant distribution exhibited a direct correlation with the size of the globules, with larger globules (smaller surface area) requiring smaller amount of surfactant for stabilizing the interface. Accordingly, a higher percentage of surfactant was available in the bulk aqueous phase to form micelles. As suggested by FIG. 14A, based on the globule size of the nanoemulsion, distribution of surfactant controlled the initial rate of drug removal and the decline of drug concentration in the retentate reservoir, with faster decay resulting for larger globule size emulsions.

Example 4—Effect of Conditioning on Filter Performance

Figure 15A:
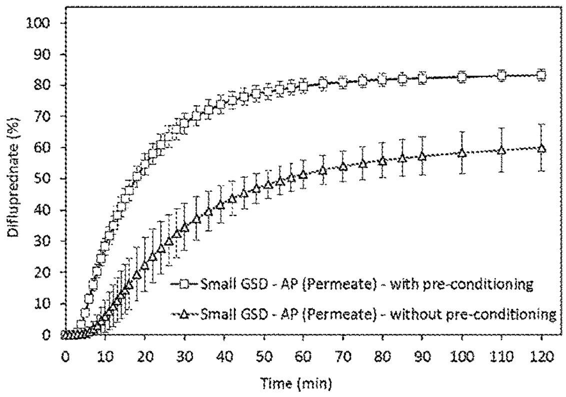
FIG. 15A is a graph of drug release profiles for small GSD nanoemulsions obtained using the adaptive perfusion setup of FIG. 10, with and without filter pre-conditioning.
Figure 15B:
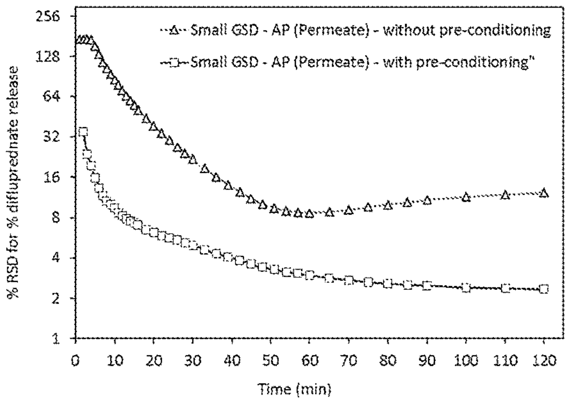
FIG. 15B is a graph of percent relative standard deviation (% RSD) of drug release versus time obtained using the adaptive perfusion setup of FIG. 10, with and without filter pre-conditioning.

To evaluate the effect of pre-conditioning on filter performance, IVRT was conducted for nanoemulsions having small GSD using the AP method in the setup of FIG. 10 with and without pre-conditioning of HFF 1020. For the pre-conditioning tests, HFF 1020 was subject to the process described above with respect to FIG. 5A using a conditioning solution of 0.07% w/v polysorbate-80 solution. For the no-pre-conditioning tests, the HFF 1020 was merely washed to remove manufacturer's storage media (e.g., only process blocks 506-510 of FIG. 5A). FIG. 15A is a graphical representation comparing the drug transfer profile for small GSD nanoemulsions using the AP method with filter pre-conditioning to the drug transfer profile for small GSD nanoemulsions using the AP method without filter pre-conditioning (Mean±SD, 3 tests each using a new filter). FIG. 15B is a graphical representation comparing percent relative standard deviation (% RSD) of drug release for small GSD nanoemulsions using the AP method with filter pre-conditioning to that obtained using the AP method without filter pre-conditioning (Mean±SD, 3 tests each using a new filter). As shown in FIGS. 15A-15B, the release of drug from the nanoemulsions is significantly enhanced by pre-conditioning HFF 1020.

Figure 15C:
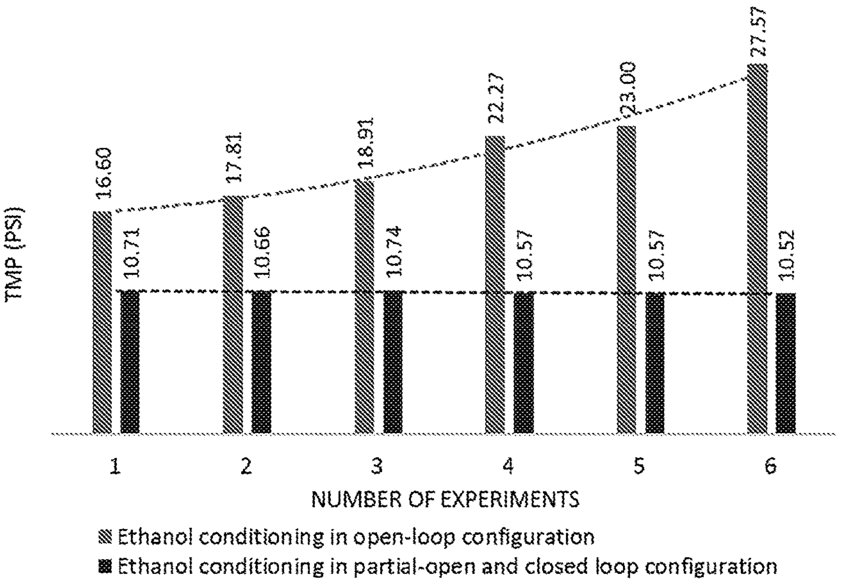
FIG. 15C is a graph of transmembrane pressure of the filter in the adaptive perfusion setup of FIG. 10 versus number of drug release experiments performed using the filter, for different conditioning configurations.

To evaluate the effect of pre-conditioning using partial open loop configuration of FIG. 5B on testing repeatability, transmembrane pressure (TMP) was measured during successive IVRT experiments (with re-conditioning between successive runs) using the AP method in the setup of FIG. 10 using different fluid circuit configurations, in particular, open loop (e.g., FIG. 6B), partial open loop (e.g., FIG. 5B), and closed loop (e.g., FIG. 7B). The conditioning solution used in each conditioning test was ethanol. FIG. 15C is a graphical representation comparing the measured TMP during successive runs for each of the different fluid circuit configurations for conditioning. As shown in FIG. 15C, conditioning of the filter using an open loop configuration led to an increase in TMP with increasing successive runs, while conditioning using the partial open loop configuration maintained a substantially constant TMP between IVRT runs. Since increases in TMP can impact the reproducibility of results, the more stable TMP offered by the HFF conditioned using the partial open loop configuration can yield improved accuracy, precision, or both.

Additional Examples of the Disclosed Technology

In view of the above described implementations of the disclosed subject matter, this application discloses the additional examples in the clauses enumerated below. It should be noted that one feature of a clause in isolation, or more than one feature of the clause taken in combination, and, optionally, in combination with one or more features of one or more further clauses are further examples also falling within the disclosure of this application.

Clause 1. A method, comprising:

- using a filter, performing a diafiltration process on a fluid having a drug sample therein, a retentate from the filter being recirculated to a fluid supply reservoir, a permeate flow from the filter being collected in a permeate reservoir;
- obtaining a first aliquot from the fluid supply reservoir or a flow of the fluid to the filter;
- obtaining a second aliquot from the permeate flow; and
- analyzing the first and second aliquots to determine one or more properties of the drug sample.

Clause 2. The method of clause 1, wherein the first aliquot and the second aliquot are obtained at a same time during the performance of the diafiltration process or after the performance of the diafiltration process.

Clause 3. The method of any one of clauses 1-2, wherein the first aliquot is obtained prior to the performance of the diafiltration process.

Clause 4. The method of any one of clauses 1-3, wherein the obtaining the first aliquot, the obtaining the second aliquot, and the analyzing the first and second aliquots are repeated periodically during the performance of the diafiltration process.

Clause 5. The method of any one of clauses 1-4, wherein the determined one or more properties of the drug sample comprises a percentage of the drug sample released over time.

Clause 6. The method of any one of clauses 1-5, wherein the analyzing comprises ultra-performance liquid chromatography (UPLC).

Clause 7. The method of any one of clauses 1-6, wherein the drug sample comprises a drug solution or suspension, drug-loaded micelles, nanoemulsions comprising drug molecules, or any combination of the above.

Clause 8. The method of any one of clauses 1-7, further comprising, prior to performing the diafiltration process, conditioning the filter by flowing a conditioning solution over retentate and permeate sides of each membrane in the filter.

Clause 9. The method of any one of clauses 1-8, further comprising, after the performing the diafiltration process, flowing a conditioning solution over retentate and permeate sides of each membrane in the filter, and storing the filter within the conditioning solution.

Clause 10. The method of any one of clauses 8-9, wherein the conditioning solution comprises a surfactant, an emulsifier, or both.

Clause 11. The method of clause 10, wherein the conditioning solution comprises polysorbate-80.

Clause 12. The method of any one of clauses 1-11, further comprising, after the performing the diafiltration process, flushing at least a retentate side of each membrane in the filter with a solvent, and recovering any drug sample retained in the solvent exiting the filter from the flushing.

Clause 13. The method of any one of clauses 1-12, wherein:

- the filter has an inlet, a first outlet, and a second outlet, the inlet and the first outlet connecting to a retentate volume disposed on one side of a membrane within the filter, the second outlet connecting to a permeate volume disposed on an opposite side of the membrane from the retentate volume; and
- the performing the diafiltration process comprises, at a same time:
  - flowing fluid from the fluid supply reservoir to the inlet of the filter at a first flow rate;
  - flowing fluid exiting the filter from the first outlet to the fluid supply reservoir while applying a back pressure to the first outlet, the back pressure inducing a pressure gradient across the membrane that drives at least some of the fluid from the retentate volume to the permeate volume;
  - collecting the permeate flow exiting the filter from the second outlet in the permeate reservoir; and
  - adding fluid to the fluid supply reservoir to compensate for fluid lost to the permeate flow, thereby maintaining a substantially constant volume of fluid in a combination of the fluid supply reservoir, the retentate volume, and a fluid circuit connecting the fluid supply reservoir and the filter together.

Clause 14. The method of clause 13, further comprising measuring a second flow rate of the permeate flow, wherein the adding fluid to the fluid supply reservoir is responsive to the measured second flow rate.

Clause 15. The method of any one of clauses 13-14, further comprising measuring volume, weight, or both of the fluid supply reservoir, the permeate reservoir, or both, wherein the adding fluid to the fluid supply reservoir is responsive to the measuring.

Clause 16. The method of any one of clauses 13-15, further comprising:

selecting the first flow rate based at least in part on a release rate of the drug sample;

selecting a pore size for the membrane of the filter defining a molecular weight cut-off based at least in part on an initial particle size of the drug sample and a particle size released from the drug sample; or any combination of the above.

Clause 17. A method for conditioning a filter for use in a diafiltration process involving a drug sample, the method comprising:

connecting a first port of a filter to a source of conditioning solution;

connecting a second port of the filter to a third port of the filter, the first port and the second port connecting to a first volume disposed on a first side of a membrane within the filter, the third port and a fourth port connecting to a second volume on an opposite second side of the membrane from the first side; and flowing conditioning solution from the source into the filter via the first port and out through the fourth port, such that the conditioning solution flows over the first and second sides of the membrane via the connection between the second and third ports, wherein the conditioning solution comprises a surfactant, an emulsifier, or both.

Clause 18. The method of clause 17, wherein the conditioning solution comprises polysorbate-80.

Clause 19. The method of any one of clauses 17-18, wherein the first side is a retentate side of the membrane, the second side is a permeate side of the membrane, the first and fourth ports are disposed at one end of the filter, and the second and third ports are disposed at an opposite end of the filter from the first and fourth ports.

Clause 20. The method of any one of clauses 17-19, further comprising, prior to or after the flowing conditioning solution, flowing deionized water into the filter via the first port and out through the fourth port, such that the deionized water flows over the first and second sides of the membrane via the connection between the second and third ports.

Clause 21. The method of any one of clauses 17-20, further comprising, after the flowing conditioning solution, storing the filter within the conditioning solution.

Clause 22. The method of any one of clauses 1-21, wherein the filter is a tangential flow filter.

Clause 23. The method of any one of clauses 1-22, wherein the filter is a hollow fiber filter.

Clause 24. A method, comprising:

using a filter, performing a diafiltration process on a fluid having a drug sample therein, a retentate from the filter being recirculated to a fluid supply reservoir, a permeate flow from the filter being collected in a permeate reservoir;

measuring a first concentration of the drug sample in the fluid supply reservoir;

measuring a second concentration of the drug sample in the permeate flow; and determining one or more properties of the drug sample based on the measured first and second concentrations.

Clause 25. The method of clause 24, wherein:

the measuring the first concentration and the measuring the second concentration is repeated periodically during the diafiltration process to yield a plurality of measured first and second concentrations, and the determining the one or more properties of the drug sample is based on the plurality of measured first and second concentrations.

Clause 26. The method of any one of clauses 24-25, wherein:

the measuring the first concentration is via a first concentration monitoring sensor coupled to the fluid supply reservoir; and/or the measuring the second concentration is via a second concentration monitoring sensor coupled to a flow-path between the filter and the permeate reservoir.

Clause 27. The method of clause 26, wherein the first concentration monitoring sensor, the second concentration monitoring sensor, or both comprise an in situ fiber optic ultra-violet (UV) sensor.

Clause 28. The method of any one of clauses 24-27, wherein:

the measuring the first concentration comprises obtaining a first aliquot from the fluid supply reservoir or a flow of the fluid to the filter, and analyzing the first aliquot; and/or the measuring the second concentration comprises obtaining a second aliquot from the permeate flow, and analyzing the second aliquot.

Clause 29. The method of clause 28, wherein the analyzing the first aliquot, the analyzing the second aliquot, or both comprises ultra-performance liquid chromatography (UPLC).

Clause 30. The method of any one of clauses 24-29, wherein the determined one or more properties of the drug sample comprises a percentage of the drug sample released over time.

Clause 31. The method of any one of clauses 24-30, wherein the drug sample comprises a drug solution or suspension, drug-loaded micelles, nanoemulsions comprising drug molecules, or any combination of the above.

32. The method of any one of clauses 24-31, wherein:

the filter has an inlet, a first outlet, and a second outlet, the inlet and the first outlet connecting to a retentate volume disposed on one side of a membrane within the filter, the second outlet connecting to a permeate volume disposed on an opposite side of the membrane from the retentate volume; and the performing the diafiltration process comprises, at a same time:

flowing fluid from the fluid supply reservoir to the inlet of the filter at a first flow rate;

flowing fluid exiting the filter from the first outlet to the fluid supply reservoir while applying a back pressure to the first outlet, the back pressure inducing a pressure gradient across the membrane that drives at least some of the fluid from the retentate volume to the permeate volume;

collecting the permeate flow exiting the filter from the second outlet in the permeate reservoir; and adding fluid to the fluid supply reservoir to compensate for fluid lost to the permeate flow, thereby maintaining a substantially constant volume of fluid in a combination of the fluid supply reservoir, the retentate volume, and a fluid circuit connecting the fluid supply reservoir and the filter together.

Clause 33. The method of clause 32, further comprising measuring a second flow rate of the permeate flow, wherein the adding fluid to the fluid supply reservoir is responsive to the measured second flow rate.

Clause 34. The method of any one of clauses 32-33, further comprising measuring volume, weight, or both of the fluid supply reservoir, the permeate reservoir, or both, wherein the adding fluid to the fluid supply reservoir is responsive to the measuring.

Clause 35. The method of any one of clauses 32-34, further comprising:

selecting the first flow rate based at least in part on a release rate of the drug sample;

selecting a pore size for the membrane of the filter defining a molecular weight cut-off based at least in part on an initial particle size of the drug sample and a particle size released from the drug sample; or any combination of the above.

Clause 36. The method of any one of clauses 24-35, further comprising, prior to performing the diafiltration process, conditioning the filter by flowing a conditioning solution over retentate and permeate sides of each membrane in the filter.

Clause 37. The method of any one of clauses 24-36, further comprising, after the performing the diafiltration process, flowing a conditioning solution over retentate and permeate sides of each membrane in the filter, and storing the filter within the conditioning solution.

Clause 38. The method of any one of clauses 36-37, wherein the conditioning solution comprises a surfactant, an emulsifier, or both.

Clause 39. The method of any one of clauses 36-38, wherein the conditioning solution comprises polysorbate-80.

Clause 40. The method of any one of clauses 24-39, further comprising, after the performing the diafiltration process, flushing at least a retentate side of each membrane in the filter with a solvent, and recovering any drug sample retained in the solvent exiting the filter from the flushing.

Clause 41. The method of any one of clauses 24-40, wherein the filter is a tangential flow filter.

Clause 42. The method of clause 41, wherein the filter is a hollow fiber filter.

Clause 43. A control system, comprising:

one or more processors; and computer-readable storage media storing computer-readable instructions that, when executed by the one or more processors, cause the one or more processors to control a system to perform the method of any one of clauses 1-42.

Clause 44. A method of conditioning a TFF filter with surfactant, the TFF filter being connected in a partial-open loop configuration, so as to minimize run-to-run and device-to-device variability, as otherwise described herein above.

Clause 45. A method of conducting drug release testing using a TFF filter with analysis of drug components in both the permeate and retentate, as otherwise described herein above.

Clause 46. A method of using an AP technique for size-based separation of complex drug product to study release characteristics thereof, as otherwise described herein above.

Clause 47. A method of using an AP technique to assess quality and performance differences in a complex drug product, as otherwise described herein above.

Clause 48. The method of any one of clauses 1-42 and 44-47, wherein the drug sample or the complex drug product comprises an emulsion, suspension, liposome, protein-drug complex, or any combination thereof.

Clause 49. An adaptive perfusion system, comprising:

one or more pumps;

one or more fluid conduits;

one or more reservoirs;

one or more sensors configured to measure at least one of pressure, flow rate, volume, or weight;

one or more flow control devices configured to direct or prevent flow through at least one of the fluid conduits;

one or more pressure control devices configured to apply a pressure to fluid flowing through at least one of the fluid conduits;

the control system according to clause 43; or any combination of the above, wherein the adaptive perfusion system is configured to perform the method of any one of clauses 1-42 and 44-47.

Clause 50. The adaptive perfusion system of clause 49, further comprising one or more in situ sensors configured to measure drug concentration, composition of a fluid, or both.

Clause 51. The adaptive perfusion system of clause 50, wherein the one or more in situ sensors comprises an in situ fiber optic ultra-violet (UV) sensor.

CONCLUSION

Any of the features illustrated or described with respect to FIGS. 1-15C, Examples 1-4, and Clauses 1-51 can be combined with any other of FIGS. 1-15C, Examples 1-4, and Clauses 1-51 to provide methods, systems, and embodiments not otherwise illustrated or specifically described herein.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods.

In view of the many possible embodiments to which the principles of the disclosed technology may be applied, it should be recognized that the illustrated embodiments are only preferred examples and should not be taken as limiting the scope of the disclosed technology. Rather, the scope is defined by the following claims. We therefore claim all that comes within the scope of these claims.

The invention claimed is:

1. A method, comprising:

using a filter, performing a diafiltration process on a fluid having a drug sample therein, a retentate from the filter being recirculated to a fluid supply reservoir, a permeate flow from the filter being collected in a permeate reservoir;

obtaining a first aliquot from the fluid supply reservoir or a flow of the fluid to the filter, wherein the first aliquot contains a mixture of a fluid supply and a retentate returned to the fluid supply;

obtaining a second aliquot from the permeate flow; and analyzing the first and second aliquots to determine one or more properties of the drug sample.

2. The method of claim 1, wherein the first aliquot and the second aliquot are obtained at a same time during the performance of the diafiltration process or after the performance of the diafiltration process.

3. The method of claim 1, wherein the first aliquot is obtained prior to the performance of the diafiltration process.

4. The method of claim 1, wherein the obtaining the first aliquot, the obtaining the second aliquot, and the analyzing the first and second aliquots are repeated periodically during the performance of the diafiltration process.

5. The method of claim 1, wherein the determined one or more properties of the drug sample comprises a percentage of the drug sample released over time.

6. The method of claim 1, wherein the analyzing comprises ultra-performance liquid chromatography (UPLC).

7. The method of claim 1, wherein the drug sample comprises a drug solution or suspension, drug-loaded micelles, nanoemulsions comprising drug molecules, or any combination of the above.

8. The method of claim 1, further comprising, prior to performing the diafiltration process, conditioning the filter by flowing a conditioning solution over retentate and permeate sides of each membrane in the filter.

9. The method of claim 1, further comprising, after the performing the diafiltration process, flowing a conditioning solution over retentate and permeate sides of each membrane in the filter, and storing the filter within the conditioning solution.

10. The method of claim 8, wherein the conditioning solution comprises a surfactant, an emulsifier, or both.

11. The method of claim 10, wherein the conditioning solution comprises polysorbate-80.

12. The method of claim 1, further comprising, after the performing the diafiltration process, flushing at least a retentate side of each membrane in the filter with a solvent, and recovering any drug sample retained in the solvent exiting the filter from the flushing.

13. The method of claim 1, wherein:

the filter has an inlet, a first outlet, and a second outlet, the inlet and the first outlet connecting to a retentate volume disposed on one side of a membrane within the filter, the second outlet connecting to a permeate volume disposed on an opposite side of the membrane from the retentate volume; and the performing the diafiltration process comprises, at a same time:

flowing fluid from the fluid supply reservoir to the inlet of the filter at a first flow rate;

flowing fluid exiting the filter from the first outlet to the fluid supply reservoir while applying a back pressure to the first outlet, the back pressure inducing a pressure gradient across the membrane that drives at least some of the fluid from the retentate volume to the permeate volume;

collecting the permeate flow exiting the filter from the second outlet in the permeate reservoir; and adding fluid to the fluid supply reservoir to compensate for fluid lost to the permeate flow, thereby maintaining a substantially constant volume of fluid in a combination of the fluid supply reservoir, the retentate volume, and a fluid circuit connecting the fluid supply reservoir and the filter together.

14. The method of claim 13, further comprising measuring a second flow rate of the permeate flow, wherein the adding fluid to the fluid supply reservoir is responsive to the measured second flow rate.

15. The method of claim 13, further comprising measuring volume, weight, or both of the fluid supply reservoir, the permeate reservoir, or both, wherein the adding fluid to the fluid supply reservoir is responsive to the measuring.

16. The method of claim 13, further comprising:

selecting the first flow rate based at least in part on a release rate of the drug sample;

selecting a pore size for the membrane of the filter defining a molecular weight cut-off based at least in part on an initial particle size of the drug sample and a particle size released from the drug sample; or any combination of the above.

17. The method of claim 1, further comprising conditioning the filter for use in the diafiltration process on the fluid having the drug sample by:

connecting a first port of the filter to a source of conditioning solution;

connecting a second port of the filter to a third port of the filter, the first port and the second port connecting to a first volume disposed on a first side of a membrane within the filter, the third port and a fourth port connecting to a second volume on an opposite second side of the membrane from the first side; and flowing conditioning solution from the source into the filter via the first port and out through the fourth port, such that the conditioning solution flows over the first and second sides of the membrane via the connection between the second and third ports, wherein the conditioning solution comprises a surfactant, an emulsifier, or both.

18. The method of claim 17, wherein the conditioning solution comprises polysorbate-80.

19. The method of claim 17, wherein the first side is a retentate side of the membrane, the second side is a permeate side of the membrane, the first and fourth ports are disposed at one end of the filter, and the second and third ports are disposed at an opposite end of the filter from the first and fourth ports.

20. The method of claim 17, further comprising, prior to or after the flowing conditioning solution, flowing deionized water into the filter via the first port and out through the fourth port, such that the deionized water flows over the first and second sides of the membrane via the connection between the second and third ports.

21. The method of claim 17, further comprising, after the flowing conditioning solution, storing the filter within the conditioning solution.

22. The method of claim 1, wherein the filter is a tangential flow filter.

23. The method of claim 22, wherein the filter is a hollow fiber filter.

24. A method, comprising:

using a filter, performing a diafiltration process on a fluid having a drug sample therein, a retentate from the filter being recirculated to a fluid supply reservoir, a permeate flow from the filter being collected in a permeate reservoir, wherein the fluid supply reservoir contains a mixture of the drug sample and the retentate;

measuring a first concentration of the drug sample in the fluid supply reservoir;

measuring a second concentration of the drug sample in the permeate flow; and determining one or more properties of the drug sample based on the measured first and second concentrations.

25. The method of claim 24, wherein:

the measuring the first concentration and the measuring the second concentration is repeated periodically during the diafiltration process to yield a plurality of measured first and second concentrations, and the determining the one or more properties of the drug sample is based on the plurality of measured first and second concentrations.

26. The method of claim 24, wherein:

the measuring the first concentration is via a first concentration monitoring sensor coupled to the fluid supply reservoir; and/or the measuring the second concentration is via a second concentration monitoring sensor coupled to a flow-path between the filter and the permeate reservoir.

27. The method of claim 26, wherein the first concentration monitoring sensor, the second concentration monitoring sensor, or both comprise an in situ fiber optic ultra-violet (UV) sensor.

28. The method of claim 24, wherein:

the measuring the first concentration comprises obtaining a first aliquot from the fluid supply reservoir or a flow of the fluid to the filter, and analyzing the first aliquot; and/or the measuring the second concentration comprises obtaining a second aliquot from the permeate flow, and analyzing the second aliquot.

29. The method of claim 28, wherein the analyzing the first aliquot, the analyzing the second aliquot, or both comprises ultra-performance liquid chromatography (UPLC).

30. The method of claim 24, wherein the determined one or more properties of the drug sample comprises a percentage of the drug sample released over time.

31. The method of claim 24, wherein the drug sample comprises a drug solution or suspension, drug-loaded micelles, nanoemulsions comprising drug molecules, or any combination of the above.

32. The method of claim 24, wherein:

the filter has an inlet, a first outlet, and a second outlet, the inlet and the first outlet connecting to a retentate volume disposed on one side of a membrane within the filter, the second outlet connecting to a permeate volume disposed on an opposite side of the membrane from the retentate volume; and the performing the diafiltration process comprises, at a same time:

flowing fluid from the fluid supply reservoir to the inlet of the filter at a first flow rate;

flowing fluid exiting the filter from the first outlet to the fluid supply reservoir while applying a back pressure to the first outlet, the back pressure inducing a pressure gradient across the membrane that drives at least some of the fluid from the retentate volume to the permeate volume;

collecting the permeate flow exiting the filter from the second outlet in the permeate reservoir; and adding fluid to the fluid supply reservoir to compensate for fluid lost to the permeate flow, thereby maintaining a substantially constant volume of fluid in a combination of the fluid supply reservoir, the retentate volume, and a fluid circuit connecting the fluid supply reservoir and the filter together.

33. The method of claim 32, further comprising measuring a second flow rate of the permeate flow, wherein the adding fluid to the fluid supply reservoir is responsive to the measured second flow rate.

34. The method of claim 32, further comprising measuring volume, weight, or both of the fluid supply reservoir, the permeate reservoir, or both, wherein the adding fluid to the fluid supply reservoir is responsive to the measuring.

35. The method of claim 32, further comprising:

selecting the first flow rate based at least in part on a release rate of the drug sample;

selecting a pore size for the membrane of the filter defining a molecular weight cut-off based at least in part on an initial particle size of the drug sample and a particle size released from the drug sample; or any combination of the above.

36. The method of claim 24, further comprising, prior to performing the diafiltration process, conditioning the filter by flowing a conditioning solution over retentate and permeate sides of each membrane in the filter.

37. The method of claim 24, further comprising, after the performing the diafiltration process, flowing a conditioning solution over retentate and permeate sides of each membrane in the filter, and storing the filter within the conditioning solution.

38. The method of claim 36, wherein the conditioning solution comprises a surfactant, an emulsifier, or both.

39. The method of claim 38, wherein the conditioning solution comprises polysorbate-80.

40. The method of claim 24, further comprising, after the performing the diafiltration process, flushing at least a retentate side of each membrane in the filter with a solvent, and recovering any drug sample retained in the solvent exiting the filter from the flushing.

41. The method of claim 24, wherein the filter is a tangential flow filter.

42. The method of claim 41, wherein the filter is a hollow fiber filter.

43. A control system, comprising:

one or more processors; and computer-readable storage media storing computer-readable instructions that, when executed by the one or more processors, cause the one or more processors to control a system to perform the method of claim 1.

44. A method, comprising:

using a filter, performing a diafiltration process on a fluid containing drug particles, a retentate from the filter being recirculated to a fluid supply reservoir, a permeate flow from the filter being collected in a permeate reservoir, the permeate flow containing drug released from the drug particles;

obtaining a first aliquot from the fluid supply reservoir or a flow of the fluid to the filter, wherein the first aliquot contains a mixture of a fluid supply and a retentate returned to the fluid supply;

obtaining a second aliquot from the permeate flow; and analyzing the unreleased drug in the first aliquot and the released drug in the second aliquot to determine one or more properties of the drug sample.

45. The method of claim 44, wherein the drug particles are provided in a suspension, a nanoemulsion, as drug-loaded micelles, liposomes, microspheres, or in a or any combination thereof.

* * * * *